US009468670B2

(12) United States Patent
Alpini et al.

(10) Patent No.: US 9,468,670 B2
(45) Date of Patent: Oct. 18, 2016

(54) MELATONIN-BASED TREATMENT AND DIAGNOSIS OF BILE DUCT DISEASE

(75) Inventors: Gianfranco Alpini, Temple, TX (US); Sharon DeMorrow, Harker Heights, TX (US); Shannon Glaser, Rogers, TX (US)

(73) Assignees: Texas A&M University System, College Station, TX (US); The United States of America as Represented by the Department of Veterans Affairs, Washington, DC (US); Scott & White Healthcare, Temple, TX (US)

( * ) Notice: Subject to any disclaimer, the term of this patent is extended or adjusted under 35 U.S.C. 154(b) by 0 days.

(21) Appl. No.: 14/009,276

(22) PCT Filed: Apr. 2, 2012

(86) PCT No.: PCT/US2012/031886
§ 371 (c)(1),
(2), (4) Date: Dec. 3, 2013

(87) PCT Pub. No.: WO2012/135848
PCT Pub. Date: Oct. 4, 2012

(65) Prior Publication Data
US 2014/0079680 A1 Mar. 20, 2014

Related U.S. Application Data

(60) Provisional application No. 61/470,904, filed on Apr. 1, 2011.

(51) Int. Cl.
| | |
|---|---|
| *A61K 48/00* | (2006.01) |
| *C07H 21/02* | (2006.01) |
| *C07H 21/04* | (2006.01) |
| *A61K 38/43* | (2006.01) |
| *A61K 38/45* | (2006.01) |
| *A61K 31/4045* | (2006.01) |
| *A61K 31/713* | (2006.01) |
| *G01N 33/574* | (2006.01) |
| *C12N 15/113* | (2010.01) |

(52) U.S. Cl.
CPC .......... *A61K 38/43* (2013.01); *A61K 31/4045* (2013.01); *A61K 31/713* (2013.01); *A61K 38/45* (2013.01); *A61K 48/005* (2013.01); *C12N 15/1137* (2013.01); *C12Y 201/01004* (2013.01); *C12Y 203/01087* (2013.01); *G01N 33/57488* (2013.01); *A61K 48/00* (2013.01); *C12N 2310/11* (2013.01); *C12N 2310/141* (2013.01); *C12N 2310/3233* (2013.01); *C12N 2320/11* (2013.01)

(58) Field of Classification Search
CPC ............................ A61K 48/00; C12N 15/113
See application file for complete search history.

(56) References Cited

U.S. PATENT DOCUMENTS

| | | | |
|---|---|---|---|
| 7,858,084 B2 * | 12/2010 | Desir ..................... | A61K 38/44 424/94.4 |
| 2003/0144570 A1 | 7/2003 | Hunter et al. | |
| 2009/0306101 A1 | 12/2009 | Solca et al. | |

OTHER PUBLICATIONS

International Preliminary Report on Patentability mailed Oct. 1, 2013, during examination of International Application No. PCT/US2012/031886.
Renzi et al., "Melatonin inhibits cholangiocyte hyperplasia in cholestatic rats by interaction with MT1 but not MT2 melatonin receptors", Am J Physiol Gastrointest Liver Physiol, Jul. 21, 2011, vol. 301, pp. G634-G643.
Han et al., "Melatonin exerts by an autocrine loop antiproliferative effects in cholangiocarcinoma; its synthesis is reduced favoring cholangiocarcinoma growth", Am J Physiol Gastrointest Liver Physiol, Jul. 21, 2011, vol. 301, pp. G623-G633.
Dusio et al., "Increased synthesis of melatonin from pineal gland and cholangiocytes (by prolonged exposure of cholestatic rats to complete dark) leads to inhibition of biliary hyperplasia by autocrine/paracrine mechanisms", ScholarOne Abstracts, Dec. 11, 2011, http://ddw2012.abstractcentral.com.
Han et al, "Upregulation of serotonin N-acetyltransferase (AANAT, the central enzyme involved in the biliary synthesis of melatonin) decreases cholangiocarcinoma growth by an autocrine mechanism" ScholarOne Abstract, Jun. 1, 2010, http://aasld2010.abstractcentral.com.
Han et al., "Melatonin inhibits in vivo cholangiocarcinoma growth by enhanced biliary expression of serotonin N-acetyltransferase (AANAT) the key enzyme involved in melatonin synthesis" ScholarOne Abstract, Nov. 29, 2010, http://ddw2011.abstractcentral.com.
Han et al., "Suppression of miR-34a expression by melatonin blocks human cholangiocarcinoma tumor growth and invasion" ScholarOne Abstract, May 31, 2011, http://aasld2011.abstractcentral.com.
Renzi et al., "Melatonin increases the expression of miR-141 reducing the proliferation of cholangiocytes by targeting Clock and Cry1", ScholarOne Abstract, May 31, 2011, https://secure.scholarone.com.

(Continued)

*Primary Examiner* — Amy Bowman
(74) *Attorney, Agent, or Firm* — Norton Rose Fulbright US LLP

(57) ABSTRACT

Methods and composition for a melatonin signaling modulator-based diagnosis and therapy are described. For example, in certain aspects methods for administering an anti-tumor therapy using a melatonin signaling modulator are described. Furthermore, the invention provides compositions and methods for detecting biliary tract disease such as cholangiocarcinoma.

6 Claims, 27 Drawing Sheets

(56) References Cited

OTHER PUBLICATIONS

Ashley et al., "The Targeted Delivery of Multicomponent Cargos to Cancer Cells via Nanoporous Particle-Supported Lipid Bilayers" National Institute of Health, May 2011, vol. 10, Issue 5, pp. 389-397.

Sezer et al., "Effects of Intraperitoneal Meltonin on Caustic Sclerosing Cholangitis Due to Scolicidal Solution in a Rat Motel", Current Therapeutic Research, Apr. 2010, vol. 71, No. 2, pp. 118-128.

Renzi et al., "Increased Expression of Serotonin N-Acetyltransferase (AANAT, The Key Enzyme Responsible for the Synthesis of Melatonin) in Cholangiocytes Causes Inhibition of Biliary Proliferation: Evidence for a Novel Autocrine Lopper Regulating Biliary Hyperplasia", Heptology, Oct. 2010, AASLD, p. 924A.

Han et al., "Abstract 631: Decreased Melatonin Synthesis in Cholangiocarcinoma (CCA) Suppresses its Antiproliferative Actions by Upregulation of Clock Gene", Gastroenterology, May 2010, vol. 138, Issue 5, Supplement 1, pp. S792-S-793.

International Search Report and Written Opinion mailed Nov. 3, 2012, during examination of International Application No. PCT/US2012/031886.

Ohta, Y., et al; "Therapeutic Effect of Melatonin on Cholestatic Liver Injury in Rats with Bile Duct Ligation"; Adv. Exp. Med. Biol., 2003; 527:559-65.

Kus, I, et al; "Protective Effects of Melatonin Against Carbon Tetrachloride-Induced Hepatotoxicity in Rats: A Light Microscopic and Biochemical Study"; Cell Biochem Funct., May-Jun. 2005; 23(3): 169-74.

* cited by examiner

FIGS. 7A-7C
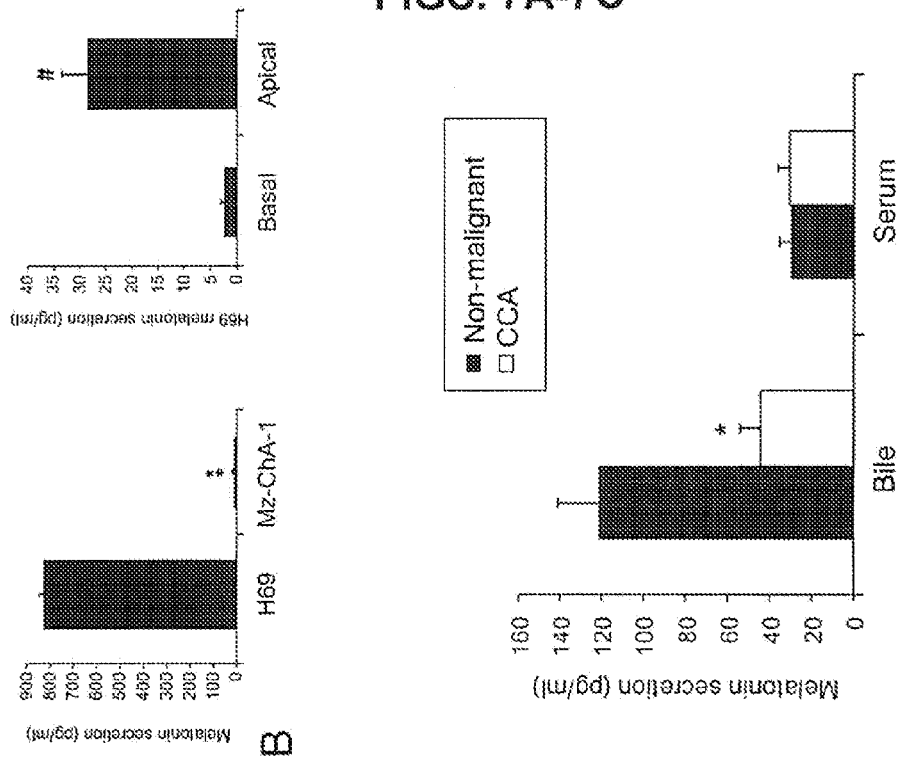
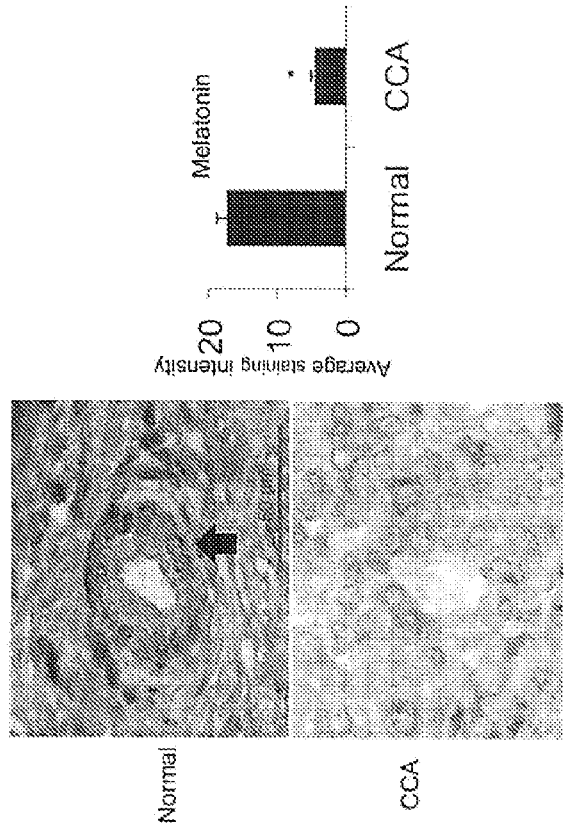

FIG. 16 A-B
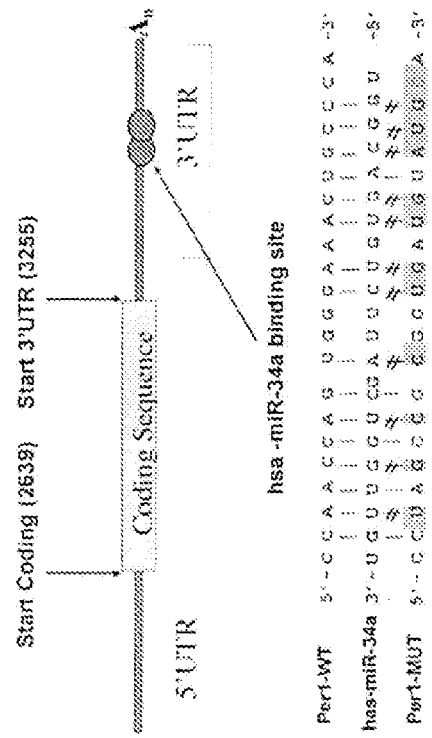
B    Homo sapiens Per1 isoform
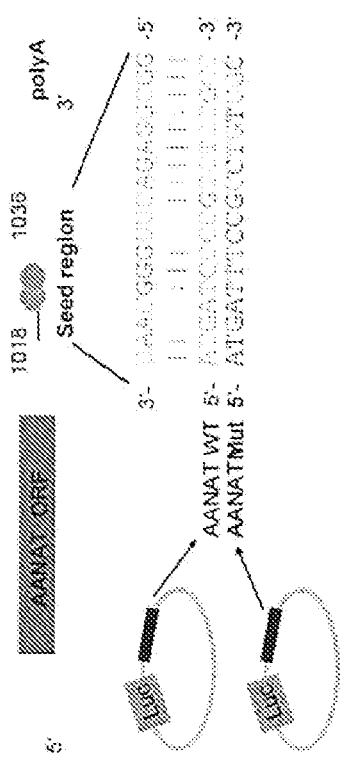
A    Target site of miR-25 on 3'-UTR of AANAT FIG. 16 C-D
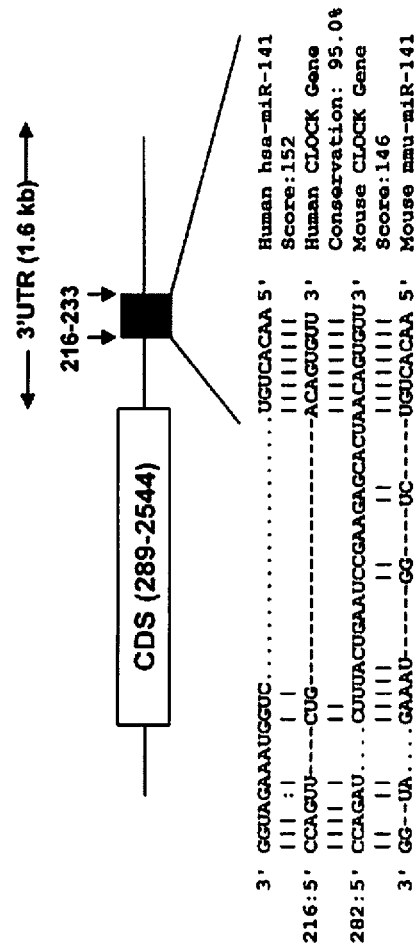
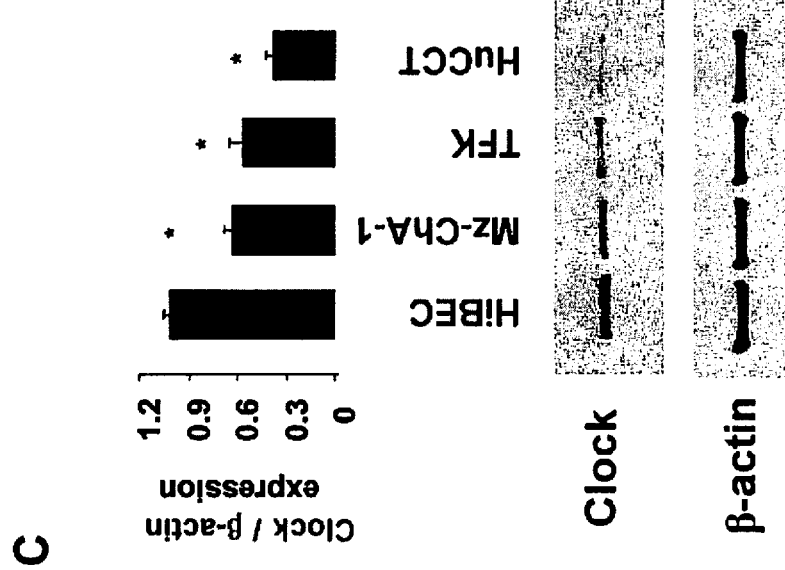

FIG. 16 E-F
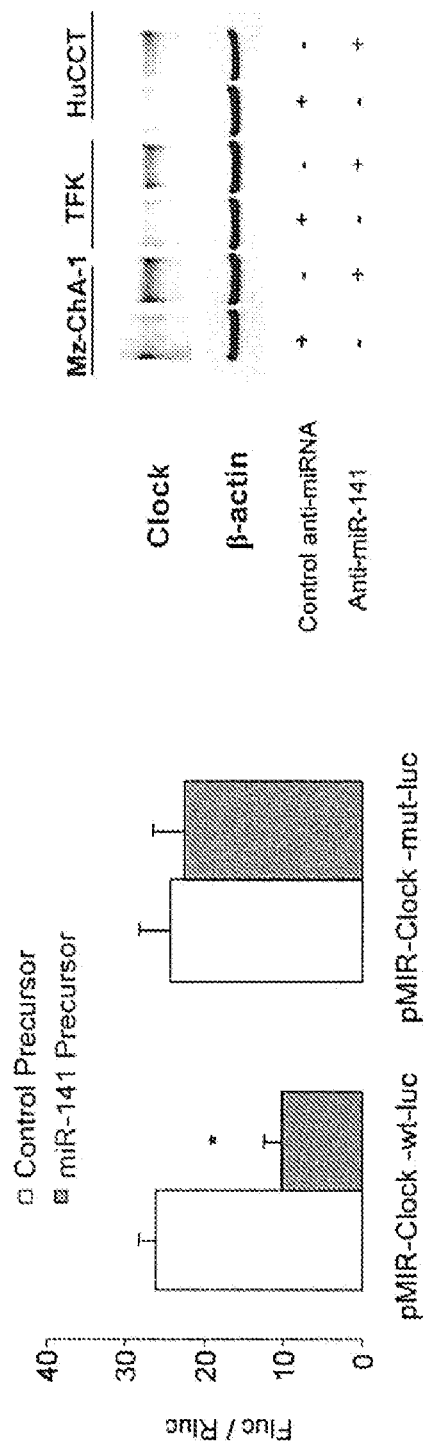

```
SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Synthetic primer

<400> SEQUENCE: 1
gttccccagc tttggaagtg gtccc                                           25

<210> SEQ ID NO 2
<211> LENGTH: 25
<212> TYPE: DNA
<213> ORGANISM: Artificial Sequence
<220> FEATURE:
<223> OTHER INFORMATION: Synthetic primer

<400> SEQUENCE: 2
gttcccgacc tttgcaactc gtccc                                           25
```

MELATONIN-BASED TREATMENT AND DIAGNOSIS OF BILE DUCT DISEASE

This application is a national phase filing under 35 USC 371 of PCT International Patent Application Serial No. PCT/US2012/031886, filed Apr. 2, 2012, which claims priority to U.S. Provisional Patent Application 61/470,904, filed Apr. 1, 2011, both of which applications are incorporated by reference herein in their entirety.

This invention was made with government support under DK062975, DK768981, and DK054811 awarded by National Institutes of Health. The government has certain rights in the invention.

BACKGROUND OF THE INVENTION

1. Field of the Invention

The present invention relates generally to the field of molecular biology, bile duct disease, and diagnosis. More particularly, it concerns methods for treatment of a subject by administration of a melatonin signaling modulator. The invention also generally pertains to methods for diagnosis of biliary tract disease, such as cholangiocarcinoma.

2. Description of Related Art

Diseases of the biliary tract are a common cause of morbidity and mortality in the U.S. Cancer of the biliary mucosa, cholangiocarcinoma (CCA), results from the malignant transformation of cholangiocytes, which line intrahepatic and extrahepatic bile ducts of the liver (Lazaridis and Gores, 2005). The pathogenesis of CCA is linked to chronic biliary proliferation and inflammation, which occurs in cholestatic liver diseases including primary sclerosing cholangitis (PSC). CCA is clinically silent and mostly diagnosed as an advanced disease resulting in limited therapeutic options (Malhi and Gores, 2006). Recent evidence indicates that the proliferating biliary mucosa serves as a neuroendocrine compartment during the pathogenesis of liver diseases, and as such, secrete and respond to hormones, neurotransmitters and neuropeptides contributing to the autocrine and paracrine pathways that positively and/or negatively modulate liver inflammation, fibrosis and biliary carcinogenesis (Alvaro et al., 2007). While advances have been in the understanding of the neuroendocrine factors that modulate biliary mucosa growth during the progression of liver diseases and the ultimate development of CCA, unfortunately, viable therapies for the management of CCA remain elusive. On the other hand, currently cholangiocarcinoma diagnosis relies on examination of tumor tissue, which may be inconvenient for early detection.

There remains, therefore, a need of novel methods for diagnosis and therapy of diseases of the biliary tract, such as cholangiocarcinoma.

SUMMARY OF THE INVENTION

Aspects of the present invention overcome a major deficiency in the art by providing novel methods and compositions for treating a subject with a disease involving cholangiocytes with gene therapy, cell therapy, melatonin therapy, or additional anti-tumor therapy. Aspects of the invention include a method for treating a subject with a bile duct pathological condition having increased proliferation of cholangiocytes in the subject. The increased proliferation may be a proliferation rate higher than a reference level of proliferation, such as proliferation of normal cholangiocytes. The method may comprise administering to the subject in need thereof one or more melatonin signaling modulators at an amount effective to inhibit proliferation of cholangiocytes, thereby treating the condition having increased proliferation of cholangiocytes in the subject. The treatment method may comprise additional therapy, such as a cell-based therapy, a gene therapy, a radiotherapy, a chemotherapy, an immunotherapy, modification of exposure of the subject to light or darkness, or a combination thereof. The melatonin signaling modulator may include or exclude melatonin itself.

Non-limiting examples of melatonin signaling modulators may include an AANAT (aralkylamine N-acetyltransferase) enhancer, an exogenous ASMT (acetylserotonin O-methyltransferase) enhancer, an exogenous Per1 (period circadian protein homolog 1) enhancer, an exogenous Bmal1 (period circadian protein homolog 1) inhibitor, an exogenous CLOCK (period circadian protein homolog 1) enhancer, or melatonin.

The enhancer or inhibitor may enhance or inhibit the expression or activity of corresponding genes. The enhancer or inhibitor may be a small molecule, a peptide, a polypeptide, an antibody, an antibody fragment, a DNA, or an RNA. For inhibiting gene expression, the inhibitor may be an inhibitory nucleic acid or a inhibitory nucleic acid analog, such as shRNA (for example as those commercially available from SABiosciences), siRNA, dsRNA, or morpholino. For inhibiting activity, the inhibitor may be a small molecule inhibitor or an antibody or antibody fragment. For enhancing expression in the cell, the enhancer may be an exogenous nucleic acid, which may comprise DNA, RNA, or a combination thereof. In a particular example, the AANAT enhancer may be an exogenous AANAT expression cassette; the AANAT inhibitor may inhibit expression of AANAT or the enzyme activity of AANAT, such as inhibitory nucleic acid or analog or a small molecule inhibitor as known in the art.

For example, the melatonin signaling modulators may comprise an exogenous AANAT expression cassette, an exogenous ASMT expression cassette, an exogenous Per1 expression cassette, an exogenous Bmal1 inhibitory nucleic acid or nucleic acid analog or an antibody fragment that binds Bmal1, or an exogenous CLOCK expression cassette.

For example, the exogenous expression cassette may further comprise a second coding sequence, such as a reporter gene, a therapeutic gene, a signaling sequence, or a trafficking sequence. The exogenous expression cassette may be comprised in a gene delivery vehicle. Examples of a gene delivery vehicle include, but are not limited to, a lipid, a liposome, lipofectamine, a plasmid, a viral vector, a phage, a polyamino acid, a particle, calcium phosphate, or DEAE-dextran. The administration of a gene delivery vehicle may include pulmonary administration, endobronchial administration, topical administration, intraocular administration, parenteral administration, intravenous administration, intrahepatic administration, intranasal administration, intratracheal administration, intrabronchial administration, intranasal administration, injection into the biliary tree, endoscopic administration into the biliary tree via endoscopic guidance, administration under endoscopic retrograde cholangiopancreatography (ERCP) guidance, administration under endoscopic ultrasound guidance, or subcutaneous administration. For tumor targeting, the exogenous expression cassette may further comprise a tumor-selective promoter or a sequence encoding a tumor-targeting moiety.

The administration of melatonin modulators may be or may not be an oral administration. For example, the administration may involve intravenous administration, intracardiac administration, intradermal administration, intralesional administration, intrathecal administration, intracranial administration, intrapericardial administration, intraumbilical administration, intraocular administration, intraarterial administration, intraperitoneal administration, intraosseous administration, intrahemmorhage administration, intratrauma administration, intratumoral administration, topical administration to a tumor intraoperatively, subcutaneous administration, intramuscular administration, intravitreous administration, direct injection into a normal tissue or organ, direct injection into a diseased tissue or organ like a tumor, topical administration, or any other method of local or systemic administration known to those of ordinary skill in the art. In a particular aspect, the administration may comprise targeted administration to cholangiocytes, such as cholangiocarcinoma cells, in the subject. In certain embodiments, the bile tract disease comprises administration of a pharmaceutically effective amount of a therapeutic agent such as melatonin or an analog of melatonin into the biliary tract of the subject. Administration into the biliary tract of the subject may be via any method known to those of ordinary skill in the art, such as via ERCP.

Melatonin analog may be a compound that binds to at least one receptor for melatonin, including for example, the melatonin 1a receptor and/or the melatonin 1b receptor. The melatonin analog may be any of 2-iodomelatonin, 6-chloromelatonin, 6,7-dichloro-2-methylmelatonin and 8-hydroxymelatonin.

The composition may comprise one or more additional therapeutic agents. A therapeutic agent may be administered at about or at most 1, 5, 10, 15, 20, 25, 30, 35, 40, 45, 50, 55, 60, 65, 70, 75, 80, 90, 100, 150, 200, 500, 1000, 2000, 3000, 5000, 10,000 µg or any range derivable therein.

The condition to be treated may a bile duct disease, such as biliary hyperplasia, cholangiopathy, or cholangiocarcinoma. For example, the condition may be cholangiopathy, such as primary biliary cirrhosis (PBC) or primary sclerosing cholangitis (PSC). In a further aspect, the condition may be cholangiocarcinoma. Particularly, the cholangiocarcinoma may not be a non-resectable cholangiocarcinoma. In another aspect, the cholangiocarcinoma may be a non-resectable cholangiocarcinoma. The cholangiocytes may be cholangiocarcinoma cells. In a particular aspect, the cholangiocarcinoma may not be induced by *Opisthorchis viverrini*. In a certain aspect, the subject may or may not have liver pathological conditions, such as a liver cancer.

The subject to be treated or diagnosed may be any animal, such as a human, a mouse, a rat, or any other mammal.

In a further aspect, a method may be provided for treating a bile duct damage and/or loss in a subject. The method may comprise administering to the subject in need thereof an AANAT inhibitor at an amount effective to increase proliferation and/or reduce apoptosis of the cholangiocytes, thereby treating the bile duct damage and/or loss in the subject. The AANAT inhibitor may inhibit expression of AANAT or the enzyme activity of AANAT. For inhibiting AANAT expression, the AANAT inhibitor may be an inhibitory nucleic acid or a inhibitory nucleic acid analog, such as shRNA, siRNA, dsRNA, or morpholino. In further aspects, the AANAT inhibitor may be small molecule inhibitor, such as described in Szewczuk et al. (2007); Ferry et al. (2004); Zheng and Cole (2003); Lepailleur et al. (2010).

There may be further provided a method of treating a subject with a known or suspected disease of the biliary tract. The method may comprise administering to a subject with known or suspected biliary tract disease a pharmaceutically effective amount of a composition comprising melatonin or a melatonin analog, wherein the composition is injected into a bile duct of the subject. For example, the administration may comprise performing ERCP-guided administration of the composition or endoscopic ultrasound-guided fine needle delivery of the composition.

There may also be provided a method for detecting a cholangiocarcinoma in a subject by using a fluid sample or a tissue sample. The fluid sample or tissue sample may be a biopsy sample obtained, for example, by transabdominal biopsy, biopsy using ERCP, or biopsy performed under fluoroscopic or ultrasonic guidance. The method may comprise determining the expression level of melatonin signaling modulator genes (such as AANAT, ASMT, Per1, Bmal1, or CLOCK) or a melatonin level. A lower expression level of AANAT, ASMT, Per1, or CLOCK, or a higher expression level of Bmal1 compared to a reference level is indicative of an increased risk of having or developing cholangiocarcinoma. The tissue sample may be a biopsy sample, such as fine needle aspirates or resected sample.

In a particular aspect, the method may comprise determining a level of melatonin in a bile sample of the subject, thereby detecting a cholangiocarcinoma in the subject. A decrease in the melatonin level relative to a reference level may indicate that the subjects have an increased risk of having or developing cholangiocarcinoma. The decrease in the melatonin level may be at least about 2, 3, 4, 5, 6, 7, 8, 9, 10, 11, 12, 13, 14, 15, 16, 17, 18, 19, 20 fold lower than a reference level thereof, or any intermediate values or ranges. In a particular aspect, the decrease in the melatonin level may be at least about 8 fold lower than a reference level. The method may further comprise preparing a report of the biomarker levels and/or diagnosis.

In certain aspects, comparison of the results of the above analyses is made to a reference level. For example, the reference level may be a level of melatonin in a bile sample, used for comparison may be a reference level from a control sample, such as non-cancerous tissue from the same subject. Alternatively, the reference level may be a reference level from a different subject or group of subjects. For example, the reference level may be a level obtained from tissue of a subject or group of subjects without cancer, or a level obtained from non-cancerous tissue of a subject or group of subjects with cancer. The reference level may be a single value or may be a range of values. The reference level can be determined using any method known to those of ordinary skill in the art. In some embodiments, the reference level is an average level determined from a cohort of subjects with cancer or without cancer. The reference level may also be depicted graphically as an area on a graph.

Also disclosed are biliary stents or stone retrieval balloons coated with a therapeutically effective amount of a composition comprising melatonin, a melatonin analog, or a melatonin modulator as set forth herein.

In some embodiments of the invention, there is a method of modulating expression of arylalkylamine N-acetyltransferase (AANAT) in a cholangiocyte by delivering to the cholangiocyte an agent that 1) decreases activity or expression of AANAT in the cholangiocyte; or 2) increases activity or expression of AANAT in the cholangiocyte. The cholangiocyte may be present in vivo in an individual, and in some aspects the cholangiocyte is in the liver, the pineal gland, or both.

In aspects of the invention, one can modify AANAT to affect its activity and/or expression in biliary tissues or cells and/or tissues or cells in the pineal gland. In some embodiments, the cells are cholangiocytes in the liver and/or pineal gland. In specific embodiments the modulation of expression of AANAT indirectly or directly impacts the level of melatonin in the cholangiocyte, including by increasing or decreasing the melatonin level. In cases wherein the activity and/or expression of AANAT is reduced, there is increased proliferation of biliary tree; in specific aspects this occurs by decreases in melatonin, although in alternative embodiments this occurs by another mechanism. In certain embodiments the increase in proliferation of biliary tree occurs in an individual that is in need of proliferation of biliary tree, such as one that has a disease where there is need for proliferation of biliary tree. The disease may be of any kind in need of biliary tree proliferation, but in certain aspects the disease is drug-induced ductopenia, alcohol-induced liver fibrosis, congenital ductopenia, liver transplant recipient. In specific cases of liver transplant the transplant is a living donor transplant.

In cases where the activity and/or expression of AANAT is increased, there is decreased proliferation of biliary tree, and in specific embodiments this occurs through an increase in melatonin, although alternatively it occurs through an alternative mechanism. In certain embodiments the decrease in proliferation of biliary tree occurs in an individual that is in need of decreased proliferation of biliary tree, such as one that has a disease where there is need for decreased proliferation of biliary tree. The disease may be of any kind in need of decreased biliary tree proliferation, but in certain aspects the disease is obstruction of biliary tree with marked biliary hyperplasia, for example. Biliary obstruction may refer to the blockage of any duct that carries bile from the liver to the gallbladder or from the gallbladder to the small intestine.

Disclosed herein are methods of systemic or local administration of AANAT modulators to an individual, including local administration to the liver and/or pineal gland. However, in specific aspects of the invention there is local targeting to the cholangiocyte of one or more modulators of AANAT expression. The local targeting may occur by any means, including by utilizing compositions that comprise both the modulator of AANAT expression and a targeting moiety. The liver-specific and/or pineal gland-specific targeting moiety may be of any kind, but in specific embodiments it is a nanoparticle, peptide, antibody, a hybrid between liposomes and nanoporous silica nanoparticles (Ashey et al., 2011), and so forth. The nanoparticle may be configured, such as by size and/or shape and/or composition, to specifically target a liver, pineal gland, and/or cholangiocyte. Exemplary liver-specific nanoparticles include Gal-50 and Gal-140 (galactosylated 50 and 140 nm nanoparticles) and MeO-50 and MeO-140 (methoxyterminated 50 and 140 nm nanoparticles) (Popielarski et al., 2005). Other exemplary liver-specific nanoparticles include galactose conjugated PLGA nanoparticles (Gupta et al., 2012); nanoparticles comprising a liver-specific ligand (Tian et al., 2010); and nanoparticles comprising poly(butylcyanoacrylate) and hydroxypropyl-β-cyclodextrins (HP-β-CD) (Li et al., 2011). Nanoparticles may be used that are alginate-chitosan nanoparticles or compositions comprising antibodies and nanoparticles (Chen et al., 2010) or nanoparticles comprising polyethyleneimine loaded into polylactide (Laroui et al., 2011). The nanoparticle may be further modified to comprise an entity that targets it to a liver, pineal gland, and/or cholangiocyte, such as a cell surface marker. In addition to nanoparticles, one may deliver AANAT modulators via liposomes or vector, including viral and non-viral vectors; exemplary viral vectors include lentiviral, adenoviral, retroviral, and adeno-associated vectors.

In some embodiments of methods of the invention, including methods wherein AANAT expression is modulated in an individual to affect biliary tree proliferation or decrease thereof, an individual subjected to the method may be provided an additional method that modulates melatonin production, such as modification of exposure to light or darkness. In additional or alternative aspects of the invention, an individual is subject to modulation of expression of AANAT in the pineal gland, such as targeting expression of AANAT to the pineal gland. Also encompassed in the invention are methods of modulating expression of AANAT in cholangiocytes in the liver and/or pineal gland in which an individual is also subjected to modulation of expression of ASMT and the clock genes Per1, Bmal1, and/or CLOCK.

In some embodiments of the invention, hepatocytes are determined to express AANAT and are subject to modulation of expression of AANAT for a therapeutic purpose, for example during alcohol-induced liver damage or steatosis.

Disclosed herein are methods wherein an individual has a medical condition in need of increased proliferation of biliary tree and the individual is provided a therapeutically effective amount of an agent that decreases activity or expression of AANAT in the cholangiocyte. In certain embodiments, the agent that decreases activity or expression of AANAT in the cholangiocyte is selected from the group consisting of Coenzyme A-S-acetyltryptamine, morpholino, siRNA, miRNA, and small molecules. In methods wherein miRNA is employed to modulated expression of AANAT, the miRNA may be selected from the group consisting of miRNA-17, miRNA-19, miRNA-34, miRNA 125b, miRNA-132, miR-4279, miR-875-3p, miR-1299, miR-626, miR-483-5p, miR-542-5p, hsa-miR-129*, hsa-miR-129-3p, hsa-miR-610, hsa-miR-1915, hsa-miR-541, hsa-miR-654-5p, hsa-miR-326, hsa-miR-330-5p, hsa-miR-885-3p, hsa-miR-1253, hsa-miR-136, hsa-miR-1972, hsa-miR-4261, hsa-miR-1207-3p, hsa-miR-518c*, hsa-miR-1225-3p, hsa-miR-93*, hsa-miR-877*, hsa-miR-96*, hsa-miR-575, and a mixture thereof (any may be hsa). Exemplary methods in which a medical condition is in need of increased proliferation of include liver transplant (including living donor liver transplant), drug-induced ductopenia, congenital ducopenia, and primary biliary cirrhosis. In some embodiments of living donor liver transplant, the donor for the liver transplant is provided an agent that increases activity or expression of AANAT in cholangiocytes in the donor liver.

Also disclosed herein are methods wherein an individual has a medical condition in need of reduced proliferation of biliary tree and the individual is provided a therapeutically effective amount of an agent that increases activity or expression of AANAT in the cholangiocyte, such as a small molecule, melatonin, or a melatonin analog, for example. The condition that is in need of reduced proliferation of biliary tree includes biliary obstruction, for example, including obstruction that is the result of malignancy, infection, biliary cirrhosis, primary sclerosing cholangitis and cholangiocarcinoma, and/or gall stone diseases.

In some aspects of the invention wherein AANAT expression is modulated to affect increase or decrease of biliary tree proliferation, one or more of the following is delivered to the individual i) an exogenous AANAT (aralkylamine N-acetyltransferase) expression cassette, ii) an exogenous ASMT (acetylserotonin O-methyltransferase) expression cassette, iii) an exogenous Per1 (period circadian protein homolog 1) expression cassette, iv) an exogenous Bmal1 (brain and muscle aryl hydrocarbon receptor nuclear translocator (ARNT)-like) inhibitory nucleic acid or nucleic acid analog, v) an exogenous CLOCK (Circadian Locomotor Output Cycles Kaput) expression cassette, and vi) melatonin.

Encompassed in the invention also are methods for modulating the amount of melatonin production by biliary tree in the individual, including by modulating expression of AANAT expression, for example.

Embodiments discussed in the context of methods and/or compositions of the invention may be employed with respect to any other method or composition described herein. Thus, an embodiment pertaining to one method or composition may be applied to other methods and compositions of the invention as well.

Nonalcoholic steatohepatitis or alcohol cirrhosis are treated in embodiments of the invention, including with modulators of AANAT expression in cholangiocytes, such as agents that increase AANAT activity and/or expression.

Intrahepatic cholangiocarcinoma or extrahepatic cholangiocarcinoma are treated in embodiments of the invention, including with modulators of AANAT expression in cholangiocytes, such as agents that decrease AANAT activity and/or expression.

As used herein the terms "encode" or "encoding" with reference to a nucleic acid are used to make the invention readily understandable by the skilled artisan; however, these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

[FIG. 1B] By FACS analysis, the protein expression of PER1, BMAL1, CRY1 and CLOCK decreased in cholangiocytes from BDL rats treated with melatonin in vivo compared to cholangiocytes from BDL rats treated with vehicle. Data are mean SEM of three evaluations. $^*p<0.05$ vs. the values of normal cholangiocytes. $^\#p<0.05$ vs. the values of normal and BDL cholangiocytes from rats treated with regular tap water.

[FIG. 2B] By FACS analysis the protein expression of MT1 and MT2 decreased in cholangiocytes from BDL rats treated with melatonin in vivo compared to cholangiocytes from BDL rats treated with vehicle. Data are mean SEM of three evaluations. $^\#p<0.05$ vs. the values of BDL cholangiocytes from rats treated with regular tap water.

[FIGS. 3B-D] Effect of melatonin on the expression of [FIG. 3B] PCNA, and the phosphorylation of [FIG. 3C] PKA and [FIG. 3D] ERK1/2 in purified large cholangiocytes. By immunoblots, there decreased PCNA expression and reduced ERK2 and PKA phosphorylation in large cholangiocytes from melatonin-treated BDL rats compared to large cholangiocytes from BDL controls. Data are mean SEM of 4 blots from cumulative preparations of cholangiocytes. $^*p<0.05$ vs. the corresponding values of large cholangiocytes from BDL controls.

[FIG. 5B] By FACS analysis the protein expression of MT1 and MT2 decreased in large mouse cholangiocyte lines after melatonin treatment compared to basal large mouse cholangiocyte lines. Data are mean SEM of three evaluations. $^*p<0.05$ vs. the corresponding basal values of large cholangiocyte lines.

[FIG. 6B] By FACS analysis the protein expression for AANAT and ASMT decreased in Mz-ChA-1 cells compared to H69 cells. Data are mean±SEM of four experiments. *p<0.05 vs. the values of nonmalignant human cholangiocytes. [FIG. 6C] The immunohistochemical expression of AANAT and ASMT significantly decreased in biopsy liver samples from CCA patients compared to controls. Data are mean±SEM of ninety evaluations for CCA patients and four for normal nonmalignant controls. *p<0.05 vs. the values of liver biopsy samples from nonmalignant controls.

FIGS. 7A-7C Evaluation of melatonin level in nonmalignant and CCA lines and liver biopsy samples from controls and CCA patients [FIG. 7A] Melatonin immunoreactivity is significantly decreased in liver biopsy samples from CCA patients compared to nonmalignant controls. Data are mean±SEM of ninety evaluations for CCA patients and four for nonmalignant control evaluations. *p<0.05 vs. the values of liver biopsy samples from nonmalignant controls. [FIG. 7B] The secretion of melatonin decreased in Mz-ChA-1 lines compared to H69 cells; notably, the secretion of melatonin was significantly higher in the apical domain of H69. Data are mean±SEM of 3 evaluations. *p<0.05 vs. the values of nonmalignant human cholangiocytes. [FIG. 7C] There were decreased melatonin levels in the bile (but not serum) of CCA patients compared to controls. Data are mean±SEM of x evaluations. *p<0.05 vs. the corresponding values of from normal healthy controls.

[FIG. 8C] The expression of MT1 and MT2 increased in liver biopsy samples from CCA patients compared to nonmalignant controls. Data are mean±SEM of ninety evaluations for CCA patients and four for nonmalignant control evaluations. *p<0.05 vs. the corresponding values of control lines and control patients, respectively.

FIG. 16 shows candidate core circadian gene targets of specific miRNA group. A: the location of the putative miR-25 target site in the AANAT1 3'-UTR is shown. A comparison of base pairs between mature human miR-25 target site on 3'-UTR of AANAT gene is shown. The sequence of the mutated target site with mutations to disrupt base pairing between miR-25 binding sites and AANAT is also displayed. B: a candidate binding site of miR-34a to Per1. Top panel represents the isoform of Per1 mRNA. The miR-34a-predicted target sites are shown in double circles. The bottom panel represents an exemplary luciferase construct that is used for in vitro assay. C-F, miR-141 regulates expression of Clock. C: Western blot analysis and densitometric analysis of relative expression levels of Clock and β-actin were performed in normal human cholangiocytes and CCA cell lines. The increase in CLOCK was observed in both malignant cell lines. D: Schematic of predicted miR-141 site in the 3' UTR of human Clock. E: Luciferase reporter constructs containing the miR-141 recognition sequence from the 3'-UTR of Clock inserted downstream of the luciferase gene were generated. pMIR-CLOCK-wt-luck contains the intact sequence whereas pMIR-CLOCK-mut-luc contained the sequence with random nucleotide changes. Reporter constructs were co-transfected with either miR-141 precursor or control precursor in normal human liver sinusoidal endothelial cells. The expression of firefly luciferase activity was normalized to that of Renilla luciferase activity for each sample. A decrease in relative firefly luciferase activity in the presence of miR-141 indicates the existence of a miR-141 modulated target sequence in the 3'-UTR of Clock. Data represents mean from eight separate experiments. F: Cells were transfected with miR-141 or control inhibitor. Cell lysates were obtained after 48 hours and western blots performed for CLOCK and β-actin. Treatment with anti-miR-141 increased the expression of CLOCK in all 3 CCA cell lines. *p<0.05 relative to specific control group.

DESCRIPTION OF ILLUSTRATIVE EMBODIMENTS

I. Melatonin Signaling Modulators

Figures 1A, 1B:
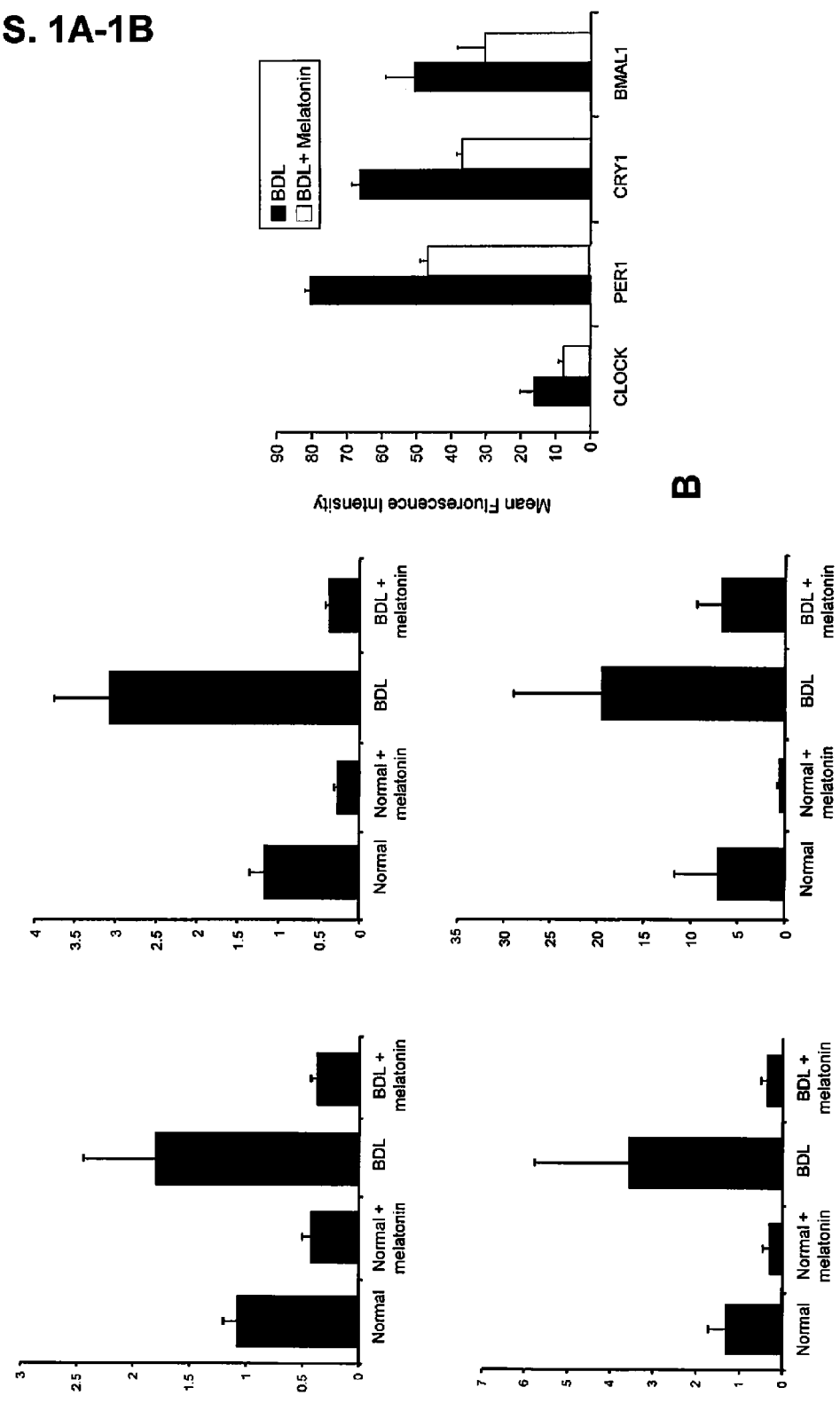
FIG. 1A-1B [FIG. 1A] By real-time PCR, the mRNA expression of PER1, BMAL1, CRY1 and CLOCK increased in BDL compared to normal cholangiocytes, but decreased in cholangiocytes from normal and BDL rats treated with melatonin in vivo compared to control cholangiocytes.

Certain aspects of the invention may be based, in part, on the discovery that modulation of the melatonin signaling pathway may have an effect on cholangiocyte proliferation and/or apoptosis. Thus, in certain aspects of the present invention, compositions and methods involving modulators of melatonin signaling pathways may be provided for treating cholangiocyte pathological conditions, particularly cholangiocarcinoma.

Melatonin, (whose synthesis is mainly regulated by the enzyme AANAT) (Zawilska et al., 2009), is a hormone produced in the brain by the pineal gland from the amino acid tryptophan. The synthesis and release of melatonin from the pineal gland (central) are stimulated by darkness and suppressed by light, suggesting the involvement of melatonin in circadian rhythm and regulation of diverse body functions (Zawilska et al., 2009). Melatonin is also produced in peripheral sites including mast cells (Maldonado et al., 2009), and the gastrointestinal tract (Bubenik, 2002). Circadian rhythms are controlled by a complex mechanism of feedback loops that involve at least eight core circadian genes: CLOCK, BMAL1 (ARNTL), period 1 (PER1), PER2, PER3, cryptochrome 1 (CRY1), CRY2, and casein kinase 1 epsilon (CSNK1E) (Eismann et al., 2010). In addition to a central clock, peripheral cells have their own circadian clocks and express clock genes, which regulate cell growth (Eismann et al., 2010). Studies have shown that: (i) melatonin has anti-proliferative effects in a number of cancers; and (ii) dysregulation of the expression of core circadian genes occurs in cancer cells (Fu and Lee, 2003; Cabrera et al., 2010; Yang et al., 2009). However, the roles of melatonin synthesis and circadian gene expression in the regulation of cholangiocarcinoma growth have not been examined.

In certain embodiments, melatonin analogs may be used as melatonin signaling modulators. Non-limiting examples of melatonin analogs may include one or more of the following: N-[2-(5-Methoxy-1H-indol-3-yl)ethyl]acetamide (TAK-375), N-[2-(3-ethyl-7-methoxynaphthyl)ethyl]-acetamide (S21634), N-[2-(7-methoxynaphth-1-yl)-ethyl]-acetamide (S20098), N-[2-naphth-1-yl-ethyl]-cyclobutyl carboxamide (S20928), 2-iodomelatonin, N-acetyl-5-HT, LY 156735, BMS-214778, agomelatine, CGP 52608, low-dose melatonin A, GR196429, S20242, S23478, S24268, S25150, melatonin receptor research compound A, GW290569, controlled release melatonin, luzindole, GR135531, Melatonin Agonist A (IMSWorld R&D Focus August 2002), Melatonin Analogue B (Pharmaprojects August 1998), Melatonin Agonist C (Chem. Pharm. Bull. (Tokyo) January 2002) Melatonin Agonist D (J. Pineal Research November 2000), Melatonin Agonist E (Chem. Pharm. Bull. (Tokyo) February 2002) Melatonin Agonist F (Reprod. Nutr. Dev. May 1999), Melatonin Agonist G (J. Med. Chem. October 1993), Melatonin Agonist H (Famaco March 2000), Melatonin Agonist I (J. Med. Chem. March 2000), Melatonin Analog J (Bioorg. Med. Chem. Lett. March 2003), Melatonin Analog K (MedAd News September 2001), Melatonin Analog L, AH-001, GG-012, enol-3-IPA, ML-23, SL-18.1616, IP-100-9, melatonin low-dose B, sleep inducing peptide A, orosmelatonin, AH-017, AH-002, IP-101, 5-hydroxy-N-acetyl-tryptamine (NAT), 5-methoxy-N-bu-tanoyltryptamine (bMT), prazosin, phenylmelatonin, seradrene, β-methyl-6-chloromelatonin, 5-hydroxyethoxy-N-acetyltryptamine (5-HEAT), 8-methoxy-2-propionamidotetralin, PD-6735, seroctin, N-[2-(5-methoxy-2-phenylfuro[2,3-b]pyridin-3-yl)ethyl]acetamide, N-[2-(5-methoxy-2-phenylfuro[2,3-c]pyridin-3-yl)ethyl]acetamide, N-[(±)-2-(7-methoxy-1,2,3,4-tetrahydro-1-naphthyl)ethyl]cyclopropyl-carboxamide, N-[2-(7-methoxy-1-naphthyl)ethyl]acetamide, N-acetyl-4-aminomethyl-6-methoxy-9-methyl-1,2,3,4-tetrahydrocarbazole (AMMTC), 3-(2-aminopropyl)indole, 6-chloromelatonin, 2,3-dihydromelatonin, 6-chloro-2,3-dihydromelatonin, N-acetyl-N'-formyl-5-methoxykynurenamine, 6-methoxybenzoxazolinone, or a pharmaceutically acceptable salt, solvate, clathrate, polymorph, or co-crystal thereof. See e.g., Tuma J, et al., Chronobiol Int. 18(5):781-99 (2001); Conway S, et al., Biochem Biophys Res Commun. 282(5):1229-36 (2001); Weibel Van Reeth O, et al., Am J Physiol Regul Integr Comp Physiol. 280(5):R1582-91 (2001); Weibel L, et al., Brain Res. 880(1-2):207-11 (2000); Ting N, et al., Naunyn Schmiedebergs Arch Pharmacol. 361(3):327-33 (2000); Loo H, et al., Encephale. 29(2):165-71 (2003); Millan M J, et al., Pharmacol Exp Ther. 306(3):954-64 (2003); Descamps-Francois C, et al., J Med Chem. 46(7):1127-9 (2003); Loo H, et al., Int Clin Psychopharmacol. 17(5):239-47 (2002); Nickelsen T, et al., Chronobiol Int. 19(5):915-36 (2002); Mohamed Naguib, et al., Anesth Analg 97:763-768 (2003); Vachharajani N N, et al., J Pharm Sci. 92(4):760-72 (2003); Mattson R J, et al., Bioorg Med Chem Lett. 13(6):1199-202 (2003); Patel R N, Curr Opin Biotechnol. 12(6):587-604 (2001); Uchikawa O, et al., J Med Chem. 45(19):4222-39 (2002); Barchas et al. Nature 1967, 214, 919; Kato, K. et al. Int. J. Neuropsychopharmacol. 2000, 3(Suppl. 1): Abst P.03.130; see also abstracts P.03.125 and P.03.127); Loo, H.; Hale, A., D'haenen, H. Int. Clin. Psychopharmacol. 2002, 17, 239-47; Nickelsen T, Samel A, Vejvoda M, Wenzel J, Smith B, Gerzer R. Chronobiol Int. 2002, 19, 915-36; Missbach, M.; Jagher, B.; Sigg, I.; Nayeri, S.; Carlberg, C.; Wiesenberg, I. J. Biol. Chem. 1996, 271, 13515-22; Wisenberg, I.; Missbach, M.; Kahlen, J.-P.; Schrader, M.; Carlberg, C. Nuc. Acids Res. 1995, 23, 327-333; Beresford, I. J.; Browning, C; Starkey, S. J.; Brown, J; Foord, S. M.; Coughlan, J; North, P. C.; Dubocovich, M. L.; Hagan, R. M.; J. Pharmacol. Exp. Ther. 1998, 285, 1239-1245 and Cutler, D. J.; Beresford, I. J. M.; Mason, R. Pharmacologist 1997, 39, 118; Depres-Brummer P, Metzger G, Levi F. Eur. J. Pharmacol. 1998, 347, 57-66 and Koster-van Hoffen, G. C.; Mirmiran, M.; Bos, N. P.; Witting, W.; Delagrange, P.; Guardiola-Lemaitre, B. Neurobiol Aging. 1993, 14, 565-9; Neuropharmacology July 2000; Naunyn Schmiedebergs Arch. 6/03; Vachharajani, N. N.; Yeleswaram, K.; Boulton, D. W. J. Pharm. Sci. 2003, 92, 760-72; Drugs R&D 2003, Adis R&D December 2002; Decision Resources October 1996; Dubocovich, M. L. J. Pharmacol. Exp. Ther. 1988, 246, 902; Beresford, I. J.; Harvey, F. J.; Hall, D. A.; Giles, H. Biochem Pharmacol. 1998, 56, 1167-74; IMSWorld R&D Focus August 2002; Pharmaprojects August 1998; Chem. Pharm. Bull. (Tokyo) January 2002; J. Pineal Research November 2000; Chem. Pharm. Bull. (Tokyo) February 2002; Reprod. Nutr. Dev.

May 1999; J. Med. Chem. October 1993; Famaco March 2000; J. Med. Chem. March 2000; Bioorg. Med. Chem. Lett. March 2003; MedAd News September 2001; Drijfhout, W. J. et al. Eur. J. Pharmacol. 1999, 382, 157-66; Drijfhout, W. J. et al. Eur. J. Pharmacol. 1999, 382, 157-66; Buzzell, G. R.; Menendez-Pelaez, A.; Troiani, M. E.; McNeill, M. E.; Reiter, R. J. J. Pineal. Res. 1990, 8, 229-35 and Nordio, M.; Vaughan, M. K.; Zisapel, N.; Migliaccio, S.; van Jaarsveld, A.; Reiter, R. J. Proceedings of the Society for Experimental Biology and Medicine 1989, 191, 321-325; Shah, J.; Langmuir, V.; Gupta, S. K. J Clin. Pharmacol. 1999, 39, 606-612. The above references are incorporated herein in their entirety.

In certain embodiments, the melatonin analog may also be as described in WO9517405; EP0447285; EP0527687; EP0530087; EP0591057; U.S. Pat. Nos. 6,638,966; 6,552,064; 6,310,085; 5,985,293; 5,939,084; 4,997,845; Ucar et al., J. Med. Chem., 1998, 41, 1138-1145; and Garratt et al., J. Med. Chem., 2000, 43, 1050-1061, the contents of which are incorporated herein in their entirety.

In certain aspects of the present invention, compositions comprising melatonin, an AANAT enhancer, an ASMT enhancer, a Per1 enhancer, a Bmal1 inhibitor, and/or a CLOCK enhancer may be administered to inhibit cholangiocyte proliferation or cholangiocarcinoma growth.

AANAT (aralkylamine N-acetyltransferase) belongs to the acetyltransferase superfamily. It is the penultimate enzyme in melatonin synthesis and controls the night/day rhythm in melatonin production in the vertebrate pineal gland. Melatonin is essential for the function of the circadian clock that influences activity and sleep. This enzyme is regulated by cAMP-dependent phosphorylation that promotes its interaction with 14-3-3 proteins and thus protects the enzyme against proteasomal degradation. This gene may contribute to numerous genetic diseases such as delayed sleep phase syndrome. Alternatively spliced transcript variants encoding different isoforms have been found for this gene (Genbank IDs of two human variants: NM_001088.2 and NM_001166579.1)

BMAL1 (ARNTL) is a basic-helix-loop-helix PAS (bHLH-PAS) domain containing protein that forms a heterodimer with a second bHLH-PAS protein, Clock, or its ortholog, Npas2. This complex binds to E-box response elements in promoter regions of many genes including those encoding the Period (Per1, Per2, Per3) and Cryptochrome (Cry1 and Cry2) proteins. These repressor proteins are translated, and bind in a complex with casein kinase 1ε (Csnk1e) and 1δ (Csnk1d). Next, the entire complex translocates to the nucleus, where it interacts with the Arntl/Clock heterodimer to inhibit its transactivation. This hypothesis is supported by the observation that point mutants in the Arntl or Clock render them resistant to interaction and repression by Cryptochromes. Transcription of Period and Cryptochrome genes, therefore, is inhibited, the protein levels of Period and Cryptochrome genes drop, and eventually repression is relieved to allow their transcription to build up again. This process occurs with a period length of approximately 24 hours. For example, human gene variants may be represented by Genbank IDs NM_001030272.1, NM_001030273.1, and NM_001178.4.

Period circadian protein homolog 1 (PER1) is a protein that in humans is encoded by the PER1 gene (human PER1 mRNA Genbank ID: NM_002616). This gene is a member of the Period family of genes and is expressed in a circadian pattern in the suprachiasmatic nucleus, the primary circadian pacemaker in the mammalian brain. Genes in this family encode components of the circadian rhythms of locomotor activity, metabolism, and behavior. Circadian expression in the suprachiasmatic nucleus continues in constant darkness, and a shift in the light/dark cycle evokes a proportional shift of gene expression in the suprachiasmatic nucleus. The specific function of this gene is not yet known. Alternative splicing has been observed in this gene; however, these variants have not been fully described.

Circadian Locomotor Output Cycles Kaput, or CLOCK is a gene (human CLOCK mRNA Genbank ID: NM_004898) that encodes proteins regulating circadian rhythm. The CLOCK protein seems to affect both the persistence and length of the circadian cycle. CLOCK forms part of a basic-helix-loop-helix transcription factor. BMAL-1 dimerizes with CLOCK in vivo and transactivates gene expression of Period and Timeless in drosophila by binding to E-box elements in their promoters. BMAL1-CLOCK also regulates Cryptochrome genes (e.g. Cry1, Cry2) and Period genes (e.g. Per1, Per2, Per3) in mammals. The BMAL-CLOCK complex itself is regulated by the expression of Per and Cry genes.

II. Cholangiocyte Pathological Conditions

In certain aspects of the invention, methods and compositions may be provided for treating or diagnosing cholangiocyte pathological conditions, including cholangiocarcinoma, cholangiopathy, or biliary hyperplasia. In a further aspect, the condition may be bile duct damage or loss having a decreased number of cholangiocytes, for example, from increased apoptosis of cholangiocytes. In some aspects the cholangiocyte pathological condition is a disorder associated with obstruction of a bile duct, such as by a stone, a tumor, or atresia of the bile duct.

Cholangiocytes are the epithelial cells of the bile duct. They are cuboidal epithelium in the small interlobular bile ducts, but become columnar and mucus secreting in larger bile ducts approaching the porta hepatis and the extrahepatic ducts.

In the healthy liver, cholangiocytes contribute to bile secretion via net release of bicarbonate and water. Several hormones and locally acting mediators are known to contribute to cholangiocyte fluid/electrolyte secretion. These include secretin, acetylcholine, ATP, and bombesin.

Cholangiocytes act through bile-acid independent bile flow, which is driven by the active transport of electrolytes; as opposed to hepatocytes, which secrete bile though bile-acid dependent bile flow which is coupled to canalicular secretion of bile acids via ATP-driven transporters, which results in passive transcellular and paracellular secretion of fluid and electrolytes through an osmotic effect.

Importantly, cholangiocytes are the target of disease in a variety of conditions often known as "cholangiopathies." These diseases include primary biliary cirrhosis, primary sclerosing cholangitis, AIDS cholangiopathy, disappearing bile duct syndromes, Alagille's syndrome, cystic fibrosis, and biliary atresia. As a group, cholangiopathies account for approximately 18% of adult liver transplantations and the majority of pediatric liver transplantations.

Cholestasis is a condition where bile cannot flow from the liver to the duodenum. The two basic distinctions are an obstructive type of cholestasis where there is a mechanical blockage in the duct system such as can occur from a gallstone or malignancy and metabolic types of cholestasis, which are disturbances in bile formation that can occur because of genetic defects or acquired as a side effect of many medications.

Cholangiocarcinoma is a cancer of the bile ducts, which drain bile from the liver into the small intestine. Other biliary tract cancers include pancreatic cancer, gall bladder cancer, and cancer of the ampulla of Vater. Cholangiocarcinoma is a relatively rare adenocarcinoma (glandular cancer), with an annual incidence of 1-2 cases per 100,000 in the Western world, but rates of cholangiocarcinoma have been rising worldwide over the past several decades.

Prominent symptoms of cholangiocarcinoma include abnormal liver function tests, abdominal pain, jaundice, weight loss, and sometimes generalized itching, fever, or changes in stool or urine color. The disease is diagnosed through a combination of blood tests, imaging, endoscopy, and sometimes surgical exploration. Cholangiocarcinoma is often in an advanced stage by the time symptoms develop, which may limit treatment options. Known risk factors for cholangiocarcinoma include primary sclerosing cholangitis (an inflammatory disease of the bile ducts), congenital liver malformations, infection with the parasitic liver flukes *Opisthorchis viverrini* or *Clonorchis sinensis*, and exposure to Thorotrast (thorium dioxide), a chemical formerly used in medical imaging. However, most patients with cholangiocarcinoma have no specific risk factors.

Cholangiocarcinoma is considered to be an incurable and rapidly lethal disease unless all of its tumors can be fully resected (cut out surgically). There is no potentially curative treatment except surgery, but unfortunately most patients have advanced and inoperable disease at the time of diagnosis. Patients with cholangiocarcinoma are generally managed, though never cured, with chemotherapy or radiation therapy as well as palliative care measures, and these are also used as adjuvant therapies post-surgically in cases where resection has been successful. Some areas of ongoing medical research in cholangiocarcinoma include the use of newer targeted therapies (such as erlotinib) or photodynamic therapy for treatment, and the concentration of byproducts of cancer stromal cell formation in the blood for diagnosis.

Cholangiocarcinoma can affect any area of the bile ducts, either within or outside the liver. Tumors occurring in the bile ducts within the liver are referred to as intrahepatic, those occurring in the ducts outside the liver are extrahepatic; and tumors occurring at the site where the bile ducts exit the liver may be referred to as perihilar. A cholangiocarcinoma occurring at the junction where the left and right hepatic ducts meet to form the common bile duct may be referred to eponymously as a Klatskin tumor.

Although cholangiocarcinoma is known to be an adenocarcinoma of the epithelial cells lining the biliary tract, the actual cell of origin is unknown, although recent evidence has suggested that it may arise from a pluripotent hepatic stem cell. Cholangiocarcinoma is thought to develop through a series of stages—from early hyperplasia and metaplasia, through dysplasia, to the development of frank carcinoma—in a process similar to that seen in the development of colon cancer. Chronic inflammation and obstruction of the bile ducts, and the resulting impaired bile flow, are thought to play a role in this progression.

III. Diagnosis of Cholangiocarcinoma

In a certain aspect, there may be provided methods involving detecting cholangiocarcinoma, for example, by detection of melatonin in a bile sample or by detection of melatonin modulator genes, such as AANAT, ASMT, Per1, BMAL1, or CLOCK. A bile sample may be a sample comprising bile. The bile sample may be obtained by any method known to those of ordinary skill in the art, such as via ERCP. For example, a melatonin level of at least, about, or at most 2, 3, 4, 5, 6, 7, 8, 9, 10, 11, 12, 13, 14, 15, 16, 17, 18, 19, 20 fold lower than a reference level may be indicative of a higher risk of having or developing cholangiocarcinoma.

A sample of bile (a digestive fluid) may be obtained. This can be done using any methods known in the art, including gallbladder surgery or a scope procedure called endoscopic retrograde cholangiopancreatography (ERCP).

Endoscopic retrograde cholangiopancreatography (ERCP) is a technique that may combine the use of endoscopy and fluoroscopy to diagnose and treat certain problems of the biliary or pancreatic ductal systems. Through the endoscope, the physician may see the inside of the stomach and duodenum, and inject dyes into the ducts in the biliary tree and pancreas so they can be seen on x-rays. ERCP has been used primarily to diagnose and treat conditions of the bile ducts, including gallstones, inflammatory strictures (scars), leaks (from trauma and surgery), and cancer. ERCP can be performed for diagnostic and therapeutic reasons.

The bile sample may be fresh, stored, or cultured. The bile sample may have a volume of at least, about or at most 1, 2, 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, 1000 μl, 2, 3, 4, 5, 6, 7, 8, 9, 10, 20, 30, 40, 50, 60, 70, 80, 90, 100 ml or any intermediate ranges or values.

IV. Therapeutic Applications and Pharmaceutical Preparations

Therapeutic applications involving the use of melatonin signaling modulators (including or excluding melatonin) may be provided for treating cholangiocyte pathological conditions.

"Treatment" and "treating" refer to administration or application of a drug or therapy (such as protein, nucleic acid, gene therapy, or cell-based therapy) to a subject or performance of a procedure or modality on a subject for the purpose of obtaining a therapeutic benefit of a disease or health-related condition.

The term "therapeutic benefit" used throughout this application refers to anything that promotes or enhances the well-being of the subject with respect to the medical treatment of his condition. This includes, but is not limited to, a reduction in the frequency or severity of the signs or symptoms of a disease.

A "disease" or "health-related condition" can be any pathological condition of a body part, an organ, or a system resulting from any cause, such as infection, genetic defect, trauma, and/or environmental stress. The cause may or may not be known. Examples of such conditions include cancer and diabetes.

"Prevention" and "preventing" are used according to their ordinary and plain meaning to mean "acting before" or such an act. In the context of a particular disease or health-related condition, those terms refer to administration or application of an agent, drug, or remedy to a subject or performance of a procedure or modality on a subject for the purpose of blocking the onset of a disease or health-related condition.

Pharmaceutical compositions of the present invention comprise an effective amount of one or more cell or gene delivery compositions or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference).

The actual required amount of a composition administered to a subject, such as a patient with a disease, can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 microgram/kg/body weight to about 500 milligram/kg/body weight, etc., can be administered.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions may be administered in the form of injectable compositions either as liquid solutions or suspensions; solid forms suitable for solution in, or suspension in, liquid prior to injection may also be prepared. These preparations also may be emulsified. A exemplary composition for such purpose may comprise a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations that may be suitable for oral administration are provided. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders.

The therapeutic compositions may include classic pharmaceutical preparations. Administration of therapeutic compositions according to the present invention will be via any common route so long as the target tissue is available via that route. This includes oral, nasal, buccal, rectal, vaginal or topical. Topical administration may be particularly advantageous for the treatment of skin cancers, to prevent chemotherapy-induced alopecia or other dermal hyperproliferative disorder. Alternatively, administration may be by orthotopic, intradermal, subcutaneous, intramuscular, intraperitoneal, or intravenous injection. Such compositions would normally be administered as pharmaceutically acceptable compositions that include physiologically acceptable carriers, buffers or other excipients. In further aspects, aerosol delivery can be used. Volume of the aerosol may be between about 0.01 ml and 0.5 ml. Administration may be directly into the biliary tree such as in conjunction with ERCP.

Certain aspects of the present invention also contemplate methods of preventing, inhibiting, or treating bile duct diseases or conditions in a subject by administration a melatonin signaling modulator-based therapeutic agent. Aspects of the invention also include the use of the methods and compositions of the invention in combination with other therapies, as discussed in greater detail below.

V. Combination Therapy

It is an aspect of this invention that the claimed methods for treating cholangiocarcinoma in a subject can be used in combination with another agent or therapy method. In certain embodiments, the other agent or therapy is another anti-cancer agent or anti-cancer therapy. In a particular embodiment, the melatonin or melatonin signaling modulators may be administered in combination with a chemotherapy.

Treatment with the claimed melatonin signaling modulator may precede or follow the other therapy method by intervals ranging from minutes to weeks. In embodiments where another agent is administered, one would generally ensure that a significant period of time did not expire between the time of each delivery, such that the agents would still be able to exert an advantageously combined effect on the cell. For example, it is contemplated that one may administer two, three, four or more doses of one agent substantially simultaneously (i.e., within less than about a minute) with the therapeutic agents of the present invention. In other aspects, a therapeutic agent or method may be administered within about 1 minute to about 48 hours or more prior to and/or after administering a melatonin signaling modulator-based therapeutic agent or agents of the present invention, or prior to and/or after any amount of time not set forth herein. In certain other embodiments, a melatonin signaling modulator-based therapeutic agent of the present invention may be administered within from about 1 day to about 21 days prior to and/or after administering another therapeutic modality, such as surgery or gene therapy. In some situations, it may be desirable to extend the time period for treatment significantly, however, where several weeks (e.g., about 1 to 8 weeks or more) lapse between the respective administrations. Various combinations may be employed, the claimed a melatonin signaling modulator-based agent is derivative is "A" and the secondary agent, which can be any other therapeutic agent or method, is "B":

A/B/A B/A/B B/B/A AJAJB A/B/B BIAJA A/B/B/B

B/A/B/B B/B/B/A B/B/A/B A/A/B/B A/B/A/B A/B/B/A

B/B/A/A B/A/B/A B/A/A/B A/A/A/B B/A/A/A A/B/A/A

A/A/B/A

Administration of the a melatonin signaling modulator-based therapeutic agents of the present invention to a patient will follow general protocols for the administration of chemotherapeutics, taking into account the toxicity, if any, of these agents. It is expected that the treatment cycles would be repeated as necessary. It also is contemplated that various standard therapies, as well as surgical intervention, may be applied in combination with the therapeutic. These therapies include but are not limited to additional drug therapy, chemotherapy, additional radiotherapy, immunotherapy, gene therapy and surgery.

In certain aspects, therapy further includes modification of the light-dark cycle of the subject. For example, a subject, such as a subject with cholangiocarcinoma or primary sclerosing cholangitis, may be placed on a regimen of a certain number of hours of reduced illumination (or complete darkness) at a defined interval (for example, per day, per week, per month or any known schedule). Production of melatonin by the pineal gland is inhibited by light and permitted by darkness. For example, the light to be reduced may be a light with a wavelength of up to about 530, 520, 510, 500, 490, 480, 470, 460, 450, 440 430, 420, 410 nm or any intermediate values or ranges. Particularly, the light may be blue light (for example, about 460 to about 480 nm) that suppresses melatonin, the level of which increases with increased light intensity and length of exposure. Kayumov et al. (2005) showed that light containing only wavelengths greater than 530 nm does not suppress melatonin in bright-light conditions. Use of blue-blocking goggles may be utilized to establish elevated melatonin levels in patients allowing them to be ambulatory.

In another aspect, a subject in need of reduced melatonin signaling, for example, patients with ductopenic disease, may be exposed to increased illumination (light) at a defined interval (for example, per day, per week, per month or any known schedule). Exposure to light inhibits melatonin production.

A. Chemotherapy

Cancer therapies also include a variety of combination therapies with both chemical and radiation based treatments. Chemotherapies include, but are not limited to, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP 16), tamoxifen, raloxifene, estrogen receptor binding agents, taxol, gemcitabien, navelbine, farnesyl-protein transferase inhibitors, transplatinum, 5-fluorouracil, vincristin, vinblastin and methotrexate, or any analog or derivative variant of the foregoing. In a particular aspect, the chemotherapy may be 5-fluorouracil and/or gemcitabien.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells. The terms "contacted" and "exposed," when applied to a cell, are used herein to describe the process by which a therapeutic construct and a chemo therapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

C. Immunotherapy

Immunotherapeutics, generally, rely on the use of immune modulators, immune effector cells and molecules to cure or palliate disease. In certain embodiments, immune modulators, immune effector cells and molecules target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionucleotide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcino embryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and pi 55.

D. Nucleic Acid-Based Therapy

In yet another embodiment, the secondary treatment is an additional gene therapy in which a therapeutic polynucleotide is administered before, after, or at the same time as the nucleic acid composition of the present invention. Delivery of the a melatonin signaling modulator-based therapeutic agent in conjunction with a vector encoding a gene product will have a combined therapeutic effect such as an anti-hyperproliferative effect on target tissues.

RNA interference (RNAi) is a powerful gene-silencing process that holds great promise in the field of cancer therapy. The evolving understanding of the molecular pathways important for carcinogenesis has created opportunities for cancer therapy employing RNAi technology to target the key molecules within these pathways. Major targets for siRNA therapy include oncogenes and genes that are involved in angiogenesis, metastasis, survival, antiapoptosis and resistance to chemotherapy.

Many gene products involved in carcinogenesis have already been explored as targets for RNAi intervention, and RNAi targeting of molecules crucial for tumor-host interactions and tumor resistance to chemo- or radiotherapy has also been investigated. In most of these studies, the silencing of critical gene products by RNAi technology has generated significant antiproliferative and/or proapoptotic effects in cell-culture systems or in preclinical animal models.

siRNA can be introduced into the cells by using either chemically synthesized siRNA oligonucleotides (oligos), or vector-based siRNA (shRNA), which allows long lasting and more stable gene silencing. Nanoparticles and liposomes are commonly used carriers, delivering the siRNA with better transfection efficiency and protecting it from degradation. In combination with standard chemotherapy, siRNA therapy can also reduce the chemoresistance of certain cancers, demonstrating the potential of siRNA therapy for treating many malignant diseases.

E. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

VI. Nucleic Acids

Aspects of the invention include introducing into a cell with an exogenous expression construct comprising at least a first region that is a nucleic acid sequence encoding a melatonin signaling modulator operatively linked to a first promoter sequence. The melatonin signaling modulator may be constitutively active or signaling defective. In other aspects, expression construct may include one or more additional nucleic acid sequences, such as additional reporters, additional coding regions, or additional promoters The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring or derivatized purine or pyrimidine base found in DNA (e.g., an adenine "A," a guanine "G," a thymine "T" or a cytosine "C") or RNA (e.g., an A, a G, an uracil "U" or a C). The term "nucleic acid" encompasses the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length.

These definitions generally refer to a single-stranded molecule, but in specific embodiments will also encompass an additional strand that is partially, substantially or fully complementary to the single-stranded molecule. Thus, a nucleic acid may encompass a double-stranded molecule or a triple-stranded molecule that comprises one or more complementary strand(s) or "complement(s)" of a particular sequence comprising a molecule A. Inhibitory Nucleic Acids or Nucleic Acid Analogs In certain aspects of the present invention, inhibitors for melatonin signaling modulators may be used for treating of a subject. For example, an AANAT-specific inhibitory nucleic acid may be used. Examples of an inhibitory nucleic acid include but are not limited to siRNA (small interfering RNA), short hairpin RNA (shRNA), double-stranded RNA, an antisense oligonucleotide, a ribozyme and a nucleic acid encoding thereof. An inhibitory nucleic acid may inhibit the transcription of a gene or prevent the translation of a gene transcript in a cell. An inhibitory nucleic acid may be from 16 to 1000 nucleotides long, and in certain embodiments from 18 to 100 nucleotides long. Particularly, an inhibitory nucleic acid or analog may be capable of decreasing the expression of a target gene, such as AANAT, by at least 10%, 20%, 30%, or 40%, more particularly by at least 50%, 60%, or 70%, and most particularly by at least 75%, 80%, 90%, 95% or more or any ranges in between the foregoing.

Inhibitory nucleic acids are well known in the art. For example, siRNA and double-stranded RNA have been described in U.S. Pat. Nos. 6,506,559 and 6,573,099, as well as in U.S. Patent Publications 2003/0051263, 2003/0055020, 2004/0265839, 2002/0168707, 2003/0159161, and 2004/0064842, all of which are herein incorporated by reference in their entirety.

For example, the inhibitory nucleic acid may be siRNA. siRNA can be obtained from commercial sources, natural sources, or can be synthesized using any of a number of techniques well-known to those of ordinary skill in the art. For example, commercial sources of predesigned siRNA include Invitrogen's Stealth™ Select technology (Carlsbad, Calif.), Ambion® (Austin, Tex.), and Qiagen® (Valencia, Calif.). An inhibitory nucleic acid that can be applied in the compositions and methods of the present invention may be any nucleic acid sequence that has been found by any source to be a validated down-regulator of a corresponding gene.

Certain embodiments of the present invention pertain to methods of inhibiting expression of a melatonin modulator gene in a cell by introduction of inhibitory nucleic acids or analogs into the cell. Introduction of nucleic acids or analogs into cells can be achieved by methods known in the art, including for example, microinjection, electroporation, or transfection of a vector comprising a nucleic acid from which the siRNA can be transcribed. Alternatively, an inhibitory nucleic acid or analog can be directly introduced into a cell in a form that is capable of binding to target melatonin modulator mRNA transcripts. To increase durability and membrane-permeability the inhibitory nucleic acid or analog may be combined or modified with liposomes, poly-L-lysine, lipids, cholesterol, lipofectine or derivatives thereof.

In a particular aspect, the inhibitory nucleic acid analog may be an antisense morpholino molecule. A Morpholino is a molecule in a particular structural family that is used to modify gene expression. Morpholino oligomers (oligos) are an antisense technology used to block access of other molecules to specific sequences within nucleic acid. Morpholinos block small (for example, ~25 bases) regions of the base-pairing surfaces of ribonucleic acid (RNA). Morpholinos are synthetic molecules that are the product of a redesign of natural nucleic acid structure. They bind to complementary sequences of RNA by standard nucleic acid base-pairing. Structurally, the difference between Morpholinos and DNA is that while Morpholinos have standard nucleic acid bases, those bases are bound to morpholino rings instead of deoxyribose rings and linked through phosphorodiamidate groups instead of phosphates. Morpholinos do not degrade their target RNA molecules, unlike many antisense structural types (e.g., phosphorothioates, siRNA). Instead, Morpholinos act by "steric blocking", binding to a target sequence within an RNA and simply getting in the way of molecules that might otherwise interact with the RNA.

For a Morpholino to be effective, it must be delivered past the cell membrane into the cytosol of a cell. Once in the cytosol, Morpholinos freely diffuse between the cytosol and nucleus, as demonstrated by the nuclear splice-modifying activity of Morpholinos observed after microinjection into the cytosol of cells. Any methods known in the art may be used for delivery of Morpholino to the subject.

B. Exogenous Expression Cassettes

In certain aspects of the present invention, genes involved in melatonin signaling may be delivered to a subject in an exogenous expression cassette, such as AANAT expression cassette. The expression cassette may be comprised in a vector or a gene delivery vehicle.

The term "vector" is used to refer to a carrier into which a nucleic acid sequence can be inserted for introduction into a cell where it can be expressed and/or replicated. The term "expression vector" or "nucleic acid vector" refers to a nucleic acid containing a nucleic acid sequence or "cassette" coding for at least part of a nucleic acid sequence, also referred to herein as a gene, product capable of being transcribed and "regulatory" or "control" sequences, which refer to nucleic acid sequences necessary for the transcription and possibly translation of an operably linked coding sequence in a particular host cell. In addition to control sequences that govern transcription and translation, the expression vectors may contain nucleic acid sequences that serve other functions as well.

The term "promoter" is used interchangeably with "promoter element" and "promoter sequence." Likewise, the term "enhancer" is used interchangeably with "enhancer element" and "enhancer sequence." A promoter, enhancer, or repressor, is said to be "operably linked" to a nucleic acid or transgene, such as a nucleic acid encoding a recombinant seven transmembrane G-protein associated receptor, when such element(s) control(s) or affect(s) nucleic acid or transgene transcription rate or efficiency. For example, a promoter sequence located proximally to the 5' end of a transgene coding sequence is usually operably linked with the transgene. As used herein, term "regulatory elements" is used interchangeably with "regulatory sequences" and refers to promoters, enhancers, polyadenylation sites and other expression control elements, or any combination of such elements.

A. Promoters

Promoters are positioned 5' (upstream) to the genes that they control. Many eukaryotic promoters contain two types of recognition sequences: TATA box and the upstream promoter elements. The TATA box, located 25-30 bp upstream of the transcription initiation site, is thought to be involved in directing RNA polymerase II to begin RNA synthesis at the correct site. In contrast, the upstream promoter elements determine the rate at which transcription is initiated. These elements can act regardless of their orientation, but they must be located within 100 to 200 bp upstream of the TATA box.

Enhancer elements can stimulate transcription up to 1000-fold from linked homologous or heterologous promoters. Enhancer elements often remain active even if their orientation is reversed (Li et al, 1990). Furthermore, unlike promoter elements, enhancers can be active when placed downstream from the transcription initiation site, e.g., within an intron, or even at a considerable distance from the promoter (Yutzey et al, 1989).

As is known in the art, some variation in this distance can be accommodated without loss of promoter function. Similarly, the positioning of regulatory elements with respect to the transgene may vary significantly without loss of function. Multiple copies of regulatory elements can act in concert. Typically, an expression vector comprises one or more enhancer sequences followed by, in the 5' to 3' direction, a promoter sequence, all operably linked to a transgene followed by a polyadenylation sequence. A "promoter" sequence is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence. Together, an appropriate promoter or promoter/enhancer combination, and a gene of interest, comprise an expression cassette. One or more expression cassettes may be present in a given nucleic acid vector or expression vector. In certain aspects, one expression cassette may encode a transactivator that interacts with a promoter of a second expression cassette. The one or more expression cassettes may be present on the same and/or different expression vector.

A promoter may be one naturally associated with a gene or sequence, as may be obtained by isolating a portion the 5' non-coding sequences located upstream of the coding segment or exon. Such a promoter can be referred to as "endogenous." Similarly, an enhancer may be one naturally associated with a nucleic acid sequence, located either downstream or upstream of that sequence. Alternatively, certain advantages will be gained by positioning the nucleic acid segment under the control of a recombinant or heterologous promoter, which refers to a promoter that is not normally associated with a nucleic acid sequence in its natural environment.

In certain aspect of the invention a heterologous promoter may be a chimeric promoter, where elements of two or more endogenous, heterologous or synthetic promoter sequences are operatively coupled to produce a recombinant promoter. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Such promoters may be used to drive reporter expression, which include, but are not limited to GPCRs, β-galactosidase or luciferase to name a few. Furthermore, it is contemplated the control sequences that direct transcription and/or expression of sequences within non-nuclear organelles such as mitochondria, chloroplasts, and the like, can be employed as well.

B. Internal Ribosome Entry Sites (IRES)

In certain embodiments of the invention, internal ribosome entry site (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991) and further sequences as well as modified versions are envisioned in this application for invention. IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (U.S. Pat. Nos. 5,925,565 and 5,935,819; and PCT application PCT/US99/05781) and are envisioned in this application for invention. The order (upstream or downstream of the IRES) of the reporter and gene(s) of interest is not important for the invention. More than one gene of interest may be linked.

C. Selectable Markers

In certain embodiments of the invention, a nucleic acid construct of the present invention may be isolated or selected for in vitro or in vivo by including a selectable marker in the expression vector. Such selectable markers would confer an identifiable characteristic to the cell permitting easy identification, isolation and/or selection of cells containing the expression vector. A positive selectable marker is one in which the presence of the marker allows for its selection, while a negative selectable marker is one in which its presence prevents its selection. An example of a positive selectable marker is a drug resistance marker. Examples of selectable and screenable markers are well known to one of skill in the art.

D. Other Elements of Expression Cassettes

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (Chandler et al, 1997).

One may include a polyadenylation signal in the expression construct to effect proper polyadenylation of the transcript. The nature of the polyadenylation signal is not believed to be crucial to the successful practice of the invention, and/or any such sequence may be employed. Specific embodiments include the SV40 polyadenylation signal and/or the bovine growth hormone polyadenylation signal, convenient and/or known to function well in various target cells. Also contemplated as an element of the expression cassette is a transcriptional termination site. These elements can serve to enhance message levels and/or to minimize read through from the cassette into other sequences. The vectors or constructs of the present invention may comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, the terminator may comprise a signal for the cleavage of the RNA, and it is more specific that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

In order to propagate a vector in a host cell, it may contain one or more origins of replication sites (often termed "ori"), which is a specific nucleic acid sequence at which replication is initiated.

VII. Gene Delivery

Aspects of the invention include transferring into a cell an exogenous expression construct comprising a nucleic acid sequence encoding a melatonin signaling modulator. Techniques pertaining to the transfer of expression constructs into cells are well-known to those of ordinary skill in the art. Exemplary techniques are discussed below.

A. Viral Vectors

In certain embodiments of the present invention, transfer of an expression construct into a cell is accomplished using a viral vector. Techniques using "viral vectors" are well-known in the art. A viral vector is meant to include those constructs containing viral sequences sufficient to (a) support packaging of the expression cassette and (b) to ultimately express a recombinant gene construct that has been cloned therein.

In particular embodiments, the viral vector is a lentivirus vector. Lentivirus vectors have been successfully used in infecting stem cells and providing long term expression.

Another method for delivery of a nucleic acid involves the use of an adenovirus vector. Adenovirus vectors are known to have a low capacity for integration into genomic DNA. Adenovirus vectors result in highly efficient gene transfer.

Adenoviruses are currently the most commonly used vector for gene transfer in clinical settings. Among the advantages of these viruses is that they are efficient at gene delivery to both non-dividing and dividing cells and can be produced in large quantities. The vector comprises a genetically engineered form of adenovirus (Grunhaus et al, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range and high infectivity. A person of ordinary skill in the art would be familiar with experimental methods using adenoviral vectors.

The adenovirus vector may be replication defective, or at least conditionally defective, and the nature of the adenovirus vector is not believed to be crucial to the successful practice of the invention. The adenovirus may be of any of the 42 different known serotypes or subgroups A-F and other serotypes or subgroups are envisioned. Adenovirus type 5 of subgroup C is the starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector. Adenovirus growth and manipulation is known to those of skill in the art, and exhibits broad host range in vitro and in vivo. Modified viruses, such as adenoviruses with alteration of the CAR domain, may also be used. Methods for enhancing delivery or evading an immune response, such as liposome encapsulation of the virus, are also envisioned. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains two long terminal repeat (LTR) sequences present at the 5' and 3' ends of the viral genome. These contain strong promoter and enhancer sequences and are also required for integration in the host cell genome (Coffin, 1990).

In order to construct a retroviral vector, a nucleic acid encoding a nucleic acid or gene of interest is inserted into the viral genome in the place of certain viral sequences to produce a virus that is replication-defective. A person of ordinary skill in the art would be familiar with well-known techniques that are available to construct a retroviral vector. Adeno-associated virus (AAV) is an attractive vector system for use in the present invention as it has a high frequency of integration and it can infect nondividing cells, thus making it useful for delivery of genes into mammalian cells in tissue culture (Muzyczka, 1992). AAV has a broad host range for infectivity (Tratschin et al., 1984; Laughlin et al, 1986; Lebkowski et al, 1988; McLaughlin et al, 1988), which means it is applicable for use with the present invention. Details concerning the generation and use of rAAV vectors are described in U.S. Pat. Nos. 5,139,941 and 4,797,368, each incorporated herein by reference.

Recombinant AAV (rAAV) virus may be made by cotransfecting a plasmid containing the gene of interest flanked by the two AAV terminal repeats (McLaughlin et al, 1988; Samulski et al, 1989; each incorporated herein by reference) and an expression plasmid containing the wild-type AAV coding sequences without the terminal repeats, for example pIM45 (McCarty et al., 1991; incorporated herein by reference). A person of ordinary skill in the art would be familiar with techniques available to generate vectors using AAV virus.

Herpes simplex virus (HSV) has generated considerable interest in treating nervous system disorders due to its tropism for neuronal cells, but this vector also can be exploited for other tissues given its wide host range. Another factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc) makes it possible to control expression to a greater extent than in other systems. It also is an advantage that the virus has relatively few spliced messages, further easing genetic manipulations.

HSV also is relatively easy to manipulate and can be grown to high titers. Thus, delivery is less of a problem, both in terms of volumes needed to attain sufficient MOI and in a lessened need for repeat dosings. For a review of HSV as a gene therapy vector, see Glorioso et al. (1995). A person of ordinary skill in the art would be familiar with well-known techniques for use of HSV as vectors.

Vaccinia virus vectors have been used extensively because of the ease of their construction, relatively high levels of expression obtained, wide host range and large capacity for carrying DNA. Vaccinia contains a linear, double-stranded DNA genome of about 186 kb that exhibits a marked "A-T" preference. Inverted terminal repeats of about 10.5 kb flank the genome.

Other viral vectors may be employed as constructs. For example, vectors derived from viruses such as poxvirus may be employed. A molecularly cloned strain of Venezuelan equine encephalitis (VEE) virus has been genetically refined as a replication competent vaccine vector for the expression of heterologous viral proteins (Davis et al., 1996). Studies have demonstrated that VEE infection stimulates potent CTL responses and it has been suggested that VEE may be an extremely useful vector for immunizations (Caley et al., 1997). It is contemplated in the present invention, that VEE virus may be useful in targeting dendritic cells.

A polynucleotide may be housed within a viral vector that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

B. Non-Viral Gene Transfer

Several non-viral methods for the transfer of nucleic acids into cells also are contemplated by certain aspects of the present invention. These include calcium phosphate precipitation (Graham and Van Der Eb, 1973; Chen and Okayama, 1987; Rippe et al, 1990) DEAE-dextran (Gopal, 1985), electroporation (Tur-Kaspa et al, 1986; Potter et al, 1984), nucleofection (Trompeter et al, 2003), direct microinjection (Harland and Weintraub, 1985), DNA-loaded liposomes (Nicolau and Sene, 1982; Fraley et al, 1979) and lipofectamine-DNA complexes, polyamino acids, cell sonication (Fechheimer et al, 1987), gene bombardment using high velocity microprojectiles (Yang et al, 1990), polycations (Boussif et al, 1995) and receptor-mediated transfection (Wu and Wu, 1987; Wu and Wu, 1988). Some of these techniques may be successfully adapted for in vivo or ex vivo use. A person of ordinary skill in the art would be familiar with the techniques pertaining to use of non-viral vectors, and would understand that other types of non-viral vectors than those disclosed herein are contemplated by the present invention. In a further embodiment of the invention, the expression cassette may be entrapped in a liposome or lipid formulation. Liposomes are vesicular structures characterized by a phospholipid bilayer membrane and an inner aqueous medium. Multilamellar liposomes have multiple lipid layers separated by aqueous medium. Also contemplated is a gene construct complexed with Lipofectamine (Gibco BRL). One of ordinary skill in the art would be familiar with techniques utilizing liposomes and lipid formulations.

VIII. Kits

The present invention provides kits, such as diagnostic and therapeutic kits based on melatonin signaling modulators. For example, a kit may comprise one or more pharmaceutical compositions as described herein and optionally instructions for their use. Kits may also comprise one or more devices for accomplishing administration of such compositions. For example, a subject kit may comprise a pharmaceutical composition and catheter for accomplishing direct intraarterial injection of the composition into a cancerous tumor. In other embodiments, a subject kit may comprise pre-filled ampoules of a melatonin-specific antibody construct, optionally formulated as a pharmaceutical, or lyophilized, for use with a delivery device.

Kits may comprise a container with a label. Suitable containers include, for example, bottles, vials, and test tubes. The containers may be formed from a variety of materials such as glass or plastic. The container may hold a composition which includes an antibody that is effective for therapeutic or non-therapeutic applications, such as described above. The label on the container may indicate that the composition is used for a specific therapy or non-therapeutic application, and may also indicate directions for either in vivo or in vitro use, such as those described above. The kit of the invention will typically comprise the container described above and one or more other containers comprising materials desirable from a commercial and user standpoint, including buffers, diluents, filters, needles, syringes, and package inserts with instructions for use.

IX. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Melatonin Inhibits Cholangiocyte Proliferation by Down-Regulation of Clock Genes Cholangiocytes Express MT1 and MT2, CLOCK, BMAL1, CRY1 and PER1.

By immunohistochemistry in liver sections bile ducts from normal rats were weakly positive for MT1 (but not MT2), but showed strong immunoreactivity for both MT1 and MT2. Vascular endothelial cells and hepatocytes from normal rats did not stain for MT1 and MT2; immunoreactivity for MT2 (but not MT1) slightly increased in hepatocytes but not vascular cells from BDL rats. The expression of CLOCK and BMAL1 was virtually absent in normal bile ducts; however, immunoreactivity was observed in BDL bile ducts. Hepatocytes and vascular cells were from normal and BDL rats seemed negative for CLOCK and BMAL1. Normal bile ducts stained positively for PER1 and CRY1, whose expression seemed slightly increased in bile ducts from BDL rats. The immunoreactivity of PER1 and CRY1 seemed similar among hepatocytes from normal and BDL rats; vascular cells were positive for PER1 but not CRY1.

Figure 2A:
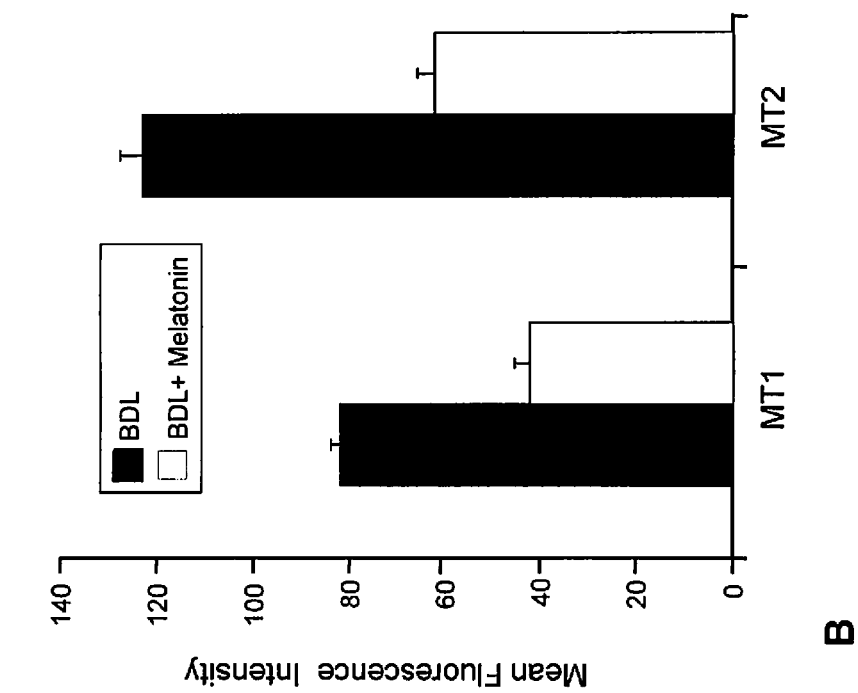
FIGS. 2A-2B [FIG. 2A] By real-time PCR, the mRNA expression of MT1 and MT2 increased in BDL compared to normal cholangiocytes, but decreased in purified cholangiocytes from BDL rats treated with melatonin in vivo compared to cholangiocytes from control BDL rats. Data are mean SEM of three evaluations. $^*p<0.05$ vs. the values of normal cholangiocytes. $^\#p<0.05$ vs. the values of BDL cholangiocytes from rats treated with regular tap water.
Figure 2B:
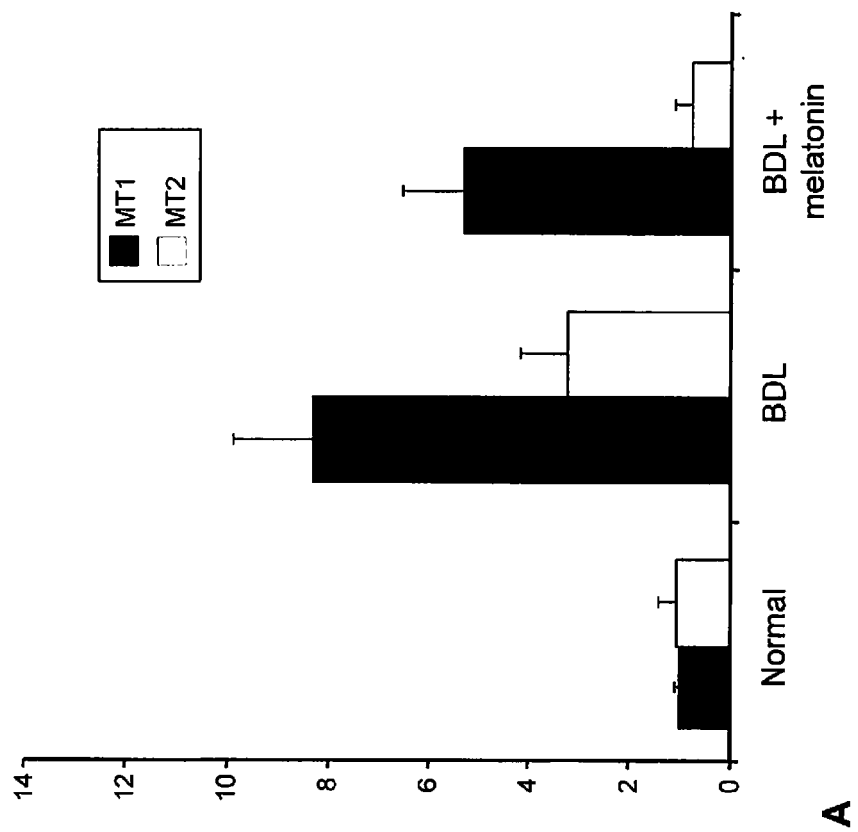

By real-time PCR (FIG. 1A), and FACS analysis (FIG. 1B), the expression of PER1, BMAL1, CRY1 and CLOCK: (i) increased in BDL compared to normal cholangiocytes; but (ii) decreased in cholangiocytes from normal and BDL rats treated in vivo with melatonin compared to control cholangiocytes. The mRNA expression of MT1 and MT2 increased in BDL compared to normal cholangiocytes (FIG. 2A). By both real-time PCR and FACS analysis, the expression of MT1 and MT2 decreased in cholangiocytes from BDL rats treated with melatonin in vivo compared to cholangiocytes from BDL rats treated with regular tap water (FIGS. 2A-2B).

Evaluation of Serum Levels of Melatonin, Transaminases, and Bilirubin Levels, Cholangiocyte Proliferation and Apoptosis.

There was approximately a 15-20% decrease of body weight in BDL compared to normal rats (Table 1). There was no difference in body weight between normal and BDL treated with melatonin compared to their corresponding control rats (Table 1). There was a decrease in liver to body weight ratio in BDL rats treated with melatonin compared to BDL control rats (Table 1). As shown in Table 1, the serum levels of melatonin of normal rats were similar to that of previous studies and increased following BDL (40), and after the administration of melatonin to normal and BDL rats (Table 1). In agreement with previous studies (3), the serum levels of transaminases increased in cholestatic BDL rats compared to normal rats and were decreased in both normal and BDL rats by the administration of melatonin (Table 1). The administration of melatonin to BDL rats decreased large BDM (bile duct mass) and the percentage of PCNA-positive large cholangiocytes (Table 2) compared to their corresponding control rats. Melatonin inhibition of biliary hyperplasia in BDL rats was associated with enhanced cholangiocyte apoptosis (Table 2). Melatonin had no effects in normal rats (Table 2). No morphological damage of kidney, heart, stomach, spleen and small and large intestine was observed in normal and BDL rats treated with melatonin (not shown).

TABLE 1

Evaluation of liver and body weight, liver to body weight ratio, and serum levels of melatonin, transaminases and bilirubin in the selected groups of animals.

| Groups | Liver weight (gm) | Body weight (gm) | Liver to body weight ratio | Melatonin serum (pg/ml) | SGPT (Units/L) | SGOT (Units/L) | Total bilirubin (mg/L) |
|---|---|---|---|---|---|---|---|
| X. Normal rats + tap water | 7.98 ± 0.7 (n = 5) | 190.4 ± 3.2 (n = 5) | 4.2 ± 0.4 (n = 5) | 45.5 ± 12.7 (n = 7) | 83.2 ± 14.8 (n = 7) | 194.5 ± 42.0 (n = 6) | <0.1 (n = 8) |
| XI. Normal rats + XII. tap water containing melatonin | 9.4 ± 0.4 (n = 5) | 206.6 ± 3.9 (n = 5) | 4.5 ± 0.2 (n = 5) | 140.2 ± 12.7 (n = 7) | 69.4 ± 45.9 (n = 7) | 143.0 ± 36.0 (n = 6) | <0.1 (n = 8) |
| XIII. BDL rats + tap water | 8.3 ± 0.2 (n = 15) | 145.6 ± 3.9 (n = 15) | 5.7 ± 0.1 (n = 15) | 117.6 ± 38.5 (n = 7) | 390.7 ± 107.0 (n = 6) | 1415.0 ± 325.8 (n = 6) | 12.4 ± 1.5 (n = 8) |
| XIV. BDL rats + XV. tap water containing melatonin | 6.7 ± 0.1 (n = 15) | 150.1 ± 7.9 (n = 15) | 4.5 ± 0.1 (n = 15) | 164.7 ± 66.8 (n = 7) | 210.8 ± 45.9 (n = 6) | 585.0 ± 162.4 (n = 6) | 7.3 ± 1.9 (n = 8) |

Data are mean ± SEM. BDL = bile duct ligation. SGOT = serum glutamic oxaloacetic transaminases; SGPT = serum glutamate pyruvate transaminases;

Effect of Secretin on cAMP Levels in Large Cholangiocytes and Bile and Bicarbonate Secretion in Bile Fistula Rats.

Figures 3A, 3B:
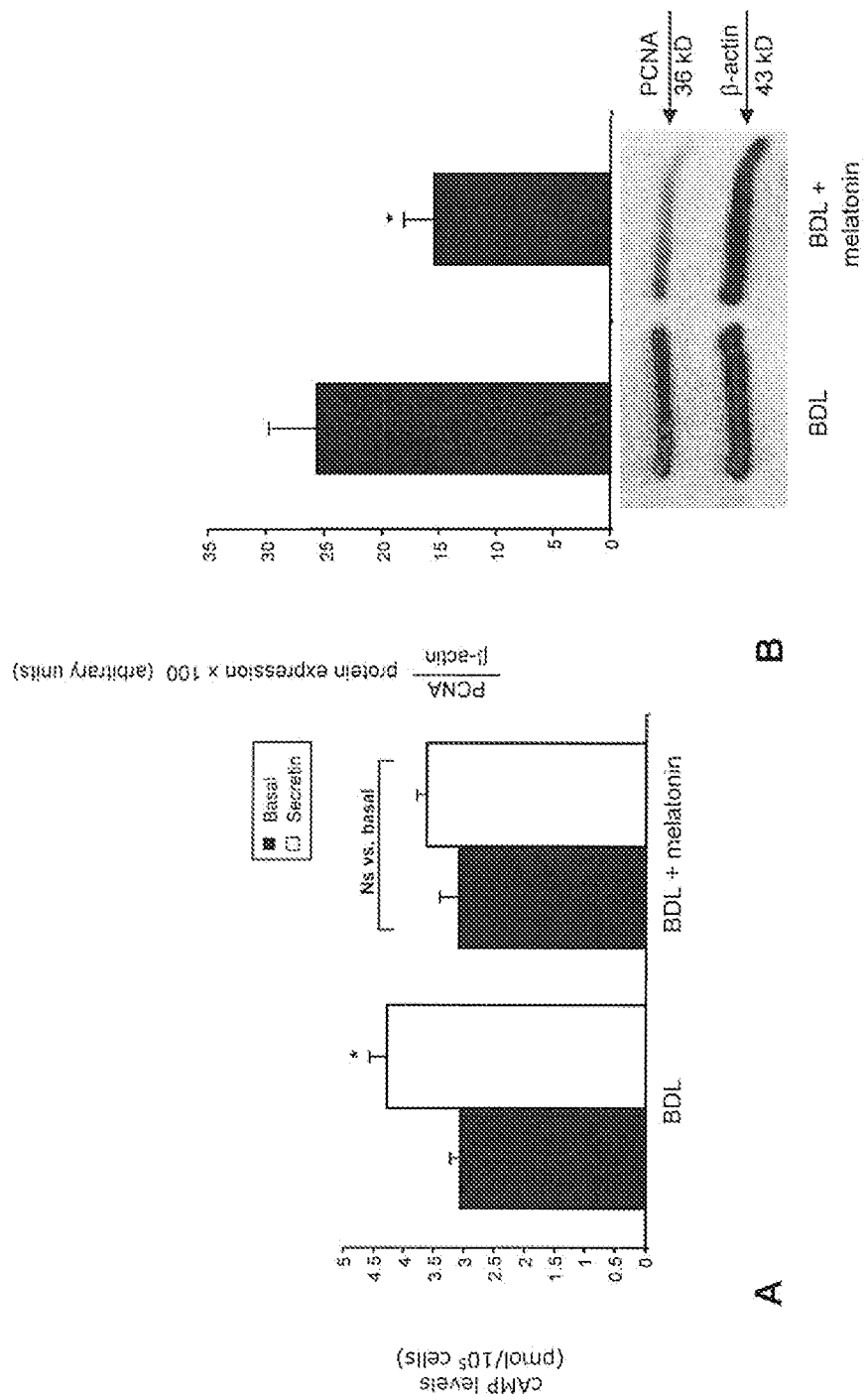
FIGS. 3A-3D [FIG. 3A] Effect of secretin on cAMP levels in purified large cholangiocytes from BDL rats treated with regular tap water or melatonin in drinking water for 1 week. Secretin increased the intracellular cAMP levels of large cholangiocytes from BDL rats. Secretin did not enhance the intracellular levels of cAMP of large cholangiocytes from melatonin-treated rats. Data are mean SEM of 6 evaluations from cumulative preparations of cholangiocytes. $^*p<0.05$ vs. the corresponding basal values of large cholangiocytes from BDL controls.

Secretin increased the intracellular cAMP levels of large cholangiocytes from BDL rats but did not enhance the levels of cAMP of large cholangiocytes from BDL rats treated with melatonin for 1 week (FIG. 3A). At the functional, secretin increased bile and bicarbonate secretion of BDL controls but not of melatonin-treated BDL rats (Table 2).

TABLE 2

Measurement of basal and secretin-stimulated bile flow and bicarbonate secretion in rats that (immediately after BDI) had ad libitum access to regular tap water or tap water containing melatonin for 1 week.

| | Bile Flow | | Bicarbonate Secretion | |
|---|---|---|---|---|
| Treatment | Basal (ml/min/Kg BW) | Secretin (ml/min/Kg BW) | Basal (ml/min/Kg BW) | Secretin (ml/min/Kg BW) |
| XVI. BDI rats + tap water (n = 4) | 124.6 ± 11.9[a] | 226.7 ± 28.2[b] | 4.0 ± 0.3 | 11.0 ± 1.4[b] |
| XVII. BDI rats + XVIII. tap water containing melatonin (n = 4) | 90.1 ± 11.9 | 94.3 ± 11.6[ns] | 2.5 ± 0.4 | 3.4 ± 0.4[ns] |

Data are mean ± SEM.
[a]$p < 0.05$ vs. basal values of bile flow, bicarbonate concentration or bicarbonate secretion of BDI that had ad libitum access to regular tap water containing melatonin for 1 week.
[b]$p < 0.05$ vs. corresponding basal value of bile flow, bicarbonate concentration or bicarbonate secretion of BDI rats that had ad libitum access to regular tap water for 1 week.
[ns]vs. corresponding basal value of bile flow, bicarbonate concentration or bicarbonate secretion of BDI rats that had ad libitum access to regular tap water for 1 week. Differences between groups were analyzed by the Student unpaired t test when two groups were analyzed and analysis of variance (ANOVA) when more than two groups were analyzed.
BDI = bile duct incannulated;
KRH = Krebs Ringer Henseleit.

Effect of Melatonin on the Expression of PCNA, and the Phosphorylation of PKA and ERK1/2 in Large Cholangiocytes.

Figures 3C, 3D:
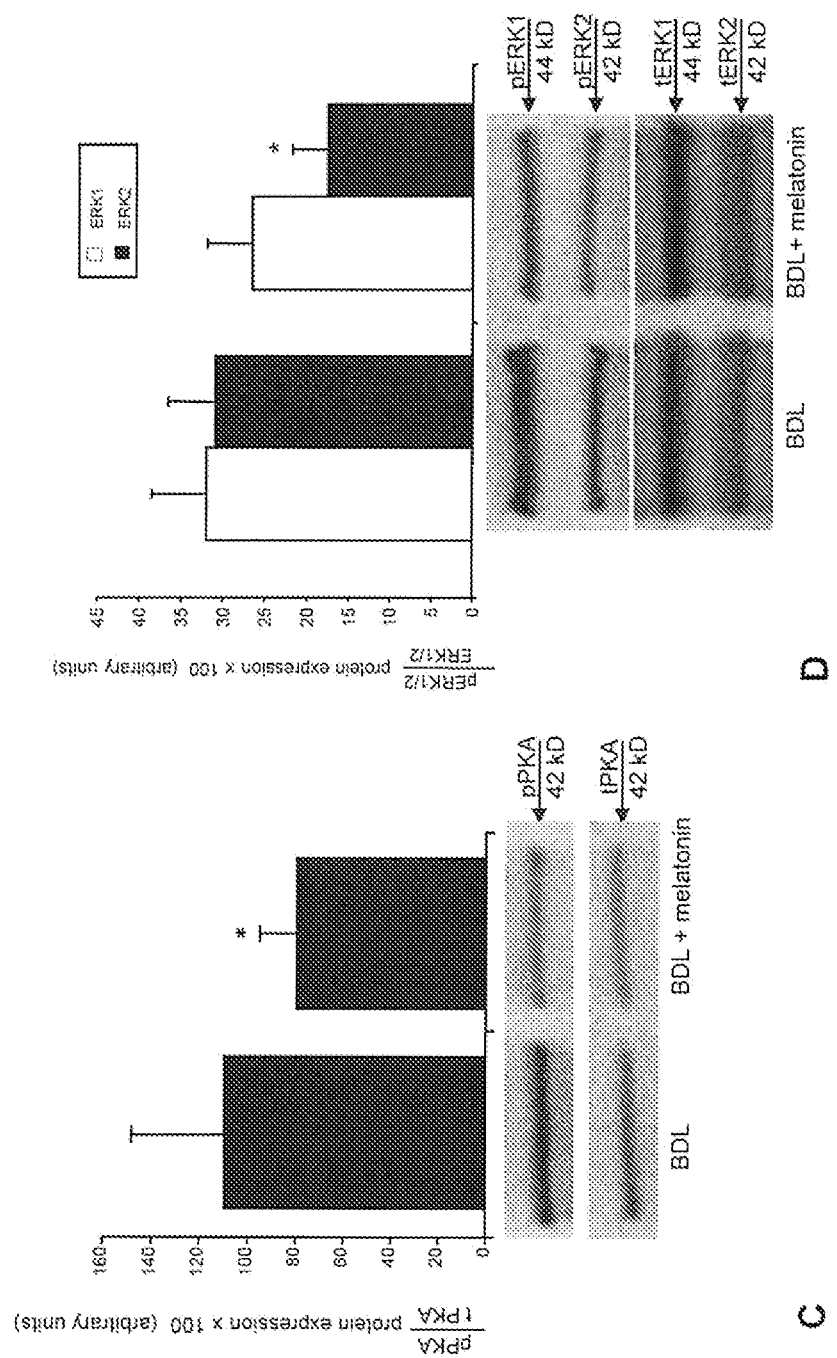
Figures 4A, 4B, 4C, 4D, 4E:
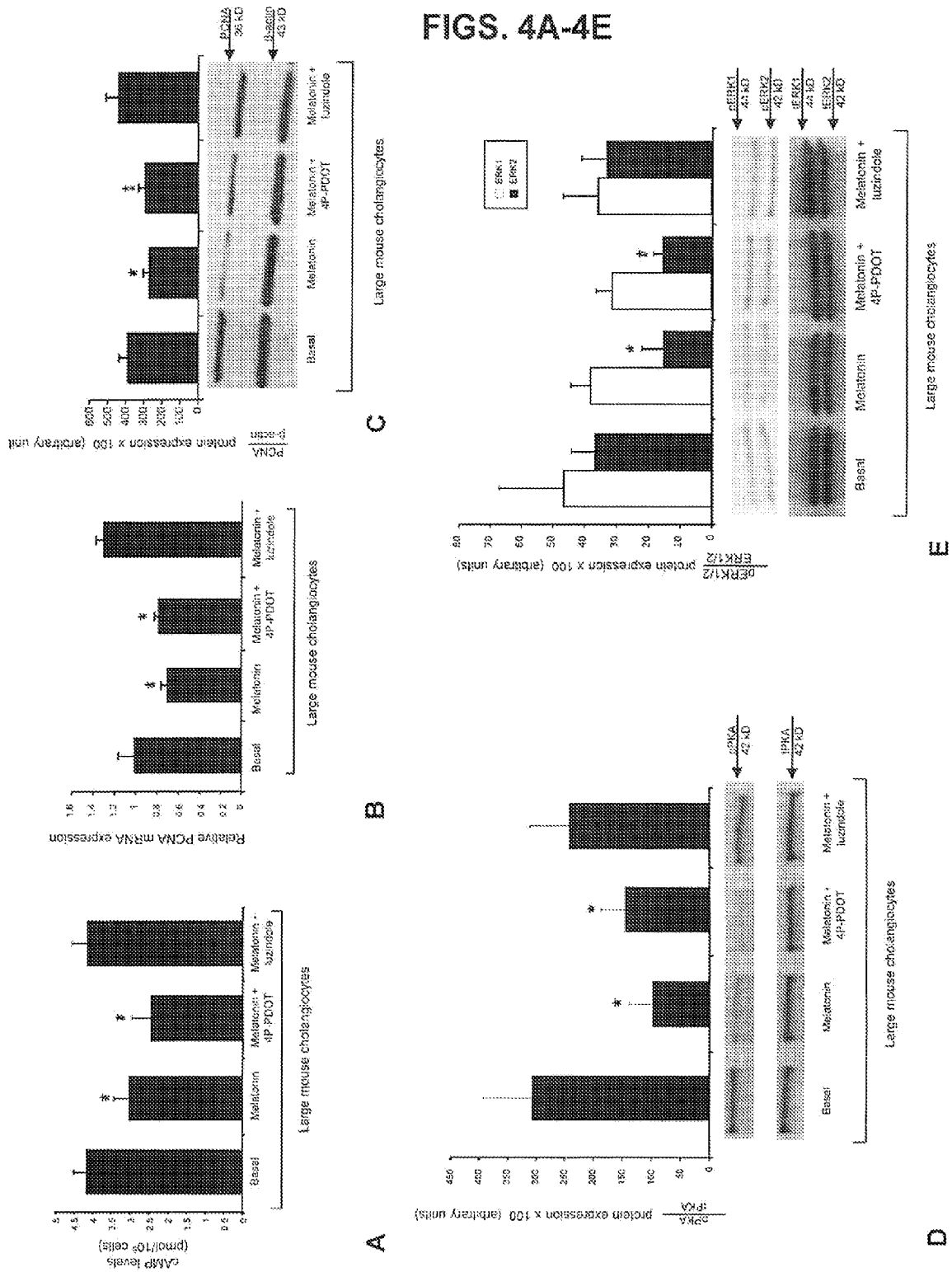
FIGS. 4A-4E Effect of melatonin on [FIG. 4A] cAMP levels, [FIG. 4B] mRNA PCNA expression and [FIG. 4C] PCNA protein expression [FIG. 4D] PKA and [FIG. 4E] ERK1/2 phosphorylation of large cholangiocyte lines. Melatonin decreased cAMP levels, decrease that was prevented by luzindole but not 4-P-PDOT. Melatonin decreased PCNA protein expression and the phosphorylation of PKA and ERK2, decreases that were prevented by luzindole but not 4-P-PDOT. Data are mean SE of 6 evaluations from cumulative preparations of cholangiocytes. $^*p<0.05$ vs. the corresponding basal values of large cholangiocyte lines.

There was decreased PCNA expression in large cholangiocytes from BDL rats treated with melatonin compared to large cholangiocytes from BDL control rats (FIG. 3B). There was also a decreased in the phosphorylation of the cAMP-dependent PKA and ERK2 but not ERK1 (similar to our previous study) (9) in large cholangiocytes from melatonin-treated BDL rats compared to large cholangiocytes from BDL controls (FIGS. 3C-3D).

Effect of Melatonin on the Proliferation of Large Cholangiocytes.

Figures 5A, 5B:
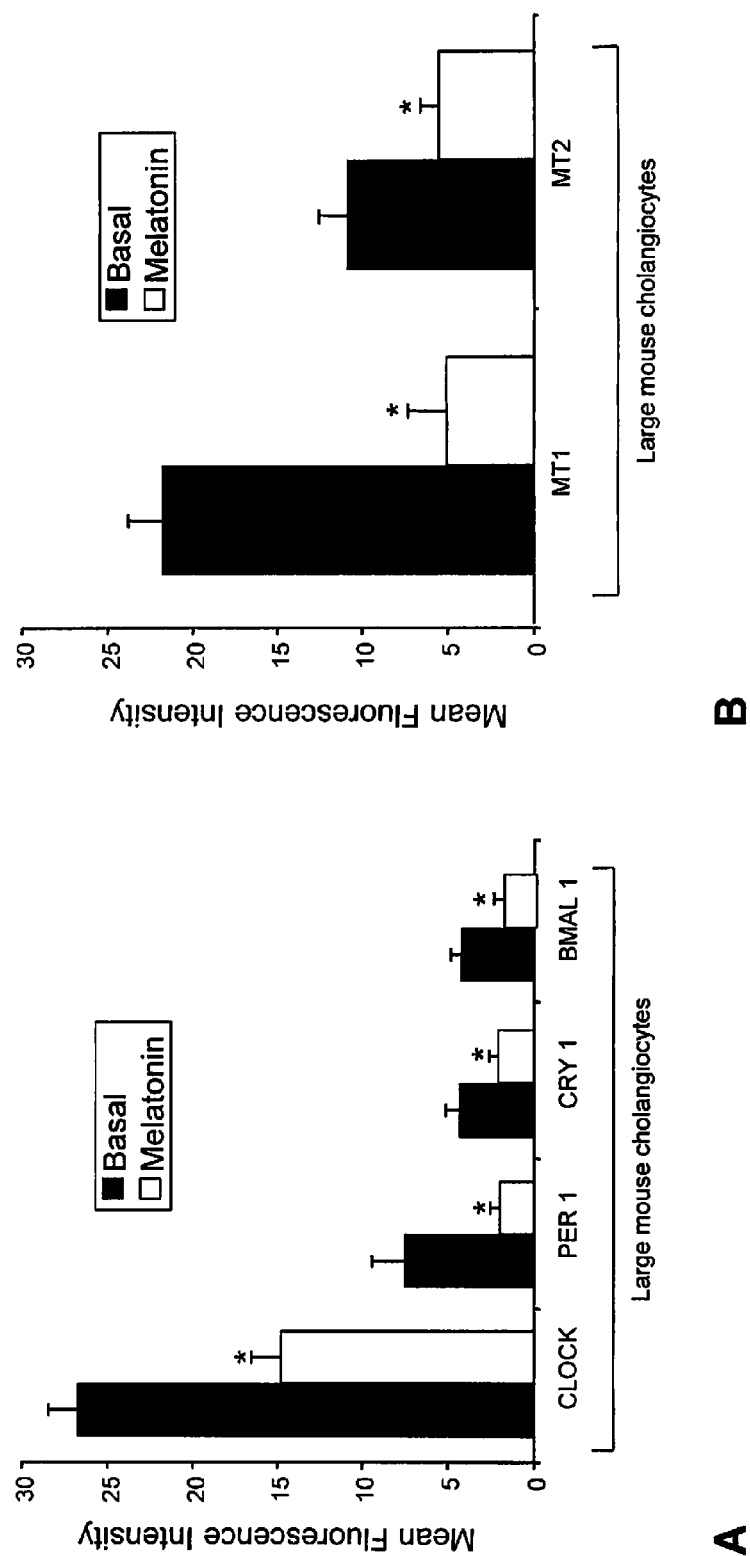
FIGS. 5A-5B [FIG. 5A] By FACS analysis the protein expression of PER1, BMAL1, CRY1 and CLOCK decreased in large mouse cholangiocytes treated with melatonin compared to basal large mouse cholangiocyte cell lines. Data are mean SEM of three evaluations. $^*p<0.05$ vs. the corresponding basal values of large cholangiocyte lines.

By immunofluorescence, large cholangiocyte lines express both MT1 and MT2. Evaluation of MT1 and MT2 expression by immunofluorescence in cell smears of large cholangiocyte lines. By this technique, large cholangiocyte lines were demonstrated to express both MT1 and MT2. Bar=50 μm. Specific receptor immunoreactivity is depicted in red, whereas cells were counterstained with DAPI (blue). Melatonin decreased cAMP levels, decrease that was prevented by luzindole (a MT1/MT2 antagonist) but not 4-P-PDOT (a specific MT2 antagonist) (FIG. 4A) suggesting that melatonin inhibitory effects on cholangiocyte growth are selectively mediated by MT1. Melatonin decreased PCNA expression and the phosphorylation of PKA and ERK2 but not ERK1, decreases that were prevented by luzindole but not 4-P-PDOT (FIGS. 4B-4E). By FACS analysis, in vitro melatonin decreased the expression of PER1, BMAL1, CRY1, and CLOCK (FIG. 5A), and MT1 and MT2 (FIG. 5B) compared to their corresponding basal value.

Methods and Materials

Materials

Reagents were purchased from Sigma Chemical (St Louis, Mo.) unless otherwise indicated. The mouse monoclonal antibody against rat proliferating cell nuclear antigen (PCNA, clone C10) was purchased from Santa Cruz Biotechnology Inc. (Santa Cruz, Calif.). The antibodies recognizing: (i) MT1 (clone R-18, an affinity purified goat polyclonal antibody raised against a peptide mapping near the C-terminus of MT1 of rat origin); and (ii) MT2 (clone T-18, an affinity purified goat polyclonal antibody raised against a peptide mapping within an internal region of MT2 of mouse origin) were purchased from Santa Cruz Biotechnology Inc. The rabbit polyclonal antibodies to the CLOCK (H-276) transcription factor, the goat polyclonal antibody to BMAL 1 (N-20) transcription factor, Cry 1 (A-20) and Per1 (N-20) proteins were purchased from Santa Cruz Biotechnology Inc. The mouse anti-cytokeratin-19 (CK-19) antibody (clone RCK105) was purchased from Caltag Laboratories Inc. (Burlingame, Calif.). The antibody for the rabbit anti-ERK1 (which detects p44 and p42), and goat anti-pERK (which detects phosphorylated p44 and p42) were purchased from Santa Cruz Biotechnology Inc. The cAMP-dependent phospho-PKA catalytic subunit (Thr197) antibody (Cell Signaling, Boston, Mass.) detects endogenous levels of PKA catalytic subunit (-a, -b and -g) only when phosphorylated at Thr197; this antibody does not cross-react with PKA catalytic subunit phosphorylated at other sites. The RNeasy Mini Kit to purify total RNA from purified cholangiocytes was purchased from Qiagen Inc, Valencia, Calif. The RIA kits for the determination of cyclic adenosine 3',5'-monophosphate (cAMP) levels were purchased from GE Healthcare (Arlington Heights, Ill.). 4-Phenyl-2-propionamidotetralin (4-P-PDOT, a specific MT2 antagonist, >300-fold selective for the MT2 vs. the MT1 subtype) (Shiu et al., 2010) and the nonselective MT1/MT2 antagonist, luzindole (Drazen et al., 2001), were purchased from Tocris Bioscience, Ellisville, Mo.

Animal Models

Male 344 Fischer rats (150-175 g) were purchased from Charles River (Wilmington, Mass.) and kept in a temperature-controlled environment (22° C.) with 12:12 hr light/dark cycles. Animals were fed ad libitum and had free access to food and drinking water. The studies were performed in normal rats, and in rats that immediately after bile duct ligation (BDL, for collection of serum, liver tissues and cells) (Alpini et al., 1988) or bile duct incannulation (BDI, for bile collection) (Alpini et al., 1988) had ad libitum access to tap water or tap water containing melatonin (20 mg/L in drinking water that corresponds to approximately an intake of melatonin of 2 mg/g BW per day per rat) (Anisimov et al., 2003) for 1 week. Before each surgical procedure, animals were anesthetized with sodium pentobarbital (50 mg/kg BW, IP). All animal experiments were performed in accordance with a protocol approved by the Scott and White and Texas A&M Health Science Center Institutional Animal Care and Use Committee and conform to the Guide for the Care and Use of Laboratory Animals published by the US National Institutes of Health (NIH Publication No. 85-23, revised 1996). In all animals, wet liver weight, body weight, wet liver weight to body weight ratio, and an index of liver cell growth including cholangiocytes were measured (Alpini et al., 1988).

Expression of MT1 and MT2, and the Clock Genes, CLOCK, BMAL 1, Cry1 and Per 1 in Liver Sections and Cholangiocytes The expression of MT1 and MT2, and the Clock Genes, CLOCK, BMAL 1, Cry1 and Per 1 was evaluated: (i) in paraffin-embedded liver sections (4-5 mm thick) from normal and BDL control rats by immunohistochemistry (Mancinelli et al., 2009); and (ii) in total RNA (1 µg, by real-time PCR) (Francis et al., 2008) from purified cholangiocytes. The expression of MT1 and MT2 mRNAs was also measured in hepatocytes (Ishii et al. 1989) and vascular endothelial cells (Meininger and Wu, 2002) from BDL rats treated with vehicle or melatonin for 1 week. The expression of the protein for MT1 and MT2, Clock, BMAL 1, Cry 1, and Per 1 was evaluated by FACS analysis in purified large cholangiocytes from rats that (immediately after BDL) had access to regular tap water or tap water containing melatonin for 1 week. FACS analysis was performed as described (Onori et al., 2010) using a C6 flow cytometer and analyzed by CFlow Software (Accuri Cytometers Inc. Ann Arbor, Mich.). At least 10,000 events in the light-scatter (SSC/FSC) were acquired. The expression of the selected protein was identified and gated on FL1-A/Count plots. The relative quantity of the selected protein (mean selected protein fluorescence) was expressed as mean FL1-A (samples)/mean FL-1A (secondary antibodies only).

For immunohistochemistry, liver sections were incubated overnight at 4° C. with the selected antibody for (dilution 1:50), washed in 1× phosphate buffered saline (PBS), incubated for 20 minutes at room temperature with a secondary biotinylated antibody (Dako Cytomation LSAB Plus System-HRP, Glostrup), then with Dako ABC for 20 minutes and developed with 3-3' diaminobenzidine (Dako Cytomation Liquid DAB Plus Substrate Chromogen System, Glostrup). Immunohistochemical observations were taken in a coded fashion by two certified pathologists by BX-51 light microscopy (Olympus, Tokyo, Japan) with a Videocam (Spot Insight; Diagnostic Instrument, Inc., Sterling Heights, Mich.) and analyzed with an Image Analysis System (IAS; Delta Sistemi, Rome, Italy). For all immunoreactions, negative controls (with normal serum from the same species substituted for the primary antibody) were included.

To evaluate the expression of the messages for MT1 and MT2, Clock, BMAL 1, Cry 1, and Per 1 in purified large cholangiocytes, the $RT^2$ Real-Time assay from SABiosciences (Frederick, Md.) was used (Francis et al., 2008). A $DDC_T$ (delta delta of the threshold cycle) analysis was performed (Francis et al., 2008) using normal cholangiocytes as the control sample. Data were expressed as relative mRNA levels ±SEM of the selected gene to glyceraldehyde-3-phosphate dehydrogenase (GAPDH) ratio. The primers for melatonin receptors 1A and 1B, Clock, BMAL 1, Cry 1, and Per 1 (purchased from SABiosciences) were designed according to the NCBI GenBank® Accession numbers: XM_341441 (for MT1) (Ramirez et al., 2009), NM_053330 (for MT2) (Strausberg et al., 2002), NM_021856 (for clock gene) (Zeman et al., 2009), NM_024362 (for BMAL 1 gene) (Honma et al., 1998), NM_198750 (for CRY 1) (Ando et al., 2009), and NM_001034125 (for Per 1) (Nagano et al., 2009).

Immortalized and Freshly Isolated Large Cholangiocytes

Pure (100% by γ-glutamyltransferase, g-GT, histochemistry) (Rutenburg et al., 1969) and viable (97% by trypan blue exclusion) large cholangiocytes were isolated by immunoaffinity separation (Alpini et al., 1997) using a monoclonal antibody (IgM, kindly provided by Dr. R. Faris, Brown University, Providence, R.I.) that recognizes an unidentified antigen expressed by all intrahepatic cholangiocytes (Ishii et al., 1989). The rationale for performing these studies only in large cholangiocytes is based on the fact that following BDL only these cell types undergo mitosis leading to enhanced ductal mass (Alpini et al., 1998; Glaser et al., 2009; LeSage et al., 1999). The in vitro studies were performed in immortalized large cholangiocytes (derived from large bile ducts) (Ueno et al., 2003), which were shown to display morphological and functional phenotypes similar to that of freshly isolated large rat and mouse cholangiocytes (Alpini et al., 1998; Alpini et al., 1997; Francis et al., 2008; Glaser et al., 2010; Ueno et al., 2003).

Evaluation of Lobular Damage, Serum Levels of Melatonin, Transaminases, and Bilirubin and Cholangiocyte Proliferation and Apoptosis In the selected groups of animals, the serum levels of the transaminases, serum glutamate pyruvate transaminases (SGPT) and serum glutamic oxaloacetic transaminase (SGOT) and total bilirubin were evaluated using a Dimension RxL Max Integrated Chemistry system (Dade Behring Inc., Deerfield Ill.) by the Chemistry Department, Scott & White. Melatonin serum levels were measured by commercially available ELISA kits according to the instructions provided by the vendor (Genway, San Diego, Calif.).

The following was also evaluated in paraffin-embedded liver sections (4-5 mm thick): (i) lobular necrosis; (ii) the intrahepatic bile duct mass (IBDM) of large (>15 mm diameter) (Alpini et al., 1997; Glaser et al., 2009) cholangiocytes, the only biliary cell types proliferating following BDL (Alpini et al., 1998; Glaser et al., 2009) and (iii) the percentage of cholangiocyte apoptosis by semiquantitative terminal deoxynucleotidyltransferase biotin-dUTP nick-end labeling (TUNEL) kit (Apoptag; Chemicon International, Inc.) (Glaser et al., 2010). Lobular necrosis was measured in liver sections stained for hematoxylin and eosin (Glaser et al., 2010). Lobular necrosis was scored as follows: –=0 foci; +/–=<2 foci; +=2-4 foci; and ++=>4 foci (Glaser et al., 2010). The IBDM was measured as area occupied by CK-19 positive-bile duct/total area×100 (Glaser et al., 2010). It was also evaluated by H&E of sections if melatonin administration induces the damage of kidney, heart, stomach, spleen and small and large intestine of normal and BDL rats. The sections from the selected were evaluated in a blinded-fashion by two board-certified pathologists by a BX-51 light microscope (Olympus, Tokyo, Japan) equipped with a camera.

Measurement of the Expression of PCNA and the Phosphorylation of PKA and ERK1/2 in Purified Large Cholangiocytes Cholangiocyte proliferation was evaluated by immunoblots (Francis et al., 2008) by determination of PCNA protein expression (measured as ratio to b-actin protein expression) (Francis et al., 2008), and the phosphorylation of cAMP-dependent PKA and ERK1/2 (expressed as ratio to protein expression of the corresponding total proteins) in protein (10 mg) from whole cell lysate from spleen (positive control) and large cholangiocytes from BDL rats treated with vehicle or melatonin. The intensity of the bands was determined by scanning video densitometry using the phospho-imager Storm 860 and the ImageQuant TL software version 2003.02 (GE Healthcare).

Measurement of Basal and Secretin-Stimulated cAMP Levels in Purified Large Cholangiocytes and Bile and Bicarbonate Secretion In Vivo The effect of secretin on cAMP levels was evaluated in purified large cholangiocytes and bile and bicarbonate secretion was evaluated in bile fistula rats, two functional indices of cholangiocyte hyperplasia (Alpini et al., 1998; Alpini et al., 1988; LeSage et al., 1999). Following purification, large cholangiocytes ($1\times10^5$ cells) were incubated for 1 hour at 37° C. (Ishii et al., 1989) before stimulation with 0.2% bovine serum albumin (BSA) or secretin (100 nM) for 5 minutes at room temperature (Kato et al., 1992; LeSage et al., 1999; LeSage et al., 2004) before evaluation of cAMP levels by RIA (Alpini et al., 1998; Kato et al., 1992; LeSage et al., 1999; LeSage et al., 2004). For the studies of biliary physiology, after anesthesia, rats were surgically prepared for bile collection as described by us (Alpini et al., 1988). When steady-state bile flow was reached (60-70 minutes from the intravenous infusion of Krebs-Ringer-Henseleit solution, KRH), the animals were infused with secretin (100 nM) (LeSage et al., 1999; LeSage et al., 2004) for 30 minutes followed by IV infusion of KRH for 30 minutes (LeSage et al., 1999; LeSage et al., 2004). Bicarbonate concentration in bile was determined by an ABL™ 520 Blood Gas System (Radiometer Medical A/S, Copenhagen, Denmark).

Expression of Melatonin Receptors in Immortalized Large Cholangiocytes and Mechanisms by which Melatonin Regulates the Proliferation of Immortalized Large Cholangiocytes The expression of MT1 and MT2 receptors in immortalized large cholangiocytes was first evaluated by immunofluorescence (Francis et al., 2008). Images were visualized using an Olympus IX-71 confocal microscope. For all immunoreactions, negative controls (with normal serum from the same species substituted for the primary antibody) were included. It was next evaluated by commercially available radioimmunoassay (RIA) kits (Alpini et al., 1998; Kato et al., 1992; LeSage et al., 1999; LeSage et al., 2004) for cAMP levels (Alpini et al., 1998; Kato et al., 1992; LeSage et al., 1999) in large mouse cholangiocyte lines treated at room temperature with 0.2% bovine serum albumin (BSA) or melatonin ($10^{-11}$ M for 5 minutes) in the absence or presence of preincubation with 4-P-PDOT or luzindole (both 10 mM) (Drazen et al., 2001; Shiu et al., 2010). The rationale for using this dose ($10^{-11}$ M) for melatonin in the in vitro studies is based on the finding that serum levels of melatonin in rodents and human are on the picomolar to nanomolar ranges (Dollins et al., 1994; Porkka-Heiskanen et al., 1992; Ramirez-Rodriguez et al., 2009; Vanecek, 1999). In separate sets of experiments, after trypsinization large cholangiocytes were treated at 37° C. for 48 hours with 0.2% BSA or melatonin ($10^{-11}$ M) in the absence or presence of preincubation with 4-P-PDOT or luzindole (dissolved in DMSO, both at 10 mM) (Drazen et al., 2001; Shiu et al., 2010) before evaluating by immunoblots (Francis et al., 2008) the expression of PCNA and the phosphorylation of PKA and EKR1/2.

Statistical Analysis

All data are expressed as mean±SEM. Differences between groups were analyzed by Student's unpaired t-test when two groups were analyzed and ANOVA when more than two groups were analyzed, followed by an appropriate post hoc test.

Example 2

Decreased Melatonin Synthesis in Cholangiocarcinoma (CCA) Suppresses its Antiproliferative Actions by Upregulation of Clock Gene Background: Melatonin is secreted from several extrapineal tissues and cells, such as retina, gastrointestinal tract, and liver and acts both as a hormone of the pineal gland and a local growth regulator in various tissues. Melatonin exerts it effects through two membrane receptors (MT1 and MT2) and is synthesized from serotonin by two enzymes, serotonin Nacetyltransferase (arylalkylamine N-acetyltransferase (AANAT) and acetylserotonin Omethyltransferase (ASMT)). Cholangiocarcinoma (CCA) is a lethal disease afflicting thousands of patients worldwide. The mechanisms regulating CCA growth are poorly understood. The CLOCK gene encodes proteins regulating circadian rhythm and acts as a tumorsuppressor by regulating the balance between growth/apoptosis in several tumors.

The aims were to assess 1) the levels of melatonin, melatonin biosynthesis enzymes (AANAT and ASMT), melatonin receptors (MT1 and MT2) and the CLOCK gene in normal and CCA lines and CCA tissue, and 2) the effects of melatonin on cell growth.

Methods: Melatonin immunoreactivity, the expression of melatonin biosynthesis enzymes and receptors were assessed by immunohistochemistry in tissue arrays from normal and CCA patients, and by qPCR and immunoblots in intra-hepatic and extra-hepatic CCA cell lines, and a normal cholangiocyte line (H69). Proliferation was evaluated in vitro by MTS assay in CCA lines and H69 after treatment with melatonin (10-7 to 10-11 M, 24-72 hours). In parallel, the expression of CLOCK after melatonin treatment (10-11 M for 48 hours) was assessed in CCA lines and normal cholangiocytes by qPCR.

Results: Melatonin immunoreactivity decreased (~78%) whereas MT1 and MT2 expression increased (~60%) in CCA compared to controls. AANAT significantly decreased (~50%) in CCA samples, and in 5 out of 6 CCA cell lines studied. ASMT decreased (by 60%) significantly in Grade 1 CCA samples when compared to normal samples, and decreased in all CCA cell lines studied. In vitro, melatonin induced a 65% decrease in CCA growth compared to normal cholangiocytes. The levels of the CLOCK gene were increased (~50%) in CCA cells treated with melatonin.

Conclusions: CCA produce lower levels of melatonin and treatment of CCA cells with melatonin decreases the growth of these tumor cells. There is an up-regulation of the CLOCK gene associated with the antiproliferative effects induced by melatonin. Local modulation of melatonin synthesis by CCA may be an important autocrine loop for the management of this tumor.

Example 3

Melatonin Inhibits In Vivo Cholangiocarcinoma Growth

Cholangiocarcinoma (CCA) is a tumor characterized by late presentation of symptoms and limited treatment options. The hormone, melatonin, modulates circadian rhythms and the growth of various cancers. It was previously shown that melatonin decreases CCA growth in vitro via modulation of clock genes. CCA cells have lower levels of AANAT, but, the functional autocrine role of melatonin synthesis in the regulation of CCA growth is unknown. The aims were to: (i) Assess the expression levels of AANAT in CCA, and the resulting levels of melatonin in the serum and bile of CCA patients and supernatants from CCA lines; (ii) Determine the effects of AANAT overexpression on CCA growth; and (iii) evaluate the in vivo effects of melatonin on CCA growth in athymic mice.

AANAT expression was assessed in liver biopsy samples from CCA patients and controls by immunohistochemistry, and in non-malignant cholangiocytes and intra- and extra-hepatic CCA lines by qPCR and immunoblots. Melatonin secretion was assessed in the supernatant of normal and CCA lines, and serum and bile from controls and CCA patients by EIA. In the CCA line Mz-ChA-1 stably overexpressing AANAT, the expression of AANAT, melatonin secretion, and CCA proliferation were studied after 48 hr of incubation. In vivo studies, Mz-ChA-1 cells were injected Sub Q into the hind flanks of nu/nu mice. Tumors were allowed to develop and volumes were measured for 41 days during treatment with saline or melatonin (4 mg/kg BW, IP 3×wk). Tumors were analyzed for AANAT, PCNA, CK-19 and Bax by qPCR and immunoblots. Tumor tissue sections were analyzed for TUNEL, and staining for AANAT, PCNA and CK-19.

The Expression of AANAT and ASMT is Downregulated in Cholangiocarcinoma.

Figures 6A, 6B:
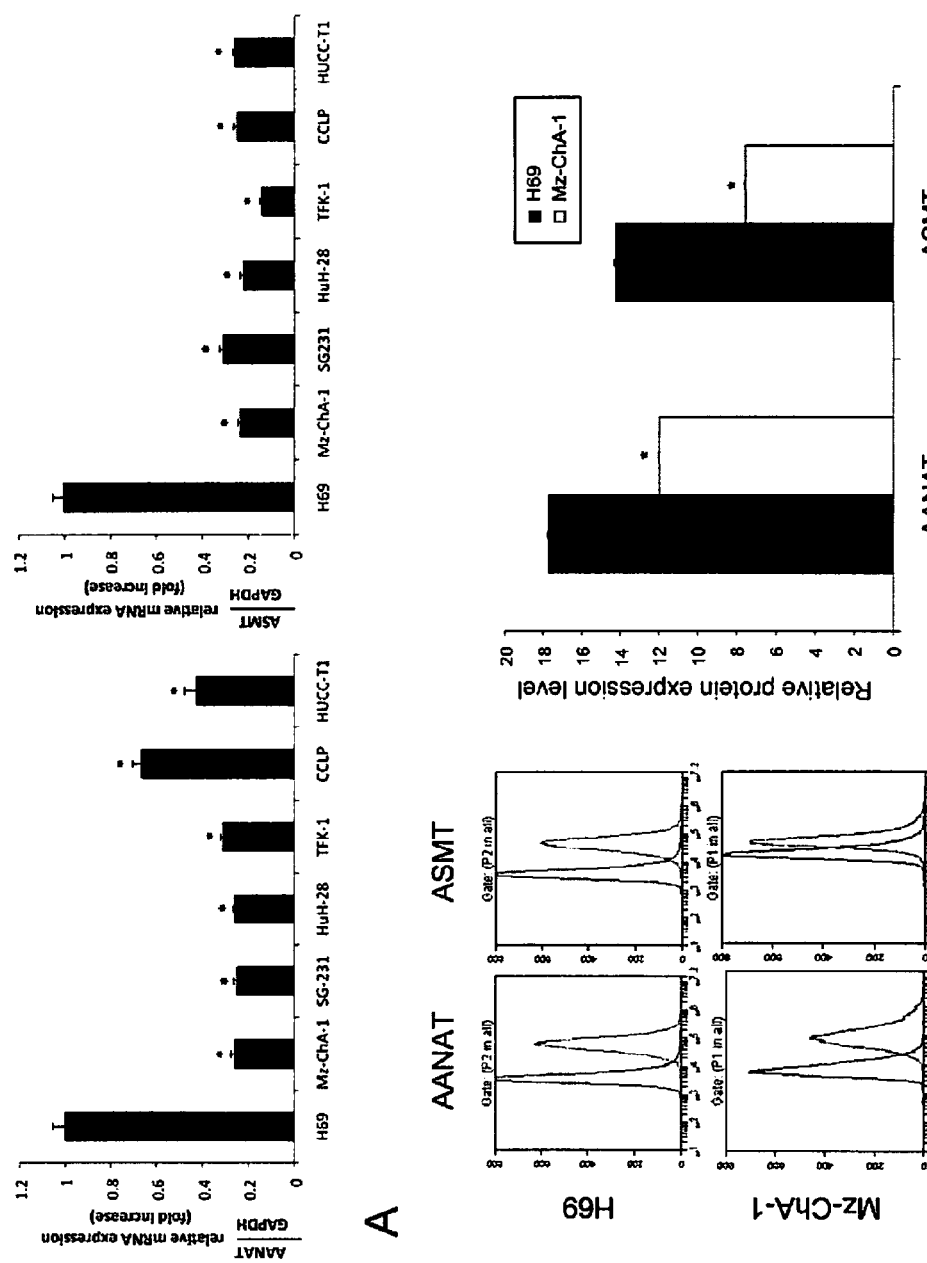
FIGS. 6A-6C [FIG. 6A] mRNA expression of AANAT and ASMT decreased significantly in all CCA lines compared to H69. Data are mean±SEM of four evaluations. $^*p<0.05$ vs. the values of nonmalignant human cholangiocytes.
Figure 6C:
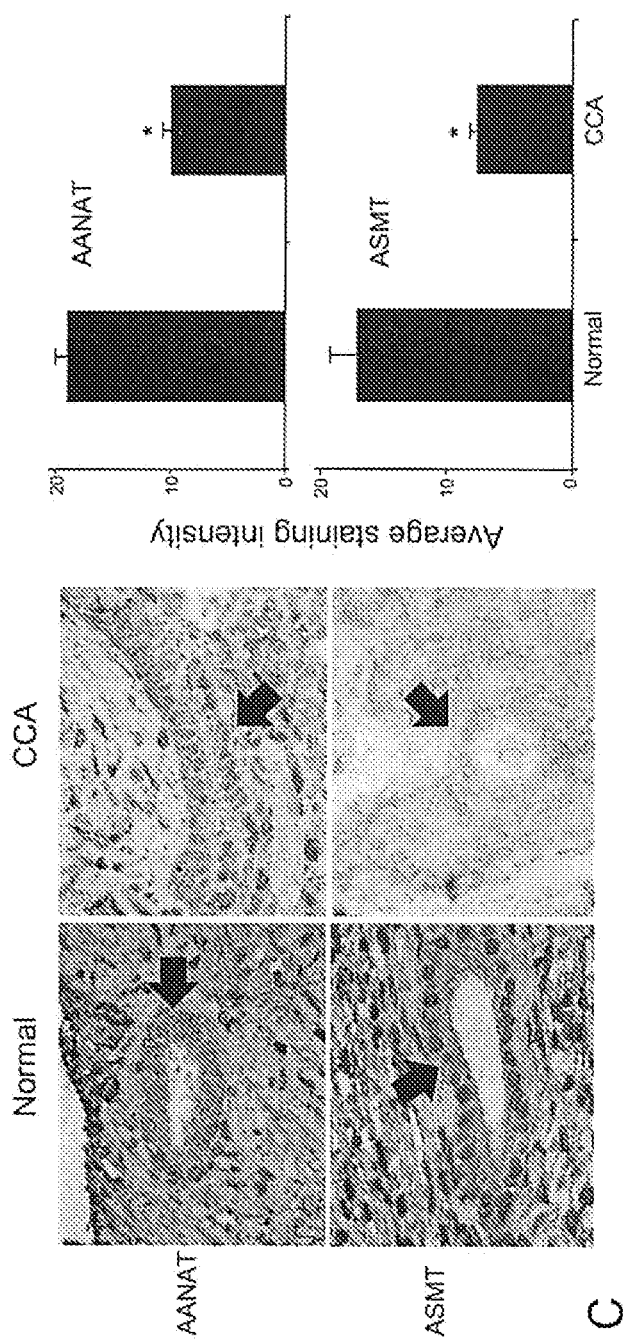

Measurement of AANAT and ASMT in non-malignant and CCA lines and liver biopsy samples from controls and CCA patients. By immunofluorescence, AANAT and ASMT are expressed by all CCA lines as well as H69. Specific immunoreactivity is seen in red and cells were counterstained with DAPI (blue) Bar=50 mm. mRNA expression of AANAT and ASMT was significantly decreased in all CCA lines compared to H69 (FIG. 6A). By FACS analysis, the protein expression for AANAT and ASMT decreased in Mz-ChA-1 cells compared to H69 cells (FIG. 6B); in this experiment we used only Mz-ChA-1 cells because these cells were used to evaluate the effect of melatonin on the growth of Mz-ChA-1 cells in nude mice. The immunohistochemical expression of AANAT and ASMT significantly decreased in biopsies of CCA patients compared to controls (FIG. 6C).

The Expression and Secretion of Melatonin is Reduced in Cholangiocarcinoma.

Melatonin immunoreactivity decreased in biopsies of CCA patients compared to controls (FIG. 7A). The secretion of melatonin decreased markedly in Mz-ChA-1 lines compared to H69 cells (FIG. 7B). Melatonin was secreted at significant lower (8-fold) rate in the supernatant of CCA lines compared to controls. Also, the secretion of melatonin was mostly active in the apical domain of H69 cells (FIG. 7B). Consistent with apical melatonin secretion by CCA, melatonin levels decreased in the bile (but not serum) of patients with intrahepatic CCA compared to controls (FIG. 7C). The decrease of melatonin levels observed in bile from primary sclerosing cholangitis (PSC) (not shown due to small sample size) and CCA patients suggest the role of melatonin as a possible diagnostic tool (during ERCP) for evaluating liver diseases at early stages.

Expression of Melatonin Receptors in Cholangiocarcinoma.

Figure 8A:
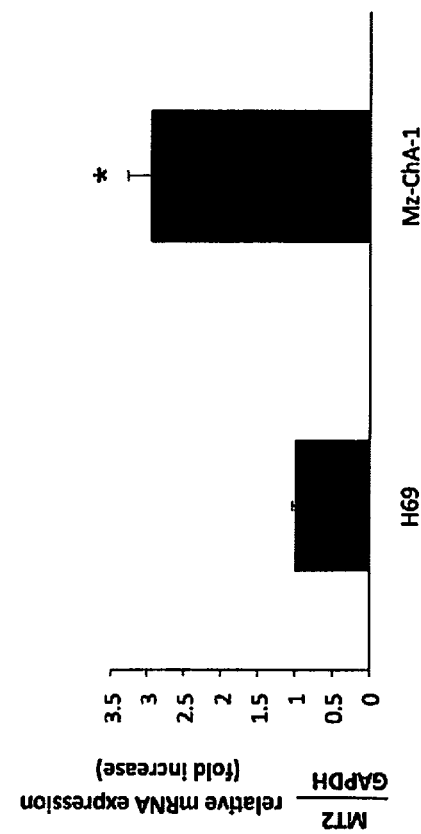
FIGS. 8A-8C Evaluation of MT1 and MT2 expression in CCA cell lines and liver biopsy samples from controls and CCA patients The gene [FIG. 8A] and protein [FIG. 8B] expression of MT1 and MT2 significantly increased in Mz-ChA-1 cells compared to H69. Data are mean±SEM of four experiments. *p<0.05 vs. the corresponding values of H69 cells.
Figure 8A:
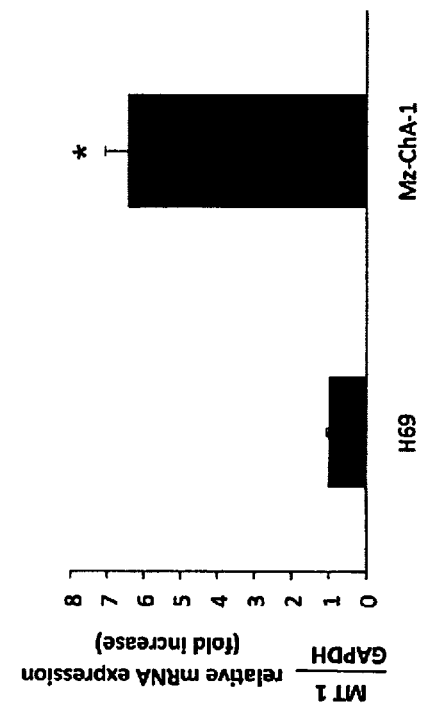
Figure 8B:
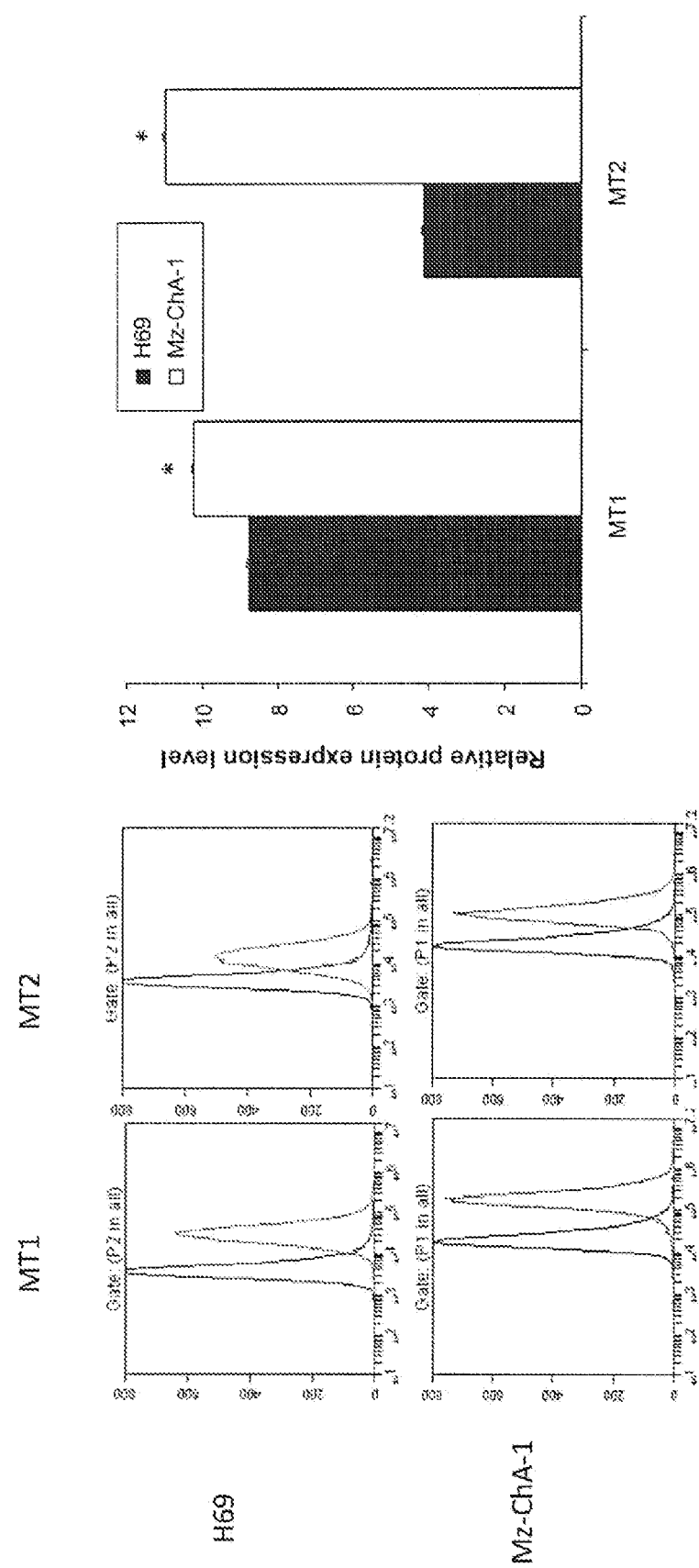
Figure 8C:
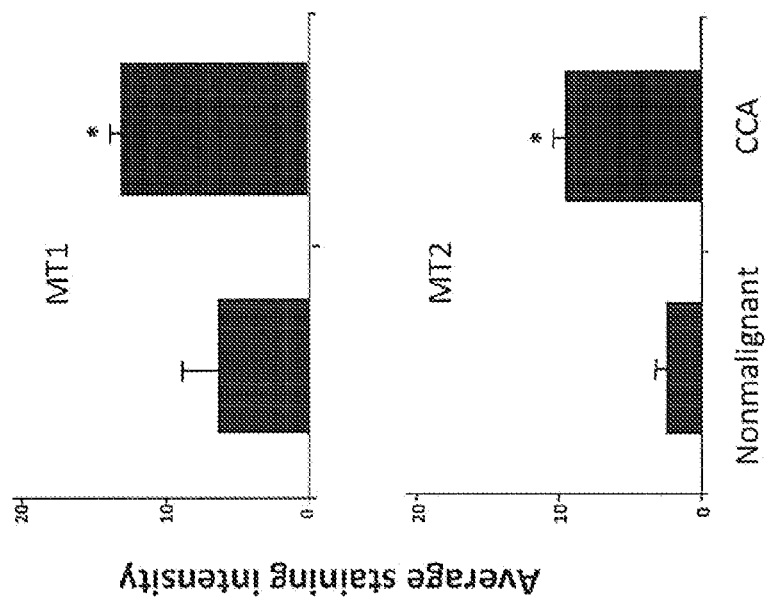
Figure 8C:
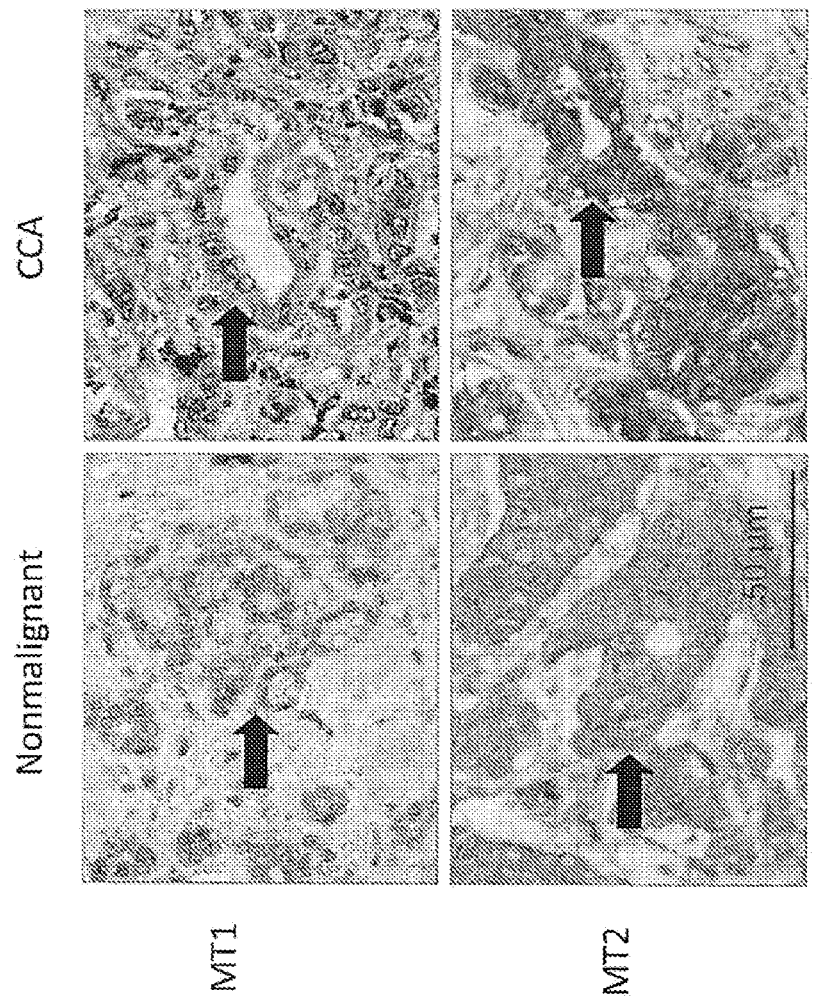

There was evaluation of MT1 and MT2 expression in CCA cell lines and liver biopsy samples from controls and CCA patients. By immunofluorescence, all CCA cell lines as well as H69 expressed MT1 and MT2. The gene and protein expression of MT1 and MT2 was significantly higher in Mz-ChA-1 cells compared to H69 (FIGS. 8A-B) and in liver biopsy samples from CCA patients compared to controls (FIG. 8C).

Melatonin Inhibits Cholangiocarcinoma Growth In Vivo.

Figure 9:
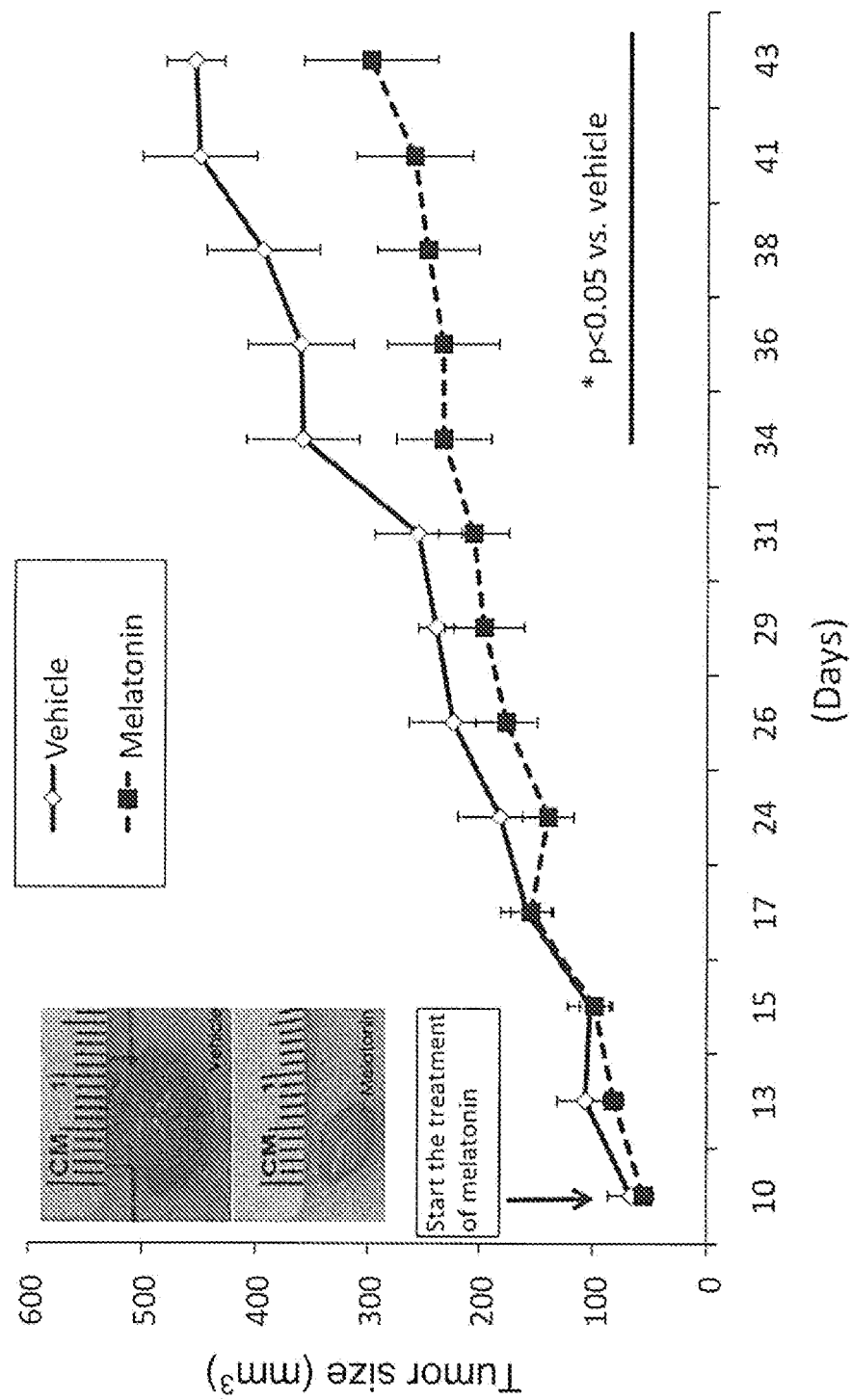
FIG. 9 Melatonin administration reduced CCA tumor growth. After 34 days of melatonin administration, there was a significant decrease in tumor size in nude mice treated with melatonin compared to mice treated with vehicle. Representative pictures of the tumors from vehicle- and melatonin-treated mice, and a summary graph of each data point are also shown. Data are mean±SEM of tumor size evaluations from four mice per each group of animals. *p<0.05 vs. the corresponding values of tumor volume of nude mice treated with vehicle.

After 34 days of melatonin administration, there was a significant decrease in tumor size in nude mice treated with melatonin compared to mice treated with vehicle (FIG. 9). Representative pictures of the tumors from vehicle- and melatonin-treated mice, and a summary graph of each data point are shown in FIG. 9. No significant difference in body weight, liver weight and liver to body weight ratio was observed between the two groups of mice (Table 3). By histological examination of tumor sections there was increased necrosis in sections from melatonin-treated mice compared to control mice. These findings were characterized by a decrease in CCA proliferation (by PCNA) and an increase in CCA apoptosis (by cleaved caspase-3) in tumor sections from melatonin-treated mice compared to vehicle-treated mice. By immunohistochemistry in tumor sections, an increase in the expression of AANAT, ASMT, melatonin and a decrease in MT1/MT2 expression in nude mice treated with melatonin compared to controls were observed. For semiquantitative data see Table 4.

TABLE 3

Measurement of liver and body weight, and liver to body weight ration in nude mice treated with vehicle or melatonin in vivo (Values are mean ± SEM of three mice for vehicle and four mice for the melatonin group).

| Parameter | Vehicle | Melatonin |
|---|---|---|
| Body weight (gm) | 34.2 ± 1.48 | 35.25 ± 0.73 |
| Liver weight (gm) | 2.67 ± 0.22 | 2.82 ± 0.13 |
| Liver to body (%) | 7.78% ± 0.3 | 8.01% ± 0.21 |

TABLE 4

Semiquantitative data for the expression of necrosis, PCNA, cleaved caspase-3, melatonin, AANAT, ASMT, MT1 and MT2 in nude mice treated with vehicle or melatonin (Values are mean ± SEM of four randomly chosen fields [#]The percentage is based on the whole field of section *$p < 0.05$ vs. vehicle).

| Parameter | Vehicle | Melatonin |
|---|---|---|
| Necrosis | <5%[#] | >75%[Ψ] |
| PCNA | 0.77 ± 0.05 (% of total nucleus) | 0.25 ± 0.09 (% of total nucleus) |
| Cleaved caspase-3 | 151.36 ± 53.59 | 4490.66 ± 1053.52* |
| Melatonin | 10464 ± 2034.44 | 41231.48 ± 7634.43* |
| AANAT | 567.22 ± 131.95 | 1584.52 ± 127* |
| ASMT | 6173.15 ± 1008.19 | 46051.09 ± 13063.04* |
| MT1 | 6362.05 ± 672.01 | 1847.76 ± 419.9* |
| MT2 | 5081.64 ± 607.34 | 1417.96 ± 425.71* |

Figures 10A, 10B:
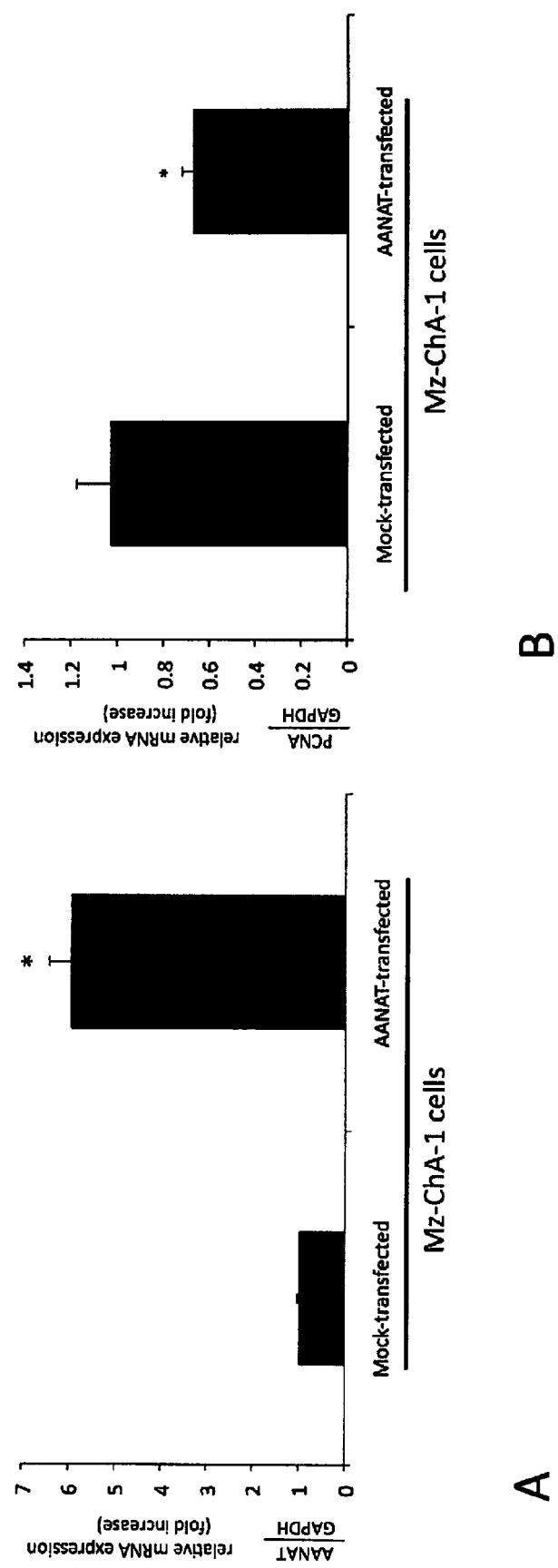
FIGS. 10A-10B Effect of in vitro over-expression of AANAT in Mz-ChA-1 cells on the growth of the cell line. In Mz-ChA-1 cells (stably overexpressing AANAT, ~70% transfection evaluated by real-time PCR) [FIG. 10A] cells there was [FIG. 10B] reduction of PCNA protein compared to mock-transfected Mz-ChA-1 cells. Data are mean±SEM of four evaluations. *p<0.05 vs. the corresponding values of mock-transfected Mz-ChA-1 cells.

Overexpression of AANAT Decreases CCA Proliferation:

Studies have shown that melatonin inhibits cancer growth and resynchronizes dys-regulated circadian rhythm circuitry (Cabrera et al., 2010; Sanchez-Barcelo et al., 2010; Fan et al., 2010; Akbulut et al., 2009; Nah et al., 2009; Martin-Renedo et al., 2008; Jung-Hynes et al. 2010). After overexpression of AANAT in CCA cell there was increased melatonin secretion and inhibition of CCA proliferation (FIGS. 10A-10B). Stable transfection of AANAT cDNA into Mz-ChA-1 cells increased the expression of AANAT by 170% compared to the mock-transfected cell line (FIG. 10A). In these cells there was a reduction of PCNA in mRNA level compared to mock-transfected Mz-ChA-1 cells (FIG. 10B). AANAT overexpression also significantly reduced BMAL1 gene expression.

Figure 11:
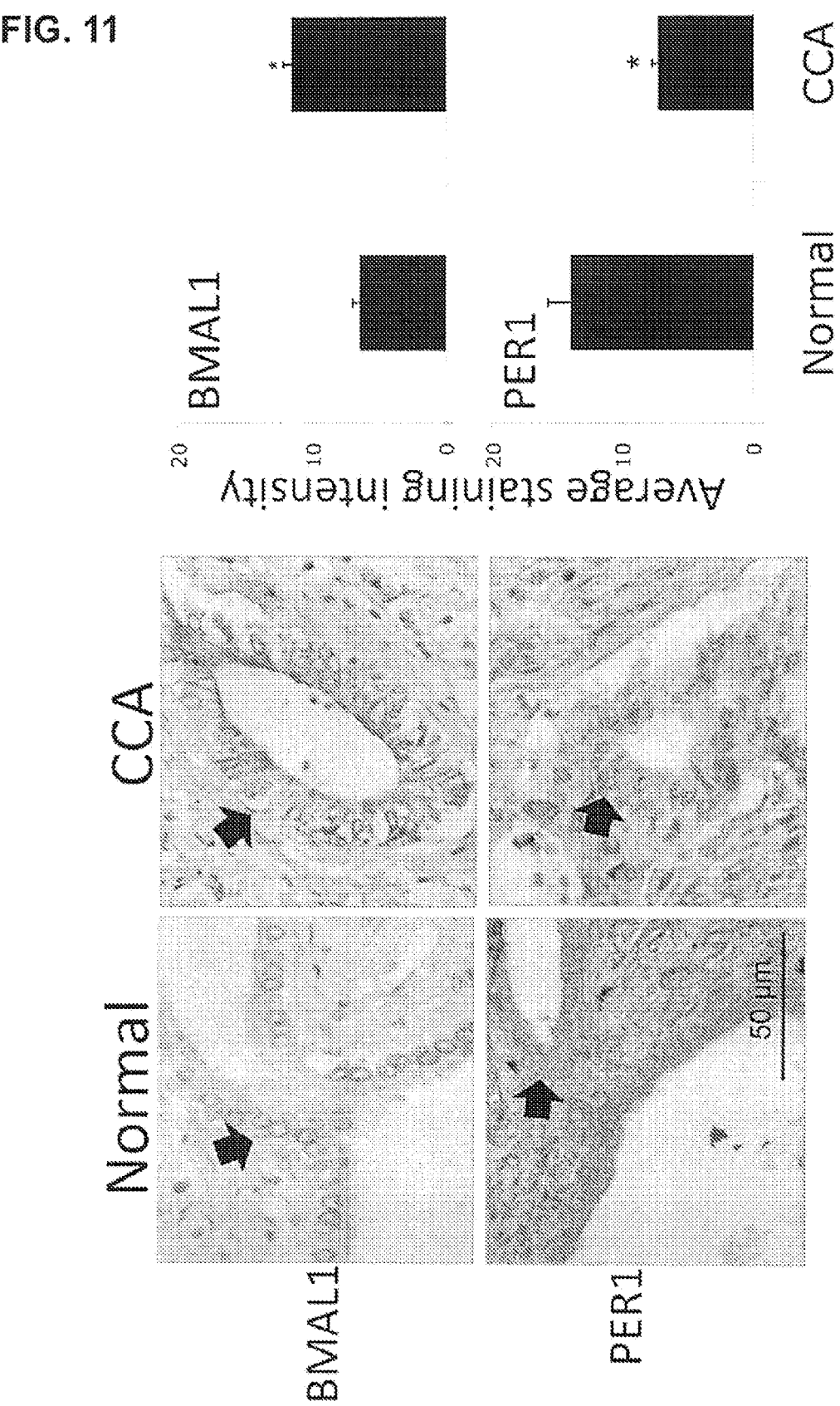
FIG. 11 Evaluation of the expression of the core clock genes, BMAL1 and Per1 in liver biopsy samples from controls and CCA patients. There was enhanced protein expression for BMAL1, and decreased Per1 protein expression in liver biopsy samples from CCA patients compared to controls. Data are mean±SEM of ninety evaluations for CCA patients and four for normal health control. p<0.05 vs. normal health control.

Circadian Gene Expression is Altered in CCA:

Melatonin regulates the expression of circadian genes, which include PER 1, 2 and 3, CRY 1 and 2, BMAL1, and CLOCK5. Circadian genes are linked with the dysregulation of cell cycle control during carcinogenesis. Epidemiologic studies have revealed a link between disruption of circadian rhythms resulting in lack of cell cycle control and cancer development in humans including hepatocellular carcinoma, breast and colon cancer (Hansen, 2001a; Hansen, 2001b). Mice lacking the circadian genes PER1 and 2, CRY1 and 2 are deficient in cell cycle regulation and Per2 mutant mice are cancer-prone (Lee et al., 2010). The loss of CLOCK activity in Cry1−/−/Cry2−/− double mutant mice results in delayed liver regeneration (Matsuo et al., 2003). PER1 expression is down-regulated in human prostate cancer, and overexpression of PER1 in prostate cancer cells resulted in significant growth inhibition and enhanced apoptosis (Cao et al., 2009). Overexpression of PER2 in human pancreatic cancer cells reduced cellular growth, induced apoptosis, and had a synergistic effect with ciplatin (Oda et al., 2009). Down-regulation of PER1 or PER2 were associated with the acceleration of in vivo tumor growth and doubling of the daily amplitude of tumor growth (Yang et al., 2009a; Yang et al., 2009b). BMAL1 levels are upregulated in prostate cancer cells compared to normal prostate tissue (Jung-Hynes, 2010). It has been shown shown that there is reduced gene expression for CLOCK and PER1 in CCA lines, and that melatonin decreases CCA growth by up-regulation of the gene PER1 (Han et al., 2010). There was enhanced protein expression for BMAL1, and decreased PER1 protein expression in liver biopsy samples from CCA patients compared to controls (FIG. 11).

Conclusion: AANAT is down-regulated in CCA. Melatonin secretion is decreased in bile of CCA patients. Overexpression of AANAT reduces the growth of CCA lines. In athymic mice, melatonin inhibits Mz-ChA-1 growth via enhanced biliary expression of AANAT and modulation of clock genes. It was contemplated that (i) the detection of lowered biliary levels of melatonin (observed in CCA) may be a tool for the early detection of CCA; and (ii) drug targeting of AANAT may be important as a novel strategy in the treatment of biliary neoplasms.

Materials

Reagents were purchased from Sigma (St. Louis, Mo.) unless differently indicated. The following antibodies were purchased from Santa Cruz Biotechnology (Santa Cruz, Calif.) unless differently indicated. AANAT (FL-207) is a rabbit polyclonal antibody raised against amino acids 1-207 representing full length AANAT of human origin. ASMT (C-20) is an affinity purified rabbit polyclonal antibody raised against a peptide mapping near the C-terminus of ASMT of human origin. MEL-1A-R (V-15) is an affinity purified goat polyclonal antibody raised against a peptide mapping within an internal region of the melatonin receptor, MT1, of human origin. MEL-1B-R (T-18) is an affinity purified goat polyclonal antibody raised against a peptide mapping within an internal region of MEL-1B-R of mouse origin. Melatonin is a rabbit polyclonal antibody (ab35137, Cbcam, Cambridge, Mass.) raised against melatonin. The ELISA kits for detecting melatonin levels in nonmalignant and CCA cell lines, and serum and bile from controls and CCA patients were purchased from GenWay Biotech Inc. (CA, USA).

In Vitro Studies

Cholangiocarcinoma Cell Lines.

Six human CCA cell lines (Mz-ChA-1, HuH-28, TFK-1, CCLP1, SG231 and HUCC-T1) with different biliary origin were used. Mz-ChA-1 cells (from human gallbladder) (Knuth et al., 1985) were a gift from Dr. G. Fitz (University of Texas Southwestern Medical Center, Dallas, Tex.). HuH-28 cells (from human intrahepatic bile ducts) (Kusaka et al., 1988) and TFK-1 cells (from human extrahepatic bile ducts) (Saijyo et al., 1995) were acquired from Cancer Cell Repository, Tohoku University, Japan. These cells were maintained at standard conditions (Kanno et al. 2001). CCLP-1 (Shimizu et al. 1992), HuCC-T1 (Miyagiwa et al, 1989) and SG231 (Storto P D et al., 1990) (from intrahepatic bile ducts) were a gift from Dr. A. J. Demetris (University of Pittsburg) and cultured as described (Miyagiwa et al., 1989; Shimizu et al., 1992; Storto et al., 1990). The human immortalized, nonmalignant cholangiocyte cell line, H69, (from Dr. G. J. Gores, Mayo Clinic, Minn.) was cultured as described (Grubman et al., 1994).

Expression of AANAT and ASMT in Nonmalignant and CCA Lines and Tissue Arrays.

The expression of AANAT and ASMT was evaluated in: (i) nonmalignant and CCA cell lines by immunofluorescence (DeMorrow et al., 2007), real-time PCR (0.5 mg total RNA) (DeMorrow et al., 2007) and FACS analysis (Onori et al., 2008); and (ii) human tissue arrays from controls and CCA patients by immunohistochemistry (Alpini et al., 2008). The expression of AANAT and ASMT was evaluated by immunofluorescence (Alpini et al., 2008) in cell smears from H69 cells and CCA lines using specific primary antibodies diluted in 1% normal goat serum. Images were taken in a coded fashion with an Olympus fluoview 500 Laser scan microscope with a DP70 digital camera (Tokyo, Japan). Negative controls were done with the omission of the respective primary antibodies.

For real-time PCR analysis (DeMorrow S et al., 2007), RNA was extract from the selected cell lines using RNeasy Mini kit (Qiagen, Inc, Valencia, Calif.) and reverse transcribed using the Reaction Ready™ First Strand cDNA Synthesis kit (SABiosciences, Frederick, Md.). These reactions were used as templates for the PCR assays using SYBR Green PCR Master Mix (SABiosciences) in the real-time thermal cycler (ABI Prism 7900HT sequence detection system) using commercially available primers (purchased from SABiosciences) designed against human AANAT (NM_001088) (Coon S L et al., 1995), ASMT (NM_004043) (Donohue S J et al., 1993) and glyceraldehyde-3-phosphate dehydrogenase (GAPDH, housekeeping) (NM_002046) (Nowak K et al., 1975) genes. A $\Delta\Delta CT$ (delta delta of the threshold cycle) analysis (Mancinelli R et al., 2009) was performed using H69 as the control sample. Data are expressed as relative mRNA levels ±SEM (n=3).

FACS analysis for AANAT and ASMT was performed in H69 and Mz-ChA-1 cells as described (Onori et al., 2008) using a C6 flow cytometer and analyzed by CFlow Software (Accuri Cytometers Inc. Ann Arbor, Mich.). At least 20,000 events in the light-scatter (SSC/FSC) were acquired. The expression of the AANAT and ASMT was identified and gated on FL1-A/Count plots. The relative quantity of AANAT and ASMT (mean selected protein fluorescence) was expressed as mean FL1-A (samples)/mean FL-1A (secondary antibodies only). The standard errors were calculated as (CV FL1-A)×(Mean FL1-A)/SQR(Count-1).

The immunoreactivity for AANAT and ASMT was assessed in commercially available Accumax tissue arrays (lsu Abixs Co., Seoul, Korea) by immunohistochemistry (Alpini G et al., 2008). These tissue arrays contain 48 well-characterized cholangiocarcinoma biopsy samples from a variety of tumor differentiation grades as well as 4 control liver biopsy samples. Light microscopy and immunohistochemistry observations were taken with a BX-40 light microscope (Olympus) with a video-cam (Spot Insight, Diagnostic Instrument, Inc). Semiquantitative analysis was performed using the following parameters. Staining intensity was assessed (in a blinded fashion) on a scale from 1-4 (1=no staining, 4=intense staining) and the abundance of positively stained cells was given a score from 1 to 5 (1=no cells stained, 5=100% stained). The staining index was calculated by the staining intensity multiplied by the staining abundance, which gives a range from 1 to 20 (Alpini et al., 2008).

Evaluation of Melatonin Immunoreactivity in Tissue Arrays.

Measurement of melatonin secretion in nonmalignant and CCA lines and serum and bile from controls and CCA patients. Melatonin immunoreactivity was measured by immunohistochemistry (Alpini et al., 2008) in human biopsy samples from controls and CCA patients from commercially available tissue arrays (lsu Abxis Co) using a specific monoclonal antibody (ab35137, Abcam) against melatonin (see above). Melatonin levels in the supernatant of H69 and Mz-ChA-1 lines were measured as follows using two different approaches. In the first approach, the two lines were trypsinized and the resulting cell pellet was resuspended in 1× Hank's Balanced Salts (HBS) solution ($1\times10^7$ cells/mL). Cells were then incubated in the dark for 24 hr at 37° C. and the amount of melatonin released into the media assayed using a commercially available melatonin ELISA kit (Tamura et al., 2010) according to the manufacturer's instructions (GenWay Biotech Inc.). In the second approach, to determine by ELISA kits (Peschke et al., 2008) the amount of melatonin secreted in the basolateral and apical domains of H69 cells, we plated the cell line on collagen-coated filters of tissue culture inserts to produce a confluent monolayer (Vroman et al., 1996). After 48 hours of incubation the supernatant of the basolateral and apical inserts were collected for evaluation of melatonin levels by ELISA kits (Peschke et al., 2008). Mz-ChA-1 was not used since these cells do not form polarized cell systems (Woo et al., 2008).

Serum and bile were collected from patients with intrahepatic CCA (n=15 for serum and n=13 for bile) and healthy, nonmalignant controls (n=20 for serum, and n=18 for bile). Serum and bile samples were immediately frozen at −80° C. until used for the evaluation of melatonin levels. The melatonin levels in plasma and bile was measured respectively via ELISA kit (GenWay Biotech Inc.) (Tamura E K et al., 2010). The serum and bile human samples were obtained from a tissue bank with de-identified clinical samples from the laboratory of Dr. Pietro Invernizzi (co-author in this manuscript, Department of Internal Medicine, IRRCS Istituto Clinico Humanitas, Rozzano, Milan, Italy). The samples were analyzed in a coded fashion in the laboratory of Dr. Invernizzi.

Melatonin Receptor Expression.

The expression of MT1 and MT2 was evaluated by: (i) immunofluorescence (DeMorrow et al., 2007), real-time PCR (DeMorrow et al., 2007), and FACS analysis (Onori et al., 2008) in the selected nonmalignant and CCA lines; and (ii) immunohistochemistry (Alpini et al., 2008) of tissue arrays of human liver biopsy samples from control and CCA patients (see above for the methodology). For real-time PCR, we used commercially available primers designed against human MT1 (NM_005958, SABiosciences) (Reppert et al., 1994), MT2 (NM_005959, SABiosciences) (Reppert S M et al., 1995) and GAPDH (NM_002046, SABiosciences) (Nowak et al., 1975) genes. A $\Delta\Delta CT$ analysis (Mancinelli et al., 2009) was performed using H69 as the control sample. Data are expressed as relative mRNA levels ±SEM (n=3).

In Vivo Studies.

Experiments were performed to evaluate the in vivo effect of melatonin on the growth of cholangiocarcinoma cell lines implanted in the flanks of athymic mice (Francis H et al., 2009). Male BALB/c 6-wk-old nude (nu/nu) mice (Taconic Farms. Hudson, N.Y.) were kept in a temperature-controlled environment (20-22° C.) with 12-hr light-dark cycles, fed ad libitum standard mouse chow, and with free access to drinking water. Mz-ChA-1 cells ($5\times10^6$) were suspended in 0.2 ml of extracellular matrix gel and injected subcutaneously in the rear flanks of the nude mice. After the establishment of the tumor (one week with a tumor size of ~5 mm$^3$) mice (n=4) were treated with vehicle (5% ethanol in water) or melatonin (4 mg/kg BW, dissolved in 5% aqueous ethanol solution) (Sewerynek et al., 1995) by IP injections three times a week. Tumor variables were measured three times a week by an electronic caliper, and volume was determined as follows: tumor volume (mm$^3$)=0.5×[length (mm)×width (mm)×height (mm)]. The measurements started from the first week when the tumor mass was established. After 43 days of treatment, were anesthetized with sodium pentobarbital (50 mg/kg BW IP) and tumor tissues were harvested from the flanks of the mice. Heart, liver, and kidney tissues were collected for evaluation of organ damage by H&E staining of paraffin-embedded sections (4-5 mm thick). All experiments were conducted under the guidelines of the Scott & White and Texas A&M HSC IACUC Committee. Tumors were allowed to grow until maximum allowable tumor burden was reached as set forth by the Scott & White and Texas A&M HSC IACUC tumor burden policy. Tumor tissues were fixed for 4 hr in 10% buffered formalin and embedded in low-temperature fusion paraffin. Subsequently, sections (4-5 mm) were stained: (i) with H & E for evaluation of necrosis (Francis et al., 2009); and (ii) for PCNA (a marker of proliferation) (Francis et al., 2009), cleaved caspase-3 (for measurement of apoptosis) (Arai et al., 2005), AANAT, ASMT, melatonin, MT1 and MT2 by immunohistochemistry (Francis et al., 2009). Negative controls were obtained by staining the tumor sections with non-immune serum with the omission of the primary antibody. Semiquantitative analysis for these markers was evaluated by image-analysis software, Image-Pro Plus (Media Cybernetics, Silver Springs, Md.) (Lejeune et al., 2008). Three randomly chosen fields were calculated for statistics.

Overexpression of AANAT in Mz-ChA-1 cells. The expression vector containing human AANAT cDNA was purchased from Origene (Rockville, Md.). The 624 bp ORF of AANAT containing a C-terminal MYC/DDK tag was cloned into the pCMV entry and the expression protein was 23.2 kDa. The transfection and the selections of clones were performed as described (Klagge et al., 2010). The plasmid (10 µg) was transfected by nucleofection (Klagge et al., 2010) into Mz-ChA-1 cells according to the manufacturer's instructions. Mz-ChA-1 cells were trypsinized and washed with 1× phosphate buffered saline (PBS) (Gibco Carlsbad, City, Calif.). 1×10$^6$ cells per reaction were resuspended in 100 ml nucleofector solution (Lonza, Basel, Switzerland) at room temperature. Ten mg AANAT cDNA plasmid DNA (Origene, Rockville, Md.) were mixed with 100 ml cell suspension and transferred into a cuvette. The cuvette was inserted into the Nucleofector (Lonza) and cells were pulsed with program U-017. After pulse, the cells were rinsed with 1 ml pre-warmed medium and transferred to a 6-well plate. Culture medium was replaced 24 hours after nucleofection. Stable over expressing AANAT Mz-ChA-1 cells were then selected based on neomycin resistance, and individual colonies were ring-cloned. The overexpression of AANAT in Mz-ChA-1 cells was verified by real-time PCR analysis (Francis et al., 2008). In mock- and stably over expressing AANAT, Mz-ChA-1 cells we evaluated cell proliferation by real-time PCR analysis for PCNA (Francis et al., 2008).

Statistical Analysis.

All data are expressed as mean±SEM. Differences between groups were analyzed by Student's unpaired t-test when two groups were analyzed and ANOVA when more than two groups were analyzed, followed by an appropriate post hoc test.

Example 4

Melatonin Enhances 5-Fluorouracil (5-FU) and Gemcitabine Cytotoxicity In Vitro

In a recent study, Fan et al. demonstrated that melatonin and doxorubicin synergistically induce cell apoptosis in human hepatoma cell lines (Fan et al., 2010). Here it was found that melatonin sensitizes CCA to the cytotoxic effects of 5-fluorouracil (5-FU) and gemcitabine (~2-fold). These findings suggest that melatonin is also a potential adjuvant therapy for CCA.

Example 5

Modulation of the Biliary Expression of AANAT Alters the Proliferative/Apoptotic Responses of Cholangiocytes to Liver Injury In Vivo and In Vitro After bile duct ligation (BDL), there is enhanced biliary growth and bile duct mass (IBDM). Conversely, acute administration of $CCl_4$ induces the functional damage of cholangiocytes by apoptosis and reduction of IBDM. Cholangiocytes secrete several neuroendocrine factors regulating biliary functions by autocrine/paracrine mechanisms. It has been previously shown that melatonin inhibits both in vitro and in vivo the growth of cholangiocytes from BDL rats by modulation of clock genes. It was contemplated that: (i) the key enzyme involved in melatonin synthesis, AANAT, is present in cholangiocytes; and (ii) in vivo and in vitro modulation of biliary AANAT expression alters normal biliary growth and the proliferative/apoptotic responses of cholangiocytes to $CCl_4$.

Methods: Normal rats were treated for 1 wk with AANAT morpholino (to reduce the biliary expression of AANAT) or scrambled morpholino (1 mg/kg BW/day) by a portal vein catheter before receiving a single dose of mineral oil or $CCl_4$ (0.4 ml by gavage 1:1 in mineral oil/100 gm BW). Two days later, in liver sections the following was evaluated: (i) the hepatic expression of AANAT; and (ii) the percentage of TUNEL-positive cholangiocytes, and IBDM. In total liver tissue, the quantitative expression of AANAT, PCNA, Bax and Bcl-2 was studied by qPCR and immunoblots. In mouse cholangiocyte lines (NMC) stably overexpressing AANAT the expression of AANAT and CLOCK genes, melatonin secretion and biliary growth were studied after 48 hr incubation.

Results: In liver sections, it was found that: (i) AANAT was expressed by cholangiocytes and hepatocytes; (ii) the expression of AANAT decreased in cholangiocytes from AANAT morpholino-treated rats receiving vehicle or $CCl_4$; and (iii) in rats treated with morpholino there was enhanced IBDM compared to controls, and absence of biliary apoptosis in response to $CCl_4$. decreased AANAT and increased PCNA expression were found in liver tissue from normal rats receiving AANAT morpholino compared to scrambled morpholino. In liver tissue from rats treated with scrambled morpholino+$CCl_4$ there was enhanced Bax and decreased Bcl-2 and PCNA expression. $CCl_4$-induced changes in Bax, Bcl-2 and PCNA expression were prevented by the in vivo administration of AANAT morpholino. In vitro overexpression of the AANAT gene in NMC increased melatonin secretion, decreased PCNA and Per1 expression but increased the expression of BMAL1, Cry1 and Clock compared to mock-transfected NMC.

Conclusion: It was found that: (i) in vivo down-regulation of biliary AANAT stimulates cholangiocyte proliferation and prevents CCl$_4$-induced ductal apoptosis by an autocrine loop; and (iii) in vitro overexpression of AANAT in NMC decreases the proliferation and modulates clock gene biliary expression in vitro. Local targeting of AANAT in cholangiocytes may be important for the management of cholangiopathies.

Example 6

Melatonin Increases the Expression of miR-141 Reducing the Proliferation of Cholangiocytes by Targeting Clock and Cry1

Background: microRNAs (miRNAs) are small non-coding RNAs that have been implicated in the pathology of cholestatic liver injuries. After bile duct ligation (BDL), there is enhanced biliary proliferation and intrahepatic bile duct mass (IBDM). The inventors have previously shown that: i) cholangiocytes produce melatonin and express Clock genes and that ii) melatonin inhibits in vitro and in vivo the growth of cholangiocytes and cholangiocarcinoma cell lines by modulation of the CLOCK genes. Thus, in certain aspects miRNA regulates the expression of CLOCK genes and subsequently alters the proliferation of cholangiocytes after BDL. Methods: miRNA expression in normal and BDL rat liver was evaluated using hybridization based microRNA microarray. Mouse cholangiocytes (NMCs) were used for the experiments in vitro. mRNA expression was quantitated by real-time PCR analysis and protein expression was detected by Western blot. Results: Microarray expression profiling identified a significant reduction in miR-141 in BDL rat liver, and recovered after melatonin treatment in vivo. Bioinformatics and dual-luciferase reporter assays identified Clock and cryptochrome 1 (Cry1), a blue light-dependent regulator of the circadian feedback loop, as the direct targets of miR-141. Clock expression in BDL rat liver was significantly increased relative to normal controls along with the high proliferation rate. Silencing miR-141 by specific inhibitor in NMCs in vitro significantly increased the expression of both Clock and Cry1 relative to control, whereas the enhanced expressions of both genes were prevented by melatonin treatment. Along with the alterations of clock genes, there was a significant up-regulation of the expression of Ki67, a marker of proliferation compared to control, which as also blocked by melatonin treatment. Suppression of miR-141 also significantly increased cyclin D1 expression, an important regulator of cellular proliferation that helps to initiate transition from the late G1 to the S phase of the cell cycle. Conclusion: The findings indicated that melatonin may modulate miRNA and gene expression as an anti-proliferative mechanism in human bile duct disorders. Targeting of miR-41 during cholestatic liver injuries provides an important therapeutic strategy in the regulation of cholangiocytes proliferation through the regulation of Clock and Cry 1 expression.

Example 7

Suppression of miR-34a Expression by Melatonin Blocks Human Cholangiocarcinoma Tumor Growth and Invasion Background and Aims: MicroRNAs (miRNAs) are a class of small noncoding RNAs that trigger mRNAs translation repression or degradation. Melatonin has been linked to the transcriptional control of key regulatory genes during cancer development. We have previously shown that melatonin inhibits cholangiocarcinoma (CCA) growth in both in vitro and in vivo models. The objective of this study was to evaluate the role of melatonin regulated miRNAs in human CCA.

Methods: miRNA expression in normal human cholangiocytes (HiBECs), and the CCA cell lines Mz-ChA-1 and TFK cells, as well as melatonin treated xenograft tumor tissues were evaluated using a hybridization-based miRNA microarray. The expression of selected mature miRNAs was also assessed by real-time PCR. The effect of selected miRNAs on cell growth and invasion was assessed using miRNA modulators to alter cellular expression. Cell migration and invasion through a matrigel layer was quantitated using commercial assays. BCL-2, period homolog 1 (PER1) and tissue inhibitor of metalloproteinases 3 (TIMP-3) mRNA expression was quantitated by real-time PCR analysis.

Results: miRNA expression profiling identified a significant increase in miR-34a in Mz-ChA-1 and TFK cells relative to HiBEC controls. Treatment with melatonin significantly reduced Mz-ChA-1 xenograft tumor growth in vivo, along with a significant reduction of miR-34a expression. Cell proliferation, migration, invasion and anchorage-independent growth were inhibited by silencing of miR-34a expression in Mz-ChA-1 and TFK cell lines. Enhanced miR-34a expression increased cell motility in normal HiBECs by 178±17%. Bioinformatics and dual-luciferase reporter assays identified PER1 as a direct target of miR-34a. PER1 belongs to the component of the core CLOCK gene family that regulates the circadian rhythm and is known to regulate cell proliferation. We found that PER1 expression in CCA cells was lower than normal HiBECs. Similar to melatonin treatment in vivo, silencing of miR-34a resulted in an increase of PER1 expression levels and reduction in expression of anti-apoptotic protein BCL-2. Furthermore, silencing of miR-34a in Mz-ChA-1 cells also enhanced the expression of TIMP-3, a key mediator involved in the apoptosis of cancer cells and inhibition of extracellular matrix degradation.

Summary and Conclusions: Melatonin-induced silencing of miR-34a in CCA plays a significant role in the blockage of an aggressive growth and invasive phenotype through the modulation of PER1 expression. Our findings suggest that modulation of miR-34a expression by melatonin may represent a novel therapeutic approach for CCA.

Example 8

Decreased Melatonin Synthesis in Cholangiocarcinoma (CCA) Suppresses its Antiproliferative Actions by Upregulation of CLOCK Gene Background: Melatonin is secreted from several extrapineal tissues and cells, such as retina, gastrointestinal tract, and liver and acts both as a hormone of the pineal gland and a local growth regulator in various tissues. Melatonin exerts it effects through two membrane receptors (MT1 and MT2) and is synthesized from serotonin by two enzymes, serotonin N-acetyltransferase (arylalkylamine N-acetyltransferase (AANAT) and acetylserotonin O-methyltransferase (ASMT)). Cholangiocarcinoma (CCA) is a lethal disease afflicting thousands of patients worldwide. The mechanisms regulating CCA growth are poorly understood. The CLOCK gene encodes proteins regulating circadian rhythm and acts as a tumorsuppressor by regulating the balance between growth/apoptosis in several tumors. Embodiments for characterization included the following 1) the levels of melatonin, melatonin biosynthesis enzymes (AANAT and ASMT), melatonin receptors (MT1 and MT2) and the CLOCK gene in normal and CCA lines and CCA tissue, and 2) the effects of melatonin on cell growth.

Methods: Melatonin immunoreactivity, the expression of melatonin biosynthesis enzymes and receptors were assessed by immunohistochemistry in tissue arrays from normal and CCA patients, and by qPCR and immunoblots in intra-hepatic and extra-hepatic CCA cell lines, and a normal cholangiocyte line (H69). Proliferation was evaluated in vitro by MTS assay in CCA lines and H69 after treatment with melatonin (10-7 to 10-11 M, 24-72 hours). In parallel, the expression of CLOCK after melatonin treatment (10-11 M for 48 hours) was assessed in CCA lines and normal cholangiocytes by qPCR.

Results: Melatonin immunoreactivity decreased (~78%) whereas MT1 and MT2 expression increased (~60%) in CCA compared to controls. AANAT significantly decreased (~50%) in CCA samples, and in 5 out of 6 CCA cell lines studied. ASMT decreased (by 60%) significantly in Grade 1 CCA samples when compared to normal samples, and decreased in all CCA cell lines studied. In vitro, melatonin induced a 65% decrease in CCA growth compared to normal cholangiocytes. The levels of the CLOCK gene were increased (~50%) in CCA cells treated with melatonin.

Conclusions: CCA produce lower levels of melatonin and treatment of CCA cells with melatonin decreases the growth of these tumor cells. There is an upregulation of the CLOCK gene associated with the antiproliferative effects induced by melatonin. Local modulation of melatonin synthesis by CCA may be an important autocrine loop for the management of this tumor.

Example 9

Upregulation of Serotonin N-Acetyltransferase (AANAT, the Central Enzyme Involved in the Biliary Synthesis of Melatonin) Decreases Cholangiocarcinoma Growth by an Autocrine Mechanism Cholangiocarcinoma (CCA) is a devastating tumor characterized by late presentation of symptoms and limited treatment options. CCA secretes factors regulating its own proliferation in an autocrine manner. CCA synthesizes and secretes higher amounts of serotonin and dopamine, and blocking their synthesis decreases CCA growth in vitro and in vivo. We have shown that melatonin, a hormone secreted from the pineal gland and extrapineal cells, inhibits in vitro the growth of several intra- and extra-hepatic CCA cell lines. Melatonin is synthesized from serotonin by two enzymes, AANAT and the acetylserotonin O-methyltransferase (ASMT). Thus, we test the hypothesis that melatonin inhibition of CCA growth is due to the upregulation of AANAT, the key enzyme involved in melatonin synthesis. The following was evaluated: (i) expression of AANAT, ASMT and the central clock genes, BMAL1, Per 1, CLOCK and Cry 1, in non-malignant and CCA biopsy human liver samples (by immunohistochemistry) and in several normal (H69 and HIBEC) and intra and extra-hepatic human CCA cell lines (Mz-ChA-1, HuH-28 and TFK-1) by qRT-PCR; and (ii) melatonin secretion by RIA in supernatants (after 24 hr of incubation at 37° C.) from normal and CCA lines. Following transient transfection (70% efficiency) of AANAT cDNA vector in Mz-ChA-1 cells, melatonin secretion (by RIA), cell growth (by PCNA immunoblots), and the expression of clock genes by qRT-PCR were evaluated.

Results: The data shows that: (i) the expression of AANAT, ASMT and melatonin decreased (~80%) in CCA biopsy samples and CCA lines; (ii) melatonin secretion decreased at undetectable levels in CCA supernatants: and (iii) the expression of Per1 decreased (~50%) but BMAL1 expression increased (~50%) in CCA biopsy samples and CCA lines compared to non-malignant biopsy samples and normal cholangiocytes; no changes were observed in the expression of CLOCK and Cry1. Overexpression of AANAT (which induces higher expression/secretion of melatonin) in Mz-Ch-A-1 cells decreases proliferation compared to mock-transfected cells. The changes in Per1 (decrease) and BMAL1 (increase) expression (observed in CCA biopsy samples and CCA lines) was prevented in the Mz-ChA-1 cells overexpressing AANAT compared to mock-transfected cells. Summary/Conclusions: Overexpression of AANAT leads to inhibition of CCA growth by an autocrine loop by differential changes in the clock genes, Pert and BMAL1. In specific embodiments of the invention, drug targeting of AANAT expression is a useful therapeutic approach in the development of biliary neoplasms.

Example 10

Melatonin Inhibits In Vivo Cholangiocarcinoma Growth by Enhanced Biliary Expression of Serotonin N-Acetyltransferase (AANAT) the Key Enzyme Involved in Melatonin Synthesis Cholangiocarcinoma (CCA) is a tumor characterized by late presentation of symptoms and limited treatment options. The hormone, melatonin, modulates circadian rhythms and the growth of various cancers. Melatonin decreases CCA growth in vitro via modulation of clock genes. CCA cells have lower levels of AANAT, but, the functional autocrine role of melatonin synthesis in the regulation of CCA growth is unknown. The aims were to: (i) Assess the expression levels of AANAT in CCA, and the resulting levels of melatonin in the serum and bile of CCA patients and supernatants from CCA lines; (ii) Determine the effects of AANAT overexpression on CCA growth; and (iii) evaluate the in vivo effects of melatonin on CCA growth in athymic mice. Methods: AANAT expression was assessed in liver biopsy samples from CCA patients and controls by immunohistochemistry, and in non-malignant cholangiocytes and intra- and extrahepatic CCA lines by qPCR and immunoblots. Melatonin secretion was assessed in the supernatant of normal and CCA lines, and serum and bile from controls and CCA patients by EIA. Stably overexpressing AANAT in the CCA line, Mz-ChA-1, the expression of AANAT, melatonin secretion, CCA proliferation were evaluated after 48 hr of incubation. In in vivo studies, Mz-ChA-1 cells were injected Sub Q into the hind flanks of nu/nu mice. Tumors were allowed to develop and volumes were measured for 41 days during treatment with saline or melatonin (4 mg/kg BW, IP 3×wk). Tumors were analyzed for AANAT, PCNA, CK-19 and Bax by qPCR and immunoblots. Tumor tissue sections were analyzed for TUNEL, and staining for AANAT, PCNA and CK-19. Results: There was a significant decrease in the expression of AANAT in CCA biopsy samples and CCA lines compared to controls. Melatonin was secreted at significant lower (8-fold) rate in the supernatant of CCA lines compared to controls. Decreased melatonin levels in bile (but not serum) of CCA patients vs. controls. After overexpression of AANAT in CCA cell there was increased melatonin secretion and inhibition of CCA proliferation. In melatonin-treated CCA xenografts there was an increase in AANAT expression (suggesting a positive feed-back loop in melatonin synthesis), a decrease in CCA proliferation and Per1 and Bmal1 expression, and increased apoptosis. Conclusion: AANAT is down-regulated in CCA. Melatonin secretion is decreased in bile of CCA patients. Overexpression of AANAT reduces the growth of CCA lines. In athymic mice, melatonin inhibits Mz-ChA-1 growth via enhanced biliary expression of AANAT and modulation of clock genes. In specific aspects of the invention: (i) the detection of lowered biliary levels of melatonin (observed in CCA) are a tool for the early detection of CCA, in certain aspects of the invention; and (ii) drug targeting of AANAT is important as a novel strategy in the treatment of biliary neoplasms.

Example 11

Increased Synthesis of Melatonin from Pineal Gland and Cholangiocytes (by Prolonged Exposure of Cholestatic Rats to Complete Dark) Leads to Inhibition of Biliary Hyperplasia by Autocrine/Paracrine Mechanisms In cholestatic bile duct ligated (BDL) rats, cAMP-dependent biliary hyperplasia is regulated by several neuroendocrine autocrine/paracrine factors including serotonin and melatonin that are secreted by cholangiocytes. Melatonin is formed from L-tryptophan by the activity of the enzymes, serotonin N-acetyltransferase (AANAT, expressed in liver only by cholangiocytes), and N-acetylserotonin O-methyltransferase, and is produced by the pineal gland as well as small intestine and liver. Melatonin (whose synthesis is higher at dark) is a key circadian timing signal regulating the expression of clock genes and function in a number of cells. It has been previously shown that: (i) chronic administration of melatonin increased melatonin serum levels and inhibits cholangiocyte hyperplasia in BDL rats by downregulation of the clock genes, CLOCK, BMAL1, CRY1, and PER1; and (ii) downregulation of AANAT biliary expression (by Vivo-morpholino) increases cholangiocyte hyperplasia in rats. No information exists regarding possible effects of dark therapy in the regulation of biliary hyperplasia. In some embodiments of the invention, prolonged exposure to complete dark increases melatonin synthesis by the pineal gland and cholangiocytes leading to inhibition of cholangiocyte growth during cholestasis by both autocrine/pathways mechanisms.

Methods: Normal and BDL (immediately after surgery) rats were housed for 12:12 hr light/dark cycles or complete dark for 1 week before evaluating: (i) serum levels of melatonin, bilirubin and transaminases; (ii) intrahepatic bile duct mass (IBDM) in liver sections and secretin effects on bile secretion (a functional index of biliary growth); (iii) the mRNA expression of AANAT in pineal gland, small intestine and cholangiocytes, and the expression of PCNA and clock genes in cholangiocytes by qPCR; and (iv) the levels of melatonin in the medium of short-term cultures of cholangiocytes.

Results: In BDL rats exposed to continuous dark there was: (i) enhanced melatonin serum levels and reduced levels of bilirubin and transaminases; (ii) IBDM and lack of choleretic response to secretin; (iii) enhanced AANAT expression mostly in pineal gland and cholangiocytes and reduced expression of PCNA and clock genes in cholangiocytes; and (iv) increased secretion of melatonin in cholangiocyte medium compared to rats exposed to light/dark cycles. No significant effects were observed in normal rats.

Summary/conclusion: Exposure of cholestatic rats to prolonged dark increases the synthesis of melatonin from pineal gland and cholangiocytes leading to inhibition of biliary hyperplasia likely by both autocrine/paracrine mechanisms. These findings highlight a critical need for the further evaluation of alterations of the dark/light cycle in the progression of cholestatic liver injury and as a concomitant therapeutic approach for patients with liver diseases.

Example 11

Modulation of the Biliary Expression of Arylalkylamine N-Acetyltransferase Alters the Autocrine Proliferative Responses of Cholangiocytes Abstract Background & Aims:

Secretin stimulates ductal secretion by interaction with receptors (SR) activating cAMP$\Rightarrow$CFTR$\Rightarrow$Cl$^-$/HCO$_3^-$ AE2, a pathway that increases during biliary hyperplasia. Cholangiocytes secrete several neuroendocrine factors regulating biliary functions by autocrine mechanisms. Melatonin inhibits biliary growth and secretin-stimulated choleresis in cholestatic rats by interaction with melatonin type 1 (MT1) receptors via downregulation of cAMP signaling. No data exists regarding the role of melatonin synthesized locally by cholangiocytes in the autocrine regulation of biliary growth and function. Methods: In embodiments of the present invention, the following were evaluated: (i) arylalkylamine N-acetyltransferase (AANAT, the enzyme regulating melatonin synthesis) expression in cholangiocytes; and (ii) the effect of local modulation of biliary AANAT expression on the autocrine proliferative/secretory responses of cholangiocytes. Results: In the liver, only cholangiocytes expressed AANAT. AANAT expression decreased in rats treated with AANAT Vivo-Morpholino compared to control. The decrease in AANAT expression and subsequent lower melatonin secretion by cholangiocytes was associated with increased biliary proliferation and increased expression of SR, CFTR, Cl$^-$/HCO$_3^-$ AE2 and VEGF-A/C. Overexpression of AANAT in cholangiocyte lines decreased the basal proliferative rate and expression of PCNA, SR, CFTR, Cl$^-$/HCO$_3^-$ AE2, and VEGF-A/C and ablated secretin-stimulated biliary secretion in these cells. Conclusion: Modulation of melatonin synthesis is useful for the management of cholangiopathies.

Introduction

Cholangiocytes modify canalicular bile before it reaches the duodenum through a series of secretory/absorptive events regulated by gastrointestinal hormones including secretin (Kanno et al., 2001; Alpini et al., 1988). Secretin stimulates bile secretion by interaction with secretin receptors (SR, expressed only by large cholangiocytes in the liver) (Alpini et al., 1994) by increased cyclic adenosine 3',5'-monophosphate (cAMP) levels (Kanno et al., 2001; Alpini et al., 1997), opening of cystic fibrosis transmembrane conductance regulator (CFTR) (Alpini et al., 1997) and activation of the chloride bicarbonate anion exchanger 2 (Cl$^-$/HCO$^-_3$ AE2) (Alvaro et al., 1993) stimulating bicarbonate secretion (Alpini et al., 1988).

Cholangiocytes are the target cells in human cholangiopathies (Alpini et al., 2001) and animal models of cholestasis (e.g., bile duct ligation, BDL) that induces biliary hyperplasia (Alpini et al., 1988). While biliary hyperplasia is coupled with enhanced functional expression of SR, CFTR, Cl$^-$/

HCO$^-_3$ anion AE2 and secretory responses to secretin, damage of bile ducts is associated with functional loss of these parameters (Alpini et al., 1988; Alpini et al., 1994; Glaser et al., 2010; Mancinelli et al., 2010). The balance between biliary proliferation/damage is regulated by several neuroendocrine autocrine factors including vascular endothelial growth factor-A/C (VEGF-A/C) and serotonin (Alvaro et al., 2007; Marzioni et al., 2005; Gaudio et al., 2006).

Melatonin is an indole formed enzymatically from L-tryptophan by the activity of the enzymes, serotonin N-acetyltransferase (AANAT), and N-acetylserotonin O-methyltransferase (ASMT) (Iuvone et al., 2005), and is produced by the pineal gland as well as small intestine and liver (Reiter, 1991; Bubenik, 2002). Melatonin ameliorates liver fibrosis and systemic oxidative stress in cholestatic rats (Esrefoglu et al., 2005; Tahan et al., 2010). Melatonin inhibits cholangiocyte hyperplasia and secretin-stimulated ductal secretion in BDL rats by interaction with type 1 (MT1) receptors by decreased PKA phosphorylation (Renzi et al., 2011). No information exists regarding the role of melatonin in the autocrine regulation of biliary growth. The present example demonstrates evaluation of the following: (i) the expression of AANAT by cholangiocytes; and (ii) the effects of in vivo and in vitro modulation of biliary AANAT and melatonin secretion on the proliferative/secretory responses of cholangiocytes by autocrine signaling.

Methods and Materials
Materials

Reagents were purchased from Sigma-Aldrich (St. Louis, Mo.) unless otherwise indicated. The antibodies used are detailed below. The RNeasy Mini Kit for total RNA purification was purchased from Qiagen (Valencia, Calif.). The RIA kits for the determination of cAMP levels were purchased from GE Healthcare (Arlington Heights, Ill.). Vivo-Morpholino sequences were designed and purchased from Gene-tools LCC (Philomath, Oreg.).

Animal Models

Male Fischer 344 rats (150-175 gm) were purchased from Charles River Laboratories (Wilmington, Mass.) and housed at 22° C. with 12:12 hr light/dark cycles. The animals had free access to standard chow and drinking water. In addition to normal (sham) rats, we used animals that immediately after BDL were treated for 1 week with tap water (vehicle) or melatonin (20 mg/L in tap water) (Renzi et al., 2011). This dose corresponds to a melatonin intake of approximately 2 mg/gm BW per day per rat. This model was previously validated and it was demonstrated that chronic administration of melatonin to rats increases the serum levels of this hormone (Renzi et al., 2011). Animal experiments were performed in accordance with a protocol approved by the Scott & White and Texas A&M Health Science Center IACUC.

In separate experiments, normal rats treated with Vivo-Morpholino sequences of AANAT (5'-GTTCCCCA-GCTTTGGAAGTGGTCCC (SEQ ID NO:1), to reduce the biliary expression of AANAT) or Morpholino mismatched (5'-GTTCCCGACCTTTGCAACTCGTCCC (SEQ ID NO:2)) (Gene Tools LCC) (1 mg/Kg BW/day) for 1 week via an implanted portal vein catheter. Serum, liver tissue, cholangiocytes, kidney, spleen, small intestine, stomach and heart were collected. Since our goal was to knock-down AANAT expression in the liver without inhibiting AANAT expression in other organs, we used a lower dose (1 mg/Kg/day) of Vivo-Morpholino than that described in the original study (3.0 mg/kg/day (Arora et al., 2002). This approach minimizes the amount of Vivo-Morpholino that circulates outside of the liver after slow infusion into the portal vein. See below for the surgical procedure for the implantation of the portal vein catheter by which AANAT Vivo-Morpholino or Morpholino mismatched was administered.

Freshly Isolated and Immortalized Cholangiocytes

Pure cholangiocytes were isolated by immunoaffinity separation using an antibody (by Dr. R. Faris, Brown University, Providence, R.I.) recognizing an unidentified antigen expressed by all cholangiocytes (Ishii et al., 1989). The in vitro studies were performed in immortalized large cholangiocytes (MCL, derived from large bile ducts), which are functionally similar to freshly isolated large cholangiocytes (Glaser et al., 2010; Ueno et al., 2003). MCL was cultured as described (Glaser et al., 2010).

Expression of AANAT in Liver, Cholangiocytes, Pineal Gland and Small Intestine

The following was evaluated: (i) the expression of AANAT in liver sections and cholangiocytes from the selected groups of animals; and (ii) the effectiveness of the AANAT Vivo-Morpholino in lowering the expression of AANAT in cholangiocytes was determined. The expression of AANAT in liver sections (4 μm thick) was determined by semiquantitative immunohistochemistry (Mancinelli et al., 2010. Immunohistochemical observations were taken in a coded fashion by a BX-51 light microscope (Olympus, Tokyo, Japan) with a Videocam (Spot Insight; Diagnostic Instrument, Inc., Sterling Heights, Mich.) and analyzed with an Image Analysis System (IAS; Delta Sistemi, Rome, Italy). Negative controls were included.

The expression of AANAT was evaluated by real-time PCR (Renzi et al., 2011). The rationale for performing the Vivo-Morpholino studies (n=3) also in total liver is based on the fact that: (i) these treatments are expensive and cholangiocyte yield from three rats is very low; and (ii) AANAT is only expressed by cholangiocytes. To evaluate the mRNA expression of AANAT (0.5 μg RNA), we used the RT$^2$ Real-Time assay from SABiosciences (Frederick, Md.) (Francis et al., 2008). A $\Delta\Delta C_T$ (delta delta of the threshold cycle) analysis was performed (Francis et al., 2008) using normal cholangiocytes as control sample. Data were expressed as relative mRNA levels ±SEM of the selected gene to glyceraldehyde-3-phosphate dehydrogenase (GAPDH) ratio. The primers for rat AANAT and GAPDH genes (SABiosciences) were designed according to the NCBI GenBank Accession numbers NM_012818 (AANAT) and NM_017008 (GAPDH).

Measurement of Melatonin Levels in Serum and Cholangiocyte Supernatants

Melatonin levels in serum and medium of primary cultures of isolated cholangiocytes were determined by ELISA kits (Genway, San Diego, Calif.). Supernatants were obtained from cholangiocytes (1×10$^7$ cells/ml) that were incubated for 6 hours at 37° C. (Glaser et al., 2008).

Evaluation of Biliary Proliferation and Apoptosis and Serum Levels of Transaminases, Alkaline Phosphatase and Bilirubin Biliary proliferation was determined by measurement of the percentage of PCNA-positive cholangiocytes by immunohistochemistry, and intrahepatic bile duct mass (IBDM) by immunohistochemistry for CK-19 (Mancinelli et al., 2010). Biliary apoptosis was evaluated by semiquantitative terminal deoxynucleotidyltransferase biotin-dUTP nick-end labeling (TUNEL) kit (Chemicon International, Inc., Temecula, Calif.) (Mancinelli et al., 2010). IBDM was determined as the area occupied by CK-19 positive-bile duct/total area×100 (Mancinelli et al., 2010). The morphological changes/damage in liver, spleen, kidney, heart, stomach, and small intestine were evaluated from AANAT Vivo-Morpholino- or mismatch-treated rats by H&E staining. The serum levels of the transaminases, glutamate pyruvate transaminases (SGPT) and glutamic oxaloacetic transaminase (SGOT), alkaline phosphatase (ALP) and total bilirubin were evaluated using a Dimension RxL Max Integrated Chemistry system (Dade Behring Inc., Deerfield Ill.), Chemistry Department, Scott & White.

Evaluation of PCNA, SR, CFTR, $Cl^-/HCO_3^-$ AE2, VEGF-A/C in Liver Tissue and Cholangiocytes By real-time PCR (Francis et al., 2008), the expression of PCNA, SR, CFTR, $Cl^-/HCO_3^-$ AE2, VEGF-A/C was evaluated in total RNA from: (i) cholangiocytes from normal rats, and BDL rats treated with melatonin; and (ii) liver tissue and cholangiocytes from rats treated with mismatch or AANAT Vivo-Morpholino for 1 week. A $\Delta\Delta C_T$ analysis was obtained using normal cholangiocytes or normal total liver as control samples (Francis et al., 2008). The primers for rat PCNA, SR, CFTR, $Cl^-/HCO_3^-$ AE2, VEGF-A/C (SABiosciences) were designed according to the NCBI GenBank Accession numbers: NM_022381 (PCNA); NM_031115 (SR); NM_017048 ($Cl^-/HCO_3^-$ AE2); XM_001059206 (CFTR); NM_031836 (VEGF-A); and NM_053653 (VEGF-C). The percentage of cholangiocytes positive for SR, CFTR, $Cl^-/HCO_3^-$ AE2 and VEGF-A/C was evaluated in liver sections: when 0%-5% of bile ducts were positive a negative score was assigned; a +/−score was assigned when 6%-10% of ducts were positive; a +score was assigned when 11%-30% of bile ducts were positive (Glaser et al., 2009).

Overexpression of AANAT in MCL and Measurement of Secretory Parameters

MCL were transfected using an AANAT cDNA clone vector from OriGene Technologies, Inc. (Rockville, Md.) that confers resistance to geneticin for the selection of stable transfected cells. Transfected cells were selected by the addition of 10 µL/mL geneticin into the media and the selection process was allowed to continue for 4-7 days (Mancinelli et al., 2009). Surviving cells (MCL-AANAT) were assessed for the relative expression of AANAT compared to the control transfected cells (MCL-puro) by real-time PCR (Francis et al., 2008) and FACS analysis (Onori et al., 2010), and the clone with the greatest degree of overexpression was selected. The following were measured: (i) AANAT mRNA and protein expression (by real-time PCR and FACS) (Francis et al., 2008; Onori et al., 2010) and melatonin secretion (after 6 hour incubation) by ELISA kits; (ii) basal proliferative activity by real-time PCR and immunoblots for PCNA (Francis et al., 2008); (iii) mRNA and/or protein expression of SR, CFTR, $Cl^-/HCO_3^-$ AE2, VEGF-A/C by real-time PCR (Francis et al., 2008) and FACS (Onori et al., 2010); and (iv) the effect of secretin on cAMP levels (Glaser et al., 2009; Francis et al., 2007) and $Cl^-$ efflux (Alpini et al., 1997). The primers for mouse PCNA, SR, CFTR, $Cl^-/HCO_3^-$ AE2, VEGF-A/C(SABiosciences) were designed according to the NCBI GenBank® Accession numbers: NM_011045 (PCNA); NM_001012322 (SR); NM_021050 (CFTR); NM_009207 ($Cl^-/HCO_3^-$ AE2); NM_009505 (VEGF-A); NM_009506 (VEGF-C); NM_009591 (AANAT).

Statistical Analysis

All data are expressed as mean±SEM. Differences between groups were analyzed by Student's unpaired t-test when two groups were analyzed and ANOVA when more than two groups were analyzed, followed by an appropriate post hoc test.

Antibodies

The following antibodies were purchased from Santa Cruz Biotechnology Inc. (Santa Cruz, Calif.): (i) AANAT (FL-207) a rabbit polyclonal antibody against amino acids 1-207 representing full length AANAT of human origin; (ii) mouse monoclonal antibody against rat proliferating cell nuclear antigen (PCNA); (iii) secretin receptor (C 20) an affinity purified goat polyclonal antibody against a peptide mapping at the C-terminus of secretin receptor of human origin; (iv) VEGF-A (JH121) a mouse monoclonal antibody recognizing full length VEGF-A of human origin; and (v) VEGF-C (H-190) a rabbit polyclonal antibody against amino acids 230-419 of VEGF-C of human origin. The rabbit anti-rat $Cl^-/HCO_3^-$ AE2 antibody was purchased from Alpha Diagnostic International Inc. (San Antonio, Tex.). The mouse monoclonal CFTR Ab-4 (M3A7) was purchased from Thermo Scientific (Fremont, Calif.). The mouse anti-cytokeratin-19 (CK-19) antibody (clone RCK105) was purchased from Caltag Laboratories Inc. (Burlingame, Calif.).

Surgical Procedure

The surgical procedure for the implantation of the portal vein catheter (by which AANAT Vivo-Morpholino or Morpholino mismatched was administered) was performed by Charles River under the Charles River's Institutional Animal Care and Use Committee Regulations. The surgical procedure for the implantation of the catheter is described in detail at the Charles River, (http://www.criver.com/SiteCollection-Documents/rm_ss_r_portal_vein_cath.pdf). An abdominal midline incision was made extending above the xyphoid cartilage, the cecum was pulled out and the mesenteric vein is identified. A 5 mm section of the vessel was isolated where the catheter was inserted and secured in place by tying the loose ligature around the catheterized vessel. The cecum was replaced into the abdominal cavity. Then, a hole was made in the right abdominal wall through which the free end of the catheter was passed. The catheter was then secured by suture to the abdominal wall. A small incision was made in the scapular region to serve as the exit site of the catheter. The catheter was subcutaneously tunneled and exteriorized through the scapular incision. A stay suture was placed in the scapular area. Potency was tested, and the catheter filled with a locking solution and sealed with a plug. A subcutaneous skin pocket was made cranially. The excess length of catheter was tucked into the skin pocket.

Results

Expression of AANAT

Figure 12A:
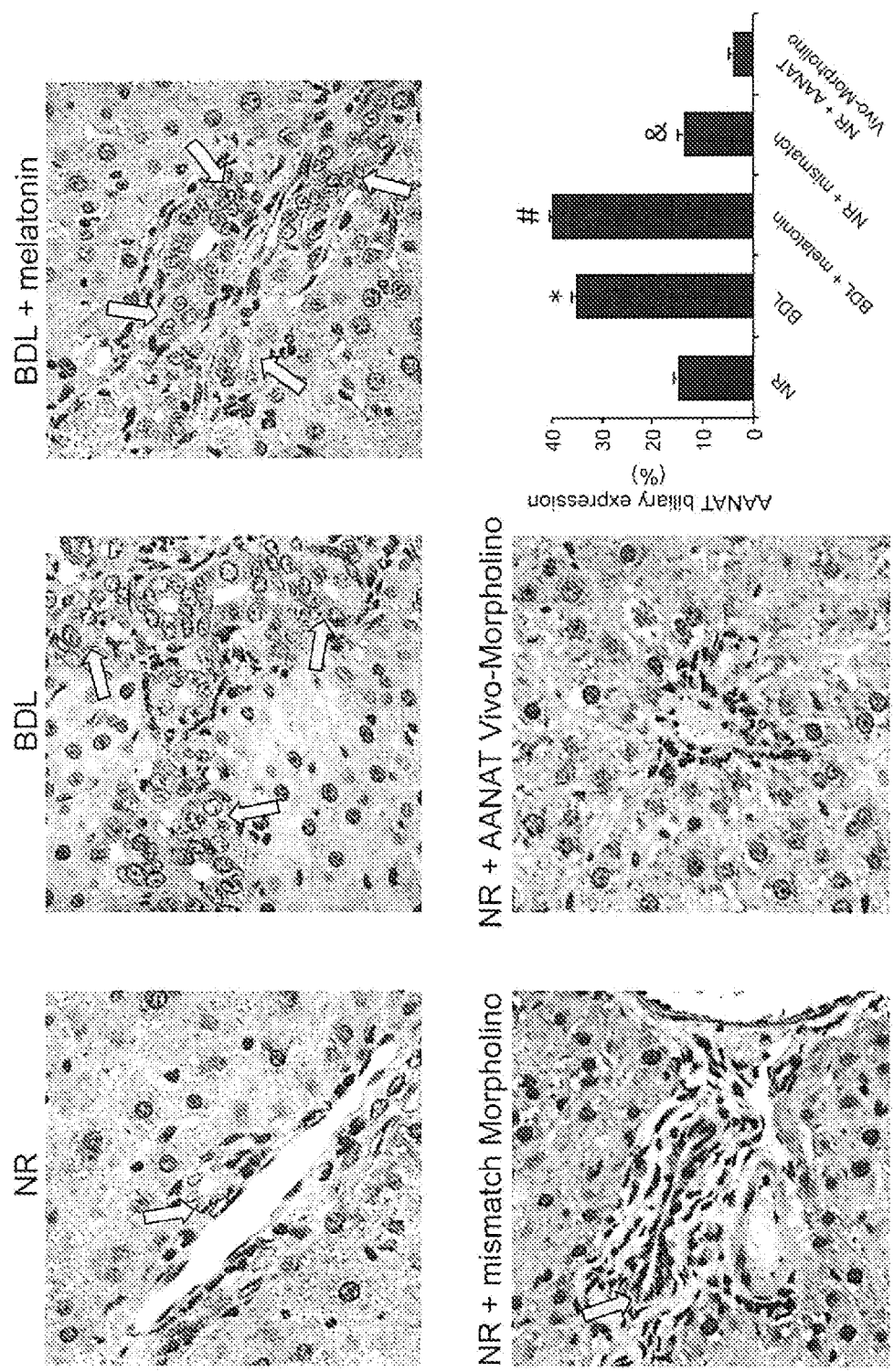
FIG. 12 [A] AANAT biliary expression was low in normal rats and increased after BDL. The expression of AANAT increased in ducts from BDL rats treated with melatonin and decreased in bile ducts from rats treated with AANAT-Vivo Morpholino. Orig. magn. ×40. *p<0.05 vs. the corresponding value of normal rats. #p<0.05 vs. the value of BDL rats. &p<0.05 vs. the value of rats treated with mismatch Morpholino. [B-C] AANAT mRNA expression increased in BDL cholangiocytes, and in cholangiocytes from BDL rats treated with melatonin compared to controls [B] and decreased in liver samples and cholangiocytes from rats treated with AANAT Vivo-Morpholino compared to controls [C]. [D] The mRNA levels of AANAT increased in the pineal gland and intestine of rats treated with AANAT Vivo-Morpholino compared to controls. Data are mean±SEM of 4 evaluations. *p<0.05 vs. the corresponding value of normal rats. #p<0.05 vs. the value of BDL rats. &,@p<0.05 vs. the value of rats treated with mismatch Morpholino. NR=normal rat.
Figures 12B, 12C, 12D:
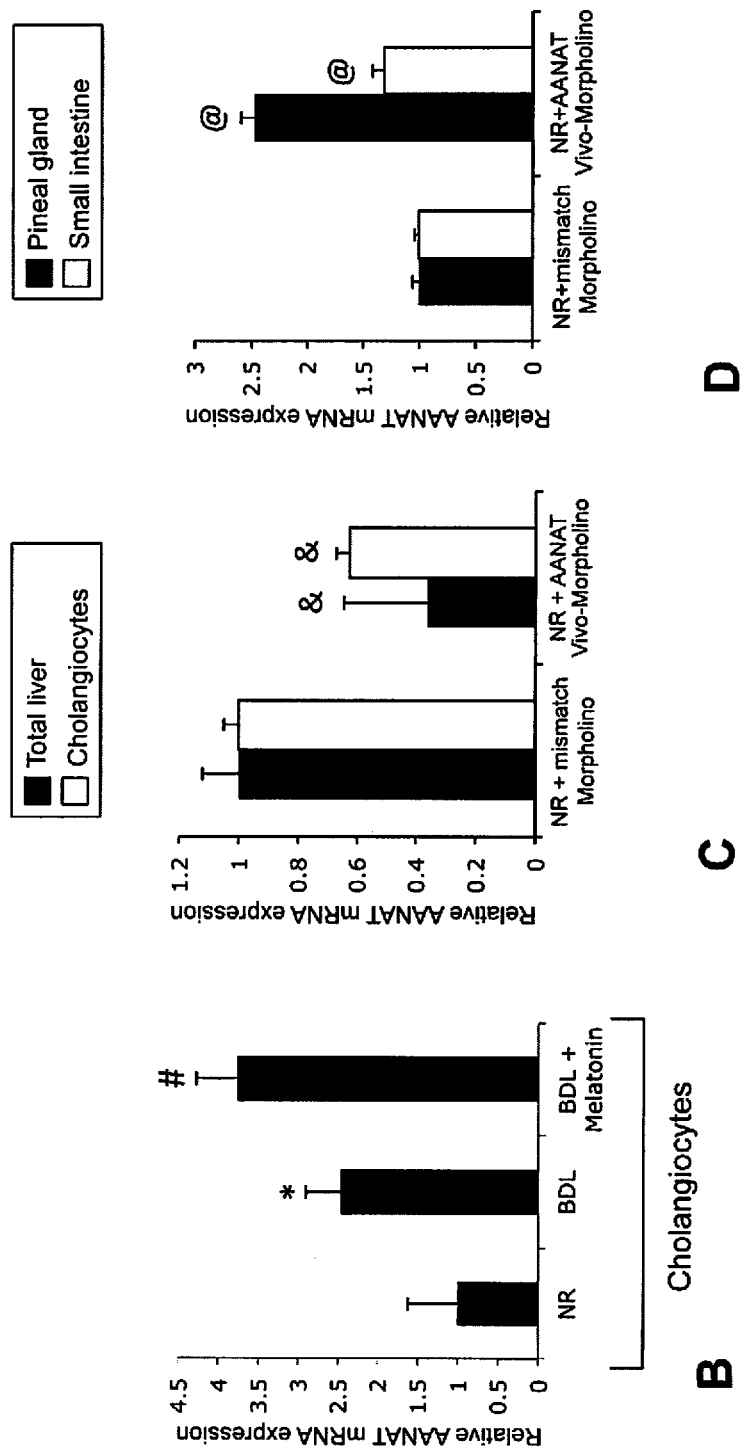

The expression of AANAT was low in normal bile ducts and increased following BDL (FIG. 12A and Table 5). Normal hepatocytes were negative for AANAT; a weak immunoreactivity was observed in BDL hepatocytes (FIG. 12A). The expression of AANAT increased in bile ducts from BDL rats treated with melatonin (FIG. 12A). AANAT biliary expression was reduced in rats treated with AANAT Vivo-Morpholino compared to controls (FIG. 12A). AANAT mRNA expression: (i) increased in BDL compared to normal cholangiocytes, and in cholangiocytes from BDL rats treated with melatonin (FIG. 12B); and (ii) decreased in liver samples and cholangiocytes from rats treated with AANAT Vivo-Morpholino compared to controls (FIG. 12C). AANAT mRNA levels increased in pineal gland and small intestine from rats treated with AANAT Vivo-Morpholino compared to controls (FIG. 12D).

Melatonin Levels in Serum and Cholangiocyte Supernatants

Melatonin serum levels increased in rats treated with AANAT Vivo-Morpholino compared to controls (Table 5). Although AANAT biliary expression decreased in rats treated with AANAT Vivo-Morpholino (FIG. 12B-C and Table 5), the increase in melatonin serum levels observed in these rats was likely due to enhanced expression of AANAT (and subsequent increased melatonin secretion) in other tissues/organs such as pineal gland and small intestine, which constitutively express AANAT (Bubenik, 2002; Humphries et al., 2007). Melatonin levels decreased in the supernatant of cholangiocytes from rats treated with AANAT Vivo-Morpholino compared to controls (Table 5).

TABLE 5

Evaluation of melatonin levels in serum and cholangiocyte supernatant, and the percentage of PCNA-positive cholangiocytes, IBDM and the percentage of apoptotic cholangiocytes.

| Parameters | Normal rats + mismatch Morpholino | Normal rats + AANAT Vivo-Morpholino |
|---|---|---|
| Melatonin serum (pg/ml) | 46.4 ± 10.1 (n = 4) | 58.4 ± 8.7$^a$ (n = 4) |
| Melatonin supernatant (pg/ml) | 5.8 ± 0.6 (n = 3) | 3.2 ± 0.2$^a$ (n = 3) |
| % PCNA-positive cholangiocytes | 8.00 ± 0.7 | 8.98 ± 0.6* |
| % IBDM | 0.30 ± 0.04 | 0.45 ± 0.10* |
| % apoptotic cholangiocytes | <5 | <5 |

Data are mean ± SEM. Values are obtained from the immunohistochemical evaluation of 10 randomly selected fields of 3 slides.
$^a$p < 0.05 vs. the corresponding value of normal rats treated with mismatch Morpholino.

Biliary Proliferation/Apoptosis and Serum Levels of Transaminases, Alkaline Phosphatase and Bilirubin In liver sections from rats treated with AANAT Vivo-Morpholino there was enhanced percentage of PCNA-positive cholangiocytes and IBDM compared to controls (Table 5). There was evaluation of the % of PCNA-positive cholangiocytes and IBDM in liver sections. In rats treated with AANAT Vivo-Morpholino there was enhanced % of PCNA-positive cholangiocytes and IBDM compared to controls. The % of PCNA positive cholangiocytes was assessed in 3 sections per each group. Positive cells were counted in six non-overlapping fields for each slide. The % surface occupied by CK-19 positive cholangiocytes (IBDM) was assessed in 3 for each group. No changes in biliary apoptosis (Table 5) and serum levels of transaminases, ALP and bilirubin were observed in the two groups of animals (Table 6).

TABLE 6

Evaluation of serum levels of melatonin, transaminases and bilirubin in the selected groups of animals.

| Groups | SGPT (Units/L) | SGOT (Units/L) | ALP (Units/L) | Total bilirubin (mg/L) |
|---|---|---|---|---|
| Normal rats + mismatch Morpholino XIX. | 67.75 ± 4.6 (n = 4) | 120.5 ± 10.5 (n = 4) | 230.7 ± 9 (n = 4) | <0.1 (n = 4) |

TABLE 6-continued

Evaluation of serum levels of melatonin, transaminases and bilirubin in the selected groups of animals.

| Groups | SGPT (Units/L) | SGOT (Units/L) | ALP (Units/L) | Total bilirubin (mg/L) |
|---|---|---|---|---|
| Normal rats + AANAT Vivo-Morpholino XX. | 72.25 ± 0.2 (n = 4) | 148.5 ± 22.5 (n = 4) | 230.2 ± 5.2 (n = 4) | <0.1 (n = 4) |

Data are mean ± SEM.
SGOT = serum glutamic oxaloacetic transaminases;
SGPT = serum glutamate pyruvate transaminases;
ALP = alkaline phosphatase.

No lobular damage or necrosis was observed. A small, similar degree of portal inflammation was observed in the two groups of animals. None of the organs analyzed by H&E staining showed structural damage, necrosis or inflammation. Indeed, morpholinos are free of off-target effects since they are not degraded in biological systems and do not generate degradation products toxic to cells (Summerton et al., 2007).

Effect of AANAT Knockdown on the Expression of PCNA, SR, CFTR and $Cl^-/HCO_3^-$ AE2 and VEGF-A/C The expression of SR, CFTR, $Cl^-/HCO_3^-$ AE2 and VEGF-A/C increased in bile ducts from rats treated with AANAT Vivo-Morpholino compared to controls (Table 7).

TABLE 7

Evaluation of the immunoreactivity of cholangiocytes to SR, CFTR, $Cl^-/HCO_3^-$ AE2, VEGF-A/C.

| Groups | SR | CFTR | $Cl^-HCO_3^-$ AE2 | VEGF-A | VEGF-C |
|---|---|---|---|---|---|
| Normal rats + mismatch Morpholino XXI. | +/− | −/+ | +/− | +/− | −/+ |
| Normal rats + Vivo Morpholino XXII. | + | + | + | + | + |

Figure 13A:
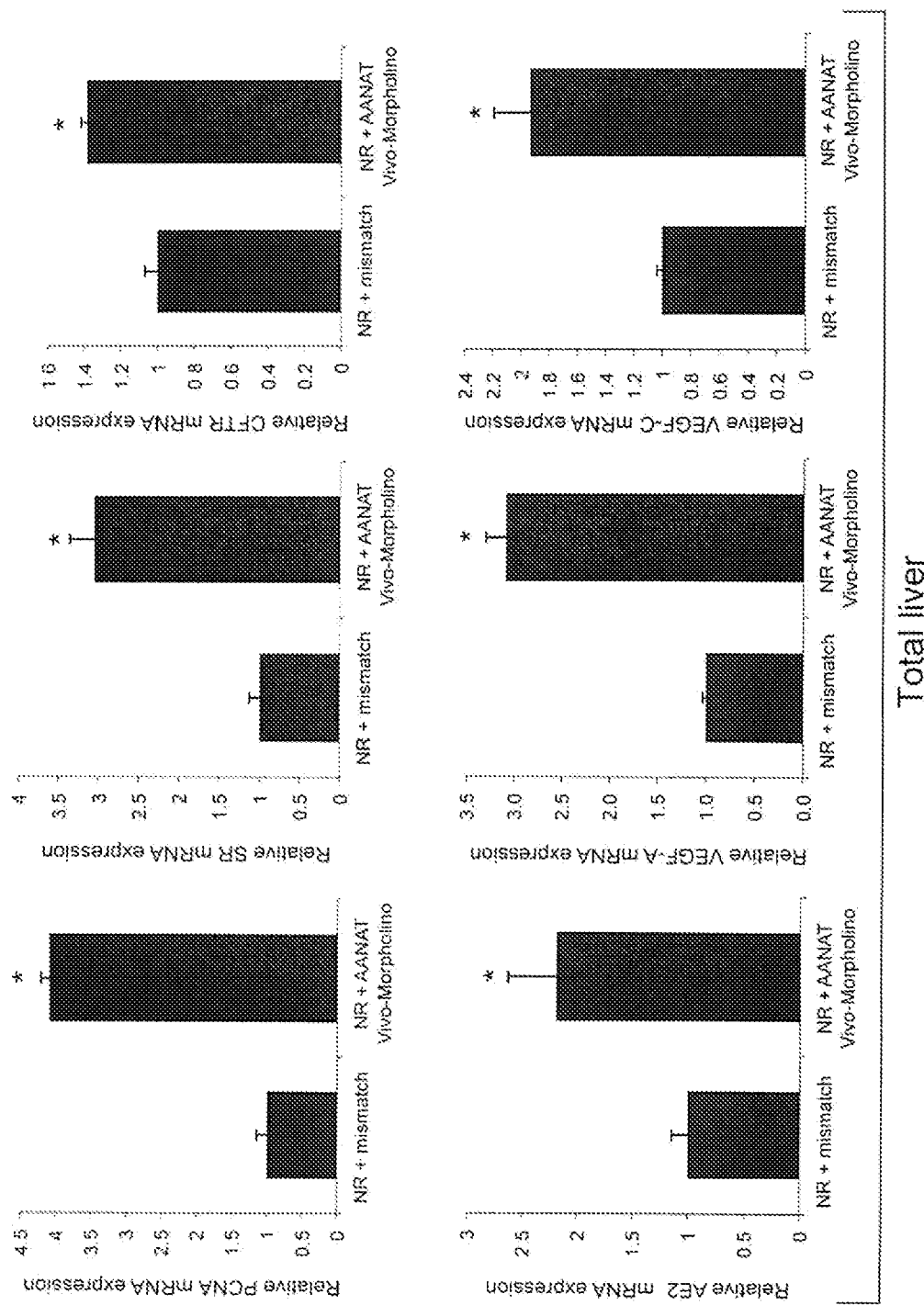
FIG. 13 [A-B] Effect of AANAT knock-down on the mRNA expression of PCNA, SR, CFTR and $Cl^-/HCO_3^-$ AE2 and VEGF-A/C in liver samples and cholangiocytes. Data are mean±SEM of 3 experiments. *p<0.05 vs. the corresponding value of normal rats treated with mismatch Morpholino. AE2=$Cl^-/HCO_3^-$ AE2.
Figure 13B:
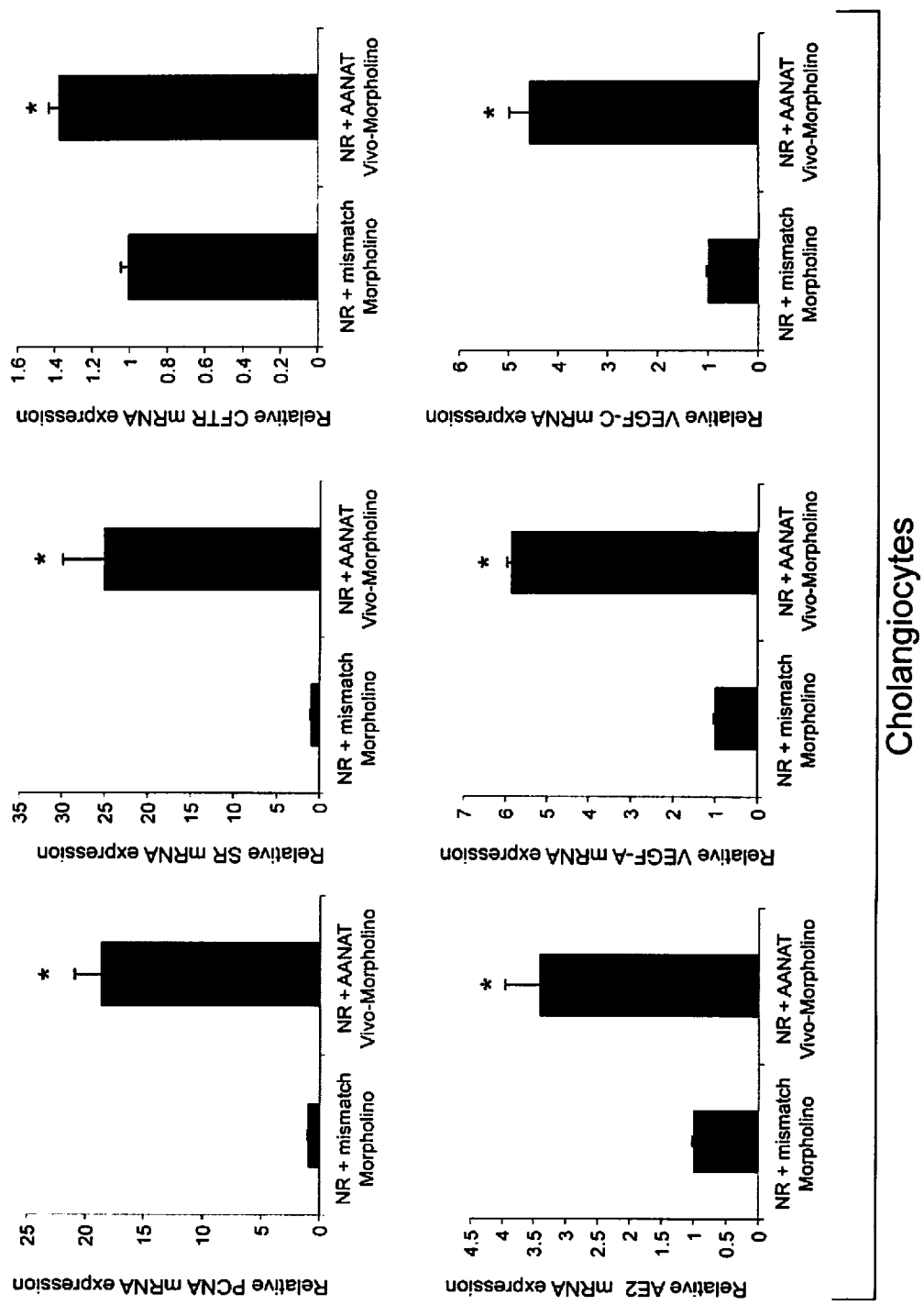

There was increased expression of PCNA, SR, CFTR and $Cl^-/HCO_3^-$ AE2 and VEGF-A/C in total liver and cholangiocytes from normal rats treated with AANAT Vivo-Morpholino compared to controls (FIG. 13A-B).

Figures 14A, 14B, 14C:
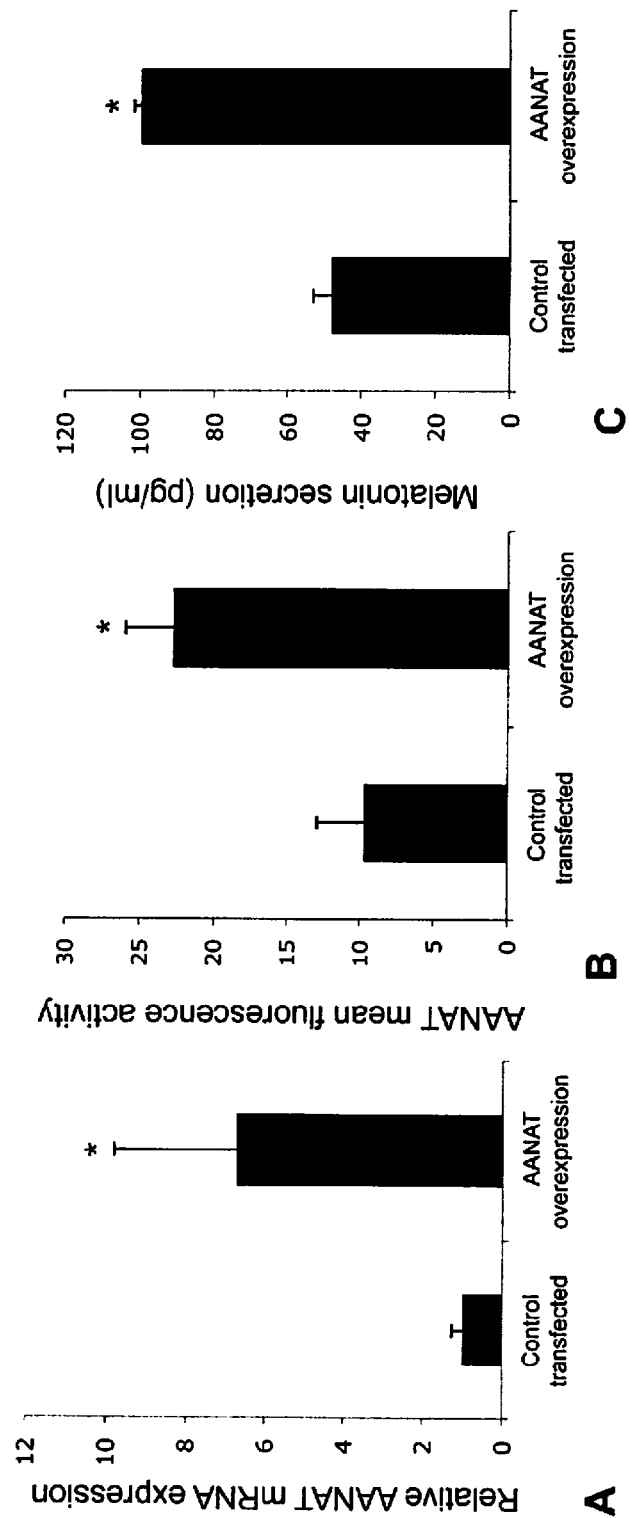
FIG. 14 [A-C] Overexpression of AANAT in large cholangiocyte lines. Data are mean±SEM of 3 experiments. *p<0.05 vs. the corresponding value of cholangiocytes transfected with the control vector.
Figures 15A, 15B:
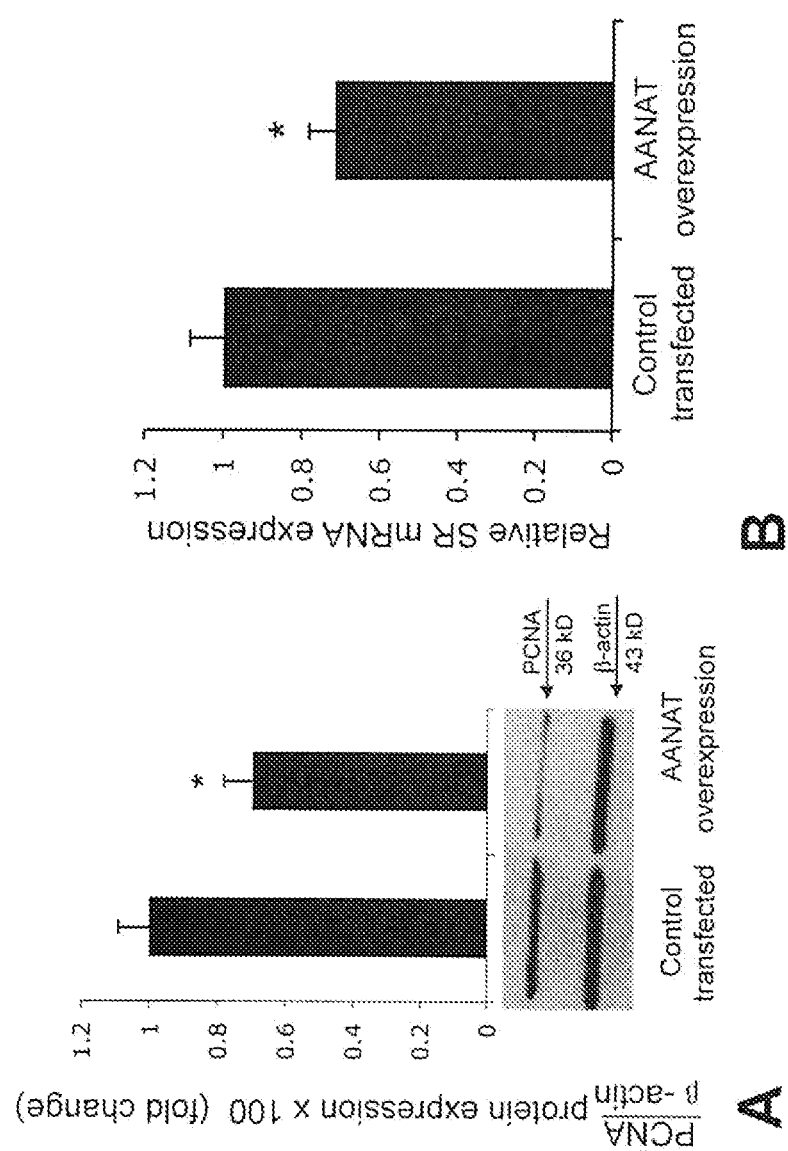
FIG. 15 In cholangiocytes overexpressing AANAT, there was: (i) decreased protein expression of [A] PCNA; and (ii) reduced mRNA (B-D) and protein (E) of SR, CFTR and $Cl^-/HCO_3^-$ AE2 compared to cholangiocytes transfected with control vector. Data are mean±SEM of 3 experiments. *p<0.05 vs. the corresponding value of cholangiocytes transfected with control vector. [F-G] Secretin did not increase cAMP levels and $Cl^-$ efflux (at 360 seconds following secretin treatment) in AANAT stably overexpressing cholangiocytes but enhanced these two parameters in cholangiocytes transfected with control vector. Data are mean±SEM of 7 experiments. *p<0.05 vs. the corresponding value of cholangiocytes transfected with the control vector.
Figures 15C, 15D:
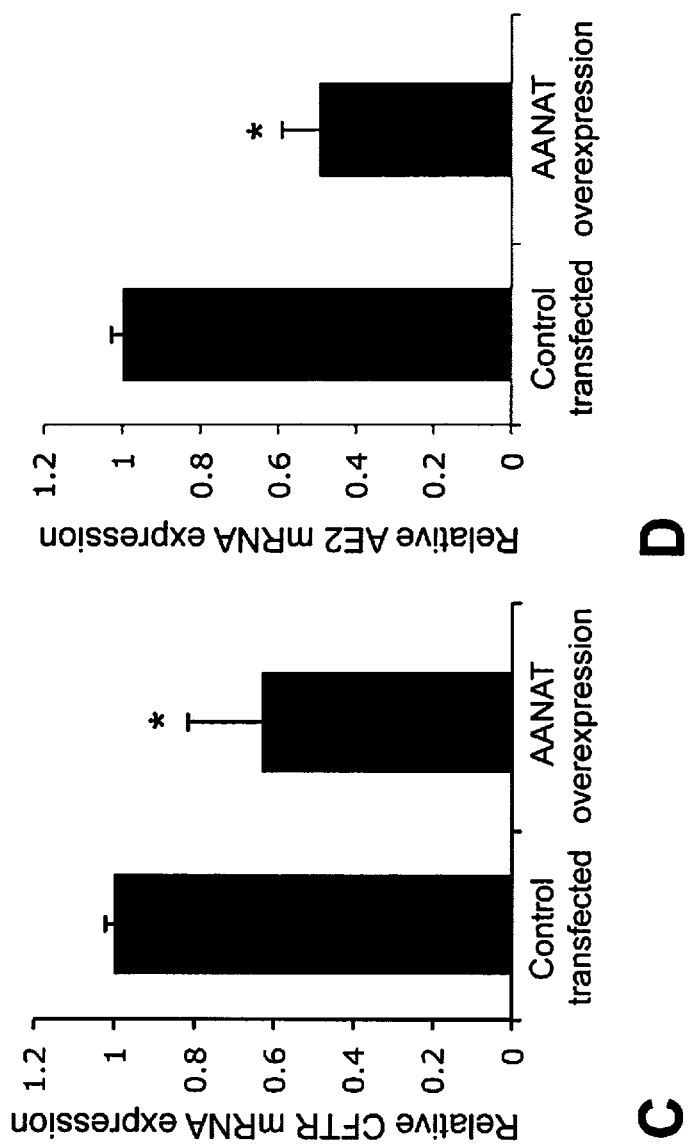
Figure 15E:
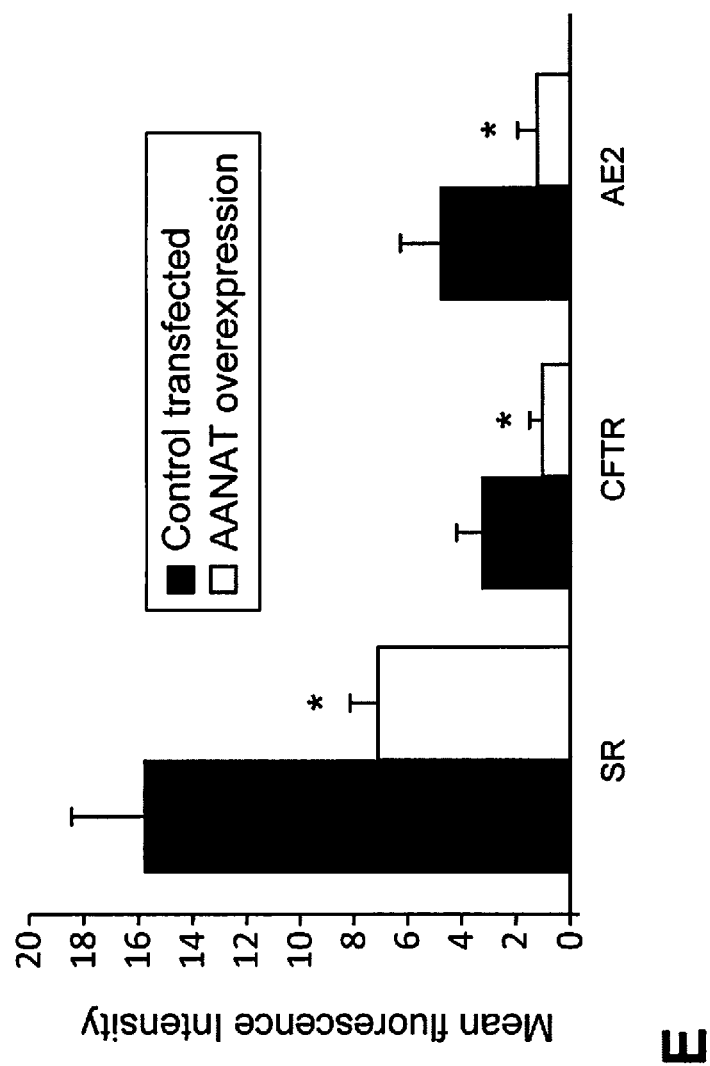
Figures 15F, 15G:
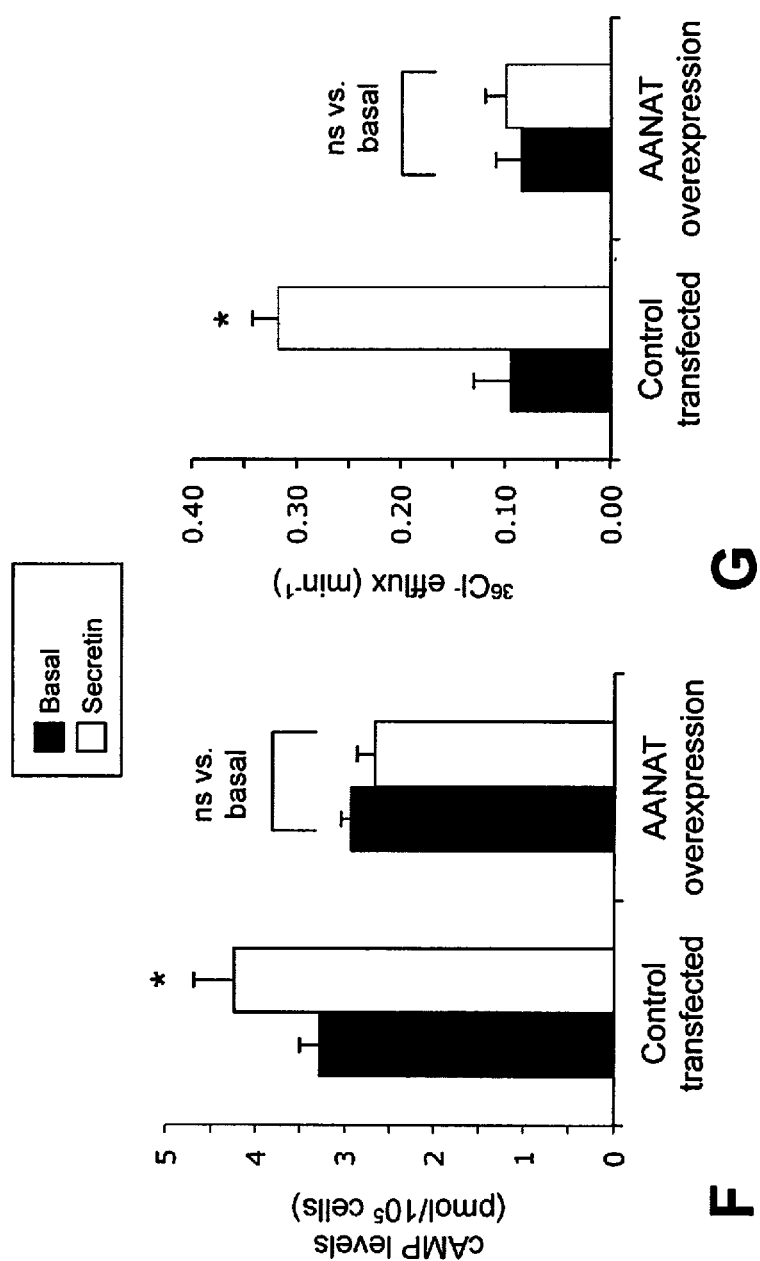

Effect of Overexpression of AANAT in MCL on the Expression of PCNA, SR, CFTR and $Cl^-/HCO_3^-$ AE2 and VEGF-A/C There was enhanced mRNA and protein expression for AANAT (FIG. 14A-B) and increased melatonin secretion (FIG. 14C) in AANAT-transfected cholangiocytes compared to cholangiocytes transfected with the control vector. In cholangiocytes overexpressing AANAT, there was: (i) decreased protein expression of PCNA (FIG. 15A); and (ii) reduced mRNA (FIG. 15B-D) and protein (FIG. 15E) expression for SR, CFTR and $Cl^-/HCO_3^-$ AE2 compared to cholangiocytes transfected with the control vector. Secretin did not increase cAMP levels and $Cl^-$ efflux (at 360 seconds following the treatment with secretin) in stably AANAT overexpressing cholangiocytes. As expected (Alpini et al., 1997), secretin stimulated cAMP and $Cl^-$ efflux in large cholangiocytes transfected with the control vector (FIG. 6).

Significance of Certain Embodiments of the Invention

Embodiments of the present invention demonstrate that: (i) AANAT is expressed in the liver mainly by cholangiocytes; and (ii) local modulation of biliary AANAT expression alters cholangiocyte growth and secretin-stimulated ductal secretion. Specifically, it was demonstrated that: (i) AANAT immunoreactivity is mostly expressed by bile ducts, and AANAT mRNA and protein expression are upregulated after BDL and by prolonged administration of melatonin to BDL rats; and (ii) AANAT expression is decreased in liver samples and cholangiocytes, and increased in pineal gland and small intestine RNA from normal rats treated with AANAT Vivo-Morpholino compared to controls. Concomitant with reduced AANAT biliary expression, there was enhanced immunoreactivity of PCNA and CK-19, SR, CFTR, $Cl^-/HCO_3^-$ AE2, and VEGF-A/C in liver sections from AANAT Vivo-Morpholino treated rats compared to controls. There was increased mRNA expression for PCNA, SR, CFTR, $Cl^-/HCO_3^-$ AE2, and VEGF-A/C in total liver samples and cholangiocytes from normal rats treated with AANAT Vivo-Morpholino compared to controls. In vitro overexpression of AANAT in cholangiocytes decreased: (i) the expression of PCNA, SR, CFTR, $Cl^-/HCO_3^-$ AE2, and VEGF-A/C; and (ii) secretin-stimulated cAMP levels and $Cl^-$ efflux.

There is growing information regarding the autocrine regulation of cholangiocyte growth/damage by neuroendocrine factors (Alvaro et al, 2007; Gaudio et al., 2006; Glaser et al., 2008). Serotonin regulates hyperplastic and neoplastic biliary growth both in vivo and in vitro models (Marzioni et al., 2005; Alpini et al., 2008). Blocking VEGF secretion decreases cholangiocyte proliferation, thus revealing an autocrine loop wherein cholangiocytes secrete VEGF interacting with VEGF-R2/R3 to increase cholangiocyte proliferation (Gaudio et al., 2006). In cholangiocytes from polycystic liver disease, VEGF expression is upregulated and VEGF supports cholangiocyte proliferation via autocrine mechanisms (Fabris et al., 2006). Although melatonin synthesis is dysregulated in cholangiocarcinoma (Han et al., 2011), no data exists regarding the autocrine role of melatonin (secreted by cholangiocytes) in the regulation of biliary hyperplasia.

Vivo-Morpholino approaches are increasingly used for evaluating the role of several genes in the regulation of hepatobiliary functions. Monga et al. have used phosphorodiamidate Morpholino oligomers to evaluate the role of β-catenin in cell proliferation/apoptosis and early biliary lineage commitment of bipotential stem cells in developing liver (Monga et al., 2003). In zebrafish, Morpholino antisense oligonucleotide-mediated knockdown of planar cell polarity genes such as prickle-1a led to developmental biliary abnormalities as well as localization defects of the liver (Cui et al., 2011).

The expression of AANAT was measured in liver sections, total liver and cholangiocytes, and melatonin serum levels in the models. AANAT expression was measured in normal and BDL rats, and BDL rats treated with melatonin to demonstrate a link between AANAT expression and cholangiocyte proliferation in well-established models of biliary hyperplasia (BDL) (Alpini et al., 1988; Renzi et al., 2011) and reduced cholangiocyte proliferation (BDL+melatonin) (Renzi et al., 2011). The increase of AANAT biliary expression following BDL is likely due to a compensatory mechanism and correlates with increased melatonin serum levels observed in cholestatic rats (Renzi et al., 2011), increase that may be due to enhanced secretion of melatonin not only from cholangiocytes but also from small intestine and pineal gland (Reiter, 1991; Bubenik, 2002). The increase in AANAT expression by the pineal gland may be due to a compensatory mechanism to ameliorate cholestatic-induced oxidative stress (Polat and Enre, 2006). The enhanced biliary expression of AANAT in melatonin-treated BDL rats is supported by a number of studies in rats and humans (Renzi et al., 2011; Dollins et al., 1994). The reduction of biliary AANAT expression and melatonin secretion in cholangiocytes (following AANAT Vivo-Morpholino administration) supports the validity of our model and the hypothesis that the AANAT expression melatonin secretion axis is an important autocrine loop regulating locally biliary proliferation. The increase in melatonin serum levels observed in rats treated with AANAT Vivo-Morpholino is likely due to higher expression of AANAT (and likely melatonin secretion) by other sites such as pineal glands and intestine to compensate for loss of biliary AANAT expression/melatonin secretion. Although the findings support the concept that AANAT is an important autocrine player for the local regulation of biliary hyperplasia, in certain aspects other paracrine pathways (regulated by the pineal gland) may be important for the regulation of biliary functions. Indeed, studies aimed to evaluate the effects of changes in the central synthesis of melatonin (e.g., following pinealectomy) in the regulation of biliary functions are ongoing.

Having demonstrated that AANAT is mostly expressed by cholangiocytes and AANAT expression is upregulated by BDL and melatonin administration, it is demonstrated that reduction of biliary AANAT expression (by AANAT Vivo-Morpholino) stimulates cholangiocyte proliferation and IBDM, and the expression of SR, CFTR, $Cl^-/HCO_3^-$ AE2 and VEGF-A/C. The fact that changes in AANAT expression modulates biliary VEGF-A/C expression is of particular importance since these two angiogenic factors have been shown to sustain biliary growth by autocrine mechanisms (Gaudio et al., 2006; Gaudio et al., 2006; Spirli et al., 2010). In support of the findings, the anti-angiogenic activity of melatonin has been demonstrated in advanced cancer patients (Lissoni et al., 2001). Also, melatonin suppresses tumor angiogenesis by inhibiting HIF-1alpha stabilization under hypoxia (Park et al., 2010). Since melatonin may affect the angiogenesis of the peribiliary vascular plexus sustaining biliary functions (Gaudio et al., 2006), pharmacological targeting of AANAT is useful for the modulation of biliary disorders, in certain aspects of the invention.

To determine that the effects of downregulation of AANAT on biliary growth depend on a direct effect on cholangiocytes, AANAT was overexpressed in cholangiocytes and an increase was demonstrated in: (i) biliary proliferation; (ii) expression of SR, CFTR, $Cl^-/HCO_3^-$ AE2 and VEGF-A/C; and (ii) secretin-stimulated cAMP levels and $Cl^-$ efflux. The data provides strong evidence that AANAT is an important local regulator of biliary growth and ductal secretion. The findings indicate that modulation of AANAT biliary expression is an important therapeutic approach for the local management of cholangiopathies.

Example 12

Pineal Gland Modulation

In certain embodiments of the invention, an individual treated with methods and compositions of the invention is subjected to methods that impact the pineal gland and/or production of melatonin thereof. In research animal models, the pineal gland may be removed by pinealectomy, for example (Kuszak and Rodin, 1977; Maganhin et al., 2009). The levels of melatonin in the research animal is then determined by standard means in the art. In some aspects of the invention, the research animal is also subjected to bile duct ligation surgery, which is a known procedure in the art (Charles River Laboratories, Wilmington, Mass.). Either groups of research animals may be subjected to particular light/dark cycles to impact melatonin levels.

Example 13

Identification of Target Genes for Specific miRNAs

Based on 3'-UTR sequence analysis and prediction algorithms, several proteins are targeted by each miRNA. Interestingly, the target prediction program miRNA Viewer database (http://cbio.mskcc.org/cgi-bin/mirnaviewer/mirnaviewer.pl) indicated the presence of a highly conserved binding site for miR-25 in 3'-UTR region of AANAT (FIG. 16A). miRNA viewer is based on miRanda software for miRNA predication of potential targets (The parameters were: Score Threshold: 155: Energy Threshold −26.2 kCal/mol; Conservation: 97.0%). miR-141/miR-200a is also predicted to target Clock gene, whereas miR-34a is predicted to target PER1 (FIG. 16B). To demonstrate Clock expression pattern in human CCA, 24 human CCA and matched noncancerous tissues were analyzed by immunohistochemistry. The human CCA tissue array showed the signal intensity was weak (+) or negative (−) in 19 out of 24 HCC tissues; while the strong (+++) or positive (++) signals were seen in only 5 out of 24 samples of CCA tissues. Therefore, the Clock protein expression was lower in the CCA tissues compared to non-cancerous tissues (p<0.01). CLOCK is also downregulated in malignant cholangiocytes relative to nonmalignant HiBEC controls (FIG. 16C). To confirm that Clock is a target of translational regulation by miR-141 in cholangiocytes, studies were performed using luciferase reporter constructs containing the miR-141 recognition sequence (FIG. 16D) from the 3'-UTR of Clock inserted downstream of the luciferase gene. Transfection with miR-141 precursor decreased reporter activity in Mz-ChA-1 cells. When these studies were repeated with reporter constructs containing random mutations in the recognition sequence, the effects of reporter deactivation by miR-141 precursor were abolished (FIG. 16E). An increase in Clock expression occurred in three CCA cell lines after 2 days incubated with anti-miR-141 inhibitor (FIG. 16F). Concomitant with enhanced Clock expression, there was a decrease of Ki67 expression, an established proliferation marker in CCA cells. These findings indicate that CLOCK, AANAT and PER1 are a biologically relevant targets of miR-141/miR-200a, miR-25 and miR-34a, respectively, in certain embodiments of the invention.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,683,202
U.S. Pat. No. 4,797,368
U.S. Pat. No. 5,139,941
U.S. Pat. No. 5,925,565
U.S. Pat. No. 5,928,906
U.S. Pat. No. 5,935,819
U.S. Pat. No. 6,506,559
U.S. Pat. No. 6,573,099
U.S. Patent Publn. 2002/0168707
U.S. Patent Publn. 2003/0051263
U.S. Patent Publn. 2003/0055020
U.S. Patent Publn. 2003/0159161
U.S. Patent Publn. 2004/0064842
U.S. Patent Publn. 2004/0265839
Akbulut et al., *J. Pineal. Res.*, 47:308-12, 2009.
Alpini et al., *Am. J. Physiol. Gastrointest. Liver Physiol.*, 272: G1064-1074, 1997.
Alpini et al., *Am. J. Physiol. Gastrointest. Liver Physiol.*, 274: G767-775, 1998.
Alpini G, Invernizzi P, Gaudio E, Venter J, Kopriva S, Bernuzzi F, Onori P, et al. Serotonin metabolism is dysregulated in cholangiocarcinoma, which has implications for tumor growth. Cancer Res 2008; 68:9184-9193.
Alpini G, Lenzi R, Sarkozi L, Tavoloni N. Biliary physiology in rats with bile ductular cell hyperplasia. Evidence for a secretory function of proliferated bile ductules. J Clin Invest 1988; 81:569-578.
Alpini G, Prall R T, LaRusso N F. The pathobiology of biliary epithelia. The Liver; Biology & Pathobiology, 4E. I. M. Arias, J. L. Boyer, F. V. Chisari, N. Fausto, W. Jakoby, D. Schachter, and D. A. Shafritz D. Philadelphia, Pa.: Lippincott Williams & Wilkins. 2001:421-435.
Alpini G, Ulrich C, Roberts S, Phillips J O, Ueno Y, Podila P V, Colegio O, et al. Molecular and functional heterogeneity of cholangiocytes from rat liver after bile duct ligation. Am J Physiol Gastrointest Liver Physiol 1997; 272:G289-297.
Alpini G, Ulrich C D, 2nd, Phillips J O, Pham L D, Miller L J, LaRusso N F. Upregulation of secretin receptor gene expression in rat cholangiocytes after bile duct ligation. Am J Physiol Gastrointest Liver Physiol 1994; 266:G922-928.
Alvaro D, Cho W K, Mennone A, Boyer J L. Effect of secretion on intracellular pH regulation in isolated rat bile duct epithelial cells. J Clin Invest 1993; 92:1314-1325.
Alvaro D, Mancino M G, Glaser S, Gaudio E, Marzioni M, Francis H, Alpini G. Proliferating cholangiocytes: a neuroendocrine compartment in the diseased liver. Gastroenterology 2007; 132:415-431.
Ando et al., *Clin. Exp. Hypertens.*, 31:201-207, 2009.
Anisimov et al., *Int. J. Cancer*, 103:300-305, 2003.
Arai et al., *Pathol. Int.*, 55: 122-129, 2005.
Arora V, Knapp D C, Reddy M T, Weller D D, Iversen P L. Bioavailability and efficacy of antisense morpholino oligomers targeted to c-myc and cytochrome P-450 3A2 following oral administration in rats. J Pharm Sci 2002; 91:1009-1018.
Ashley, C. E. et al. Nature Mater. 10, 389-397 (2011).
Blask et al., *Breast Cancer Res. Treat.*, 79:313-20, 2003.
Blask et al., *Cancer Res.*, 65:11174-84, 2005.
Boussif et al., *Proc. Natl. Acad. Sci. USA*, 92(Francis H et al., 2009):7297-7301, 1995.
Bubenik G A. Gastrointestinal melatonin: localization, function, and clinical relevance. Dig Dis Sci 2002; 47:2336-2348.
Cabrera et al., *J. Pineal. Res.*, 49(Alpini G et al., 2008):45-54, 2010.
Caley et al., *J. Virology*, 71(4):3031-3038, 1997.
Cao et al., *Cancer Res.*, 69:7619-25, 2009.
Chandler et al., *Proc. Natl. Acad. Sci. USA*, 94(8):3596-601, 1997.
Chen, Y. et al., *Molecular Therapy* vol. 18 no. 9 Sep. 2010.
Chen and Okayama, *Mol. Cell Biol.*, 7(8):2745-2752, 1987.
Coffin, In: *Virology*, Fields et al. (Eds.), Raven Press, NY, 1437-1500, 1990.
Coon et al., *Science*, 270: 1681-1683, 1995.
Cui S, Capecci L M, Matthews R P. Disruption of planar cell polarity activity leads to developmental biliary defects. Dev Biol 2011; 351:229-241.
Davis et al., *J. Virol.*, 70(6):3781-3787, 1996.
DeMorrow et al., *J Biol. Chem.*, 282: 13098-13113, 2007.
Dollins A B, Zhdanova I V, Wurtman R J, Lynch H J, Deng M H. Effect of inducing nocturnal serum melatonin concentrations in daytime on sleep, mood, body temperature, and performance. Proc Natl Acad Sci USA 1994; 91:1824-1828.
Donohue et al., *DNA Cell Biol.*, 12: 715-727, 1993.
Drazen et al., *Am. J. Physiol. Regul. Integr. Comp. Physiol.*, 280:R1476-1482, 2001.
Eismann et al., *Psychoneuroendocrinology*, 35(7):963-76, 2010.
Esrefoglu M, Gul M, Emre M H, Polat A, Selimoglu M A. Protective effect of low dose of melatonin against cholestatic oxidative stress after common bile duct ligation in rats. World J Gastroenterol 2005; 11:1951-1956.
Fabris L, Cadamuro M, Fiorotto R, Roskams T, Spirli C, Melero S, Sonzogni A, et al. Effects of angiogenic factor overexpression by human and rodent cholangiocytes in polycystic liver diseases. Hepatology 2006; 43:1001-1012.
Fan et al., *World J. Gastroenterol.*, 16:1473-81, 2010.
Fechheimer et al., *Proc Natl. Acad. Sci. USA*, 84:8463-8467, 1987.
Ferry et al., *Eur. J. Biochem.*, 271(2):418-28, 2004.
Fraley et al., *Proc. Natl. Acad. Sci. USA*, 76:3348-3352, 1979.
Francis et al., *Mol. Cancer Res.*, 7: 1704-1713, 2009.
Francis H, Glaser S, DeMorrow S, Gaudio E, Ueno Y, Venter J, Dostal D, et al. Small mouse cholangiocytes proliferate in response to H1 histamine receptor stimulation by activation of the $IP_3$/CaMK I/CREB pathway. Am J Physiol Cell Physiol 2008; 295:C499-513.
Francis H, LeSage G, DeMorrow S, Alvaro D, Ueno Y, Venter J, Glaser S, et al. The alpha2-adrenergic receptor agonist UK 14,304 inhibits secretin-stimulated ductal secretion by downregulation of the cAMP system in bile duct-ligated rats. Am J Physiol Cell Physiol 2007; 293: C1252-1262.
Fu and Lee, *Nat. Rev. Cancer*, 3:350-61, 2003.
Gaudio E, Barbaro B, Alvaro D, Glaser S, Francis H, Franchitto A, Onori P, et al. Administration of r-VEGF-A prevents hepatic artery ligation-induced bile duct damage in bile duct ligated rats. Am J Physiol Gastrointest Liver Physiol 2006; 291:G307-317.
Gaudio E, Barbaro B, Alvaro D, Glaser S, Francis H, Ueno Y, Meininger C J, et al. Vascular endothelial growth factor stimulates rat cholangiocyte proliferation via an autocrine mechanism. Gastroenterology 2006; 130:1270-1282.
Glaser S, DeMorrow S, Francis H, Ueno Y, Gaudio E, Vaculin S, Venter J, et al. Progesterone stimulates the proliferation of female and male cholangiocytes via autocrine/paracrine mechanisms. Am J Physiol Gastrointest Liver Physiol 2008; 295:G124-G136.
Glaser S, Gaudio E, Rao A, Pierce L M, Onori P, Franchitto A, Francis H L, et al. Morphological and functional heterogeneity of the mouse intrahepatic biliary epithelium. Lab Invest 2009; 89:456-469.
Glaser S, Lam I P, Franchitto A, Gaudio E, Onori P, Chow B K, Wise C, et al. Knockout of secretin receptor reduces large cholangiocyte hyperplasia in mice with extrahepatic cholestasis induced by bile duct ligation. Hepatology 2010; 52:204-214.
Glorioso et al., *Mol. Biotechnol.*, 4(Alpini G et al., 2008): 87-99, 1995.
Gopal, *Mol. Cell Biol.*, 5:1188-1190, 1985.
Graham and Van Der Eb, *Virology*, 52:456-467, 1973.
Grubman et al., *Am. J. Physiol. Gastrointest. Liver Physiol.*, 266: G1060-1070, 1994.
Grunhaus and Horwitz, *Seminar in Virology*, 3:237-252, 1992.
Gupta et al., Drug Dev Ind Pharm. 2012 Mar. 8. [Epub ahead of print].
Han et al., *Gastroenterology*, 138:S-792-S-3, 2010.
Han Y, Demorrow S, Invernizzi P, Jing Q, Glaser S, Renzi A, Meng F, et al. Melatonin exerts by an autocrine loop antiproliferative effects in cholangiocarcinoma: its synthesis is reduced favoring cholangiocarcinoma growth. American journal of physiology. Gastrointestinal and liver physiology 2011; 301:G623-633.
Hansen, *Epidemiology*, 12:74-7, 2001b.
Hansen, *J. Natl. Cancer Inst.*, 93:1513-5, 2001a.
Harland and Weintraub, *J. Cell Biol.*, 101(3):1094-1099, 1985.
Honma et al., *Biochem. Biophys. Res. Commun.*, 250:83-87, 1998.
Humphries A, Wells T, Baler R, Klein D C, Carter D A. Rodent Aanat: intronic E-box sequences control tissue specificity but not rhythmic expression in the pineal gland. Mol Cell Endocrinol 2007; 270:43-49.
Ishii M, Vroman B, LaRusso N F. Isolation and morphologic characterization of bile duct epithelial cells from normal rat liver. Gastroenterology 1989; 97:1236-1247.
Iuvone P M, Tosini G, Pozdeyev N, Hague R, Klein D C, Chaurasia S S. Circadian clocks, clock networks, arylalkylamine N-acetyltransferase, and melatonin in the retina. Prog Retin Eye Res 2005; 24:433-456.
J Clin Endocrinol Metab. 2005 May; 90(5):2755-61.
Jung-Hynes et al., *J. Pineal. Res.*, 49:60-8, 2010.
Kanno et al., *J. Hepatol.*, 34: 284-291, 2001.
Kanno N, LeSage G, Glaser S, Alpini G. Regulation of cholangiocyte bicarbonate secretion. Am J Physiol Gastrointest Liver Physiol 2001; 281:G612-625.
Kato et al., *J. Biol. Chem.*, 267:15523-15529, 1992.
Kayumov et al., *J. Clin. Endocrinol. Metab.*, 90(5):2755-61, 2005.
Klagge et al., *Horm. Metab. Res.*, 42: 897-899, 2010.
Knuth et al., *J. Hepatol.*, 1: 579-596, 1985.
Kusaka et al., *Hum. Cell.*, 1: 92-94, 1988.

Kuszak, J. and Rodin, M., Experientia 33/2, 283-284, 1977.
Laroui H et al., *Biomaterials.* 2011 February; 32(4):1218-28.
Laughlin et al., *J. Virol.,* 60(2):515-524, 1986.
Lazaridis and Gores, *Gastroenterology,* 128:1655-67, 2005.
Lebkowski et al., *Mol. Cell. Biol.,* 8(10):3988-3996, 1988.
Lee et al. *PLoS One,* 5:e10995, 2010.
Lejeune et al., *J. Anat.,* 212: 868-878, 2008.
Lepailleur et al. *J. Chem. Inf. Model,* March 22; 50(3):446-60, 2010.
LeSage et al., *Am. J. Physiol. Gastrointest. Liver Physiol.,* 276:G1289-1301, 1999.
LeSage et al., *Hepatology,* 40:1116-1127, 2004.
LeSage G, Glaser S, Gubba S, Robertson W E, Phinizy J L, Lasater J, Rodgers R E, et al. Regrowth of the rat biliary tree after 70% partial hepatectomy is coupled to increased secretin-induced ductal secretion. Gastroenterology 1996; 111:1633-1644.
Li et al. *J. Biol. Chem.,* 266:6562-6570, 1990.
Li Y et al., Drug Dev Ind Pharm. 2011 Nov. 17. [Epub ahead of print]
Lissoni P, Rovelli F, Malugani F, Bucovec R, Conti A, Maestroni G J. Anti-angiogenic activity of melatonin in advanced cancer patients. Neuro Endocrinol Lett 2001; 22:45-47.
Macejak and Sarnow, *Nature,* 353:90-94, 1991.
Maganhin C C et al., Acta Cirurgica Basileira, 24(4):283-324, 2009.
Maldonado et al., *Pharmacol. Res.,* 62(3):282-7, 2009.
Malhi and Gores, *J. Hepatol.,* 45:856-67, 2006.
Mancinelli R, Franchitto A, Gaudio E, Onori P, Glaser S, Francis H, Venter J, et al. After damage of large bile ducts by gamma-aminobutyric acid, small ducts replenish the biliary tree by amplification of calcium-dependent signaling and de novo acquisition of large cholangiocyte phenotypes. Am J Pathol 2010; 176:1790-1800.
Mancinelli R, Onori P, Gaudio E, DeMorrow S, Franchitto A, Francis H, Glaser S, et al. Follicle-stimulating hormone increases cholangiocyte proliferation by an autocrine mechanism via cAMP-dependent phosphorylation of ERK1/2 and Elk-1. Am J Physiol Gastrointest Liver Physiol 2009; 297:G11-26.
Martin-Renedo et al., *J. Pineal. Res.,* 45:532-40, 2008.
Marzioni M, Glaser S, Francis H, Marucci L, Benedetti A, Alvaro D, Taffetani S, et al. Autocrine/paracrine regulation of the growth of the biliary tree by the neuroendocrine hormone serotonin. Gastroenterology 2005; 128: 121-137.
Matsuo et al., *Science,* 302:255-9, 2003.
McCarty et al., *J. Virol.,* 65(6):2936-2945, 1991.
McLaughlin et al., *J. Virol.,* 62(6):1963-1973, 1988.
Meininger and Wu, *Methods Enzymol.,* 352:280-295, 2002.
Miyagiwa et al., *In Vitro Cell Dev. Biol.,* 25: 503-510, 1989.
Monga S P, Monga H K, Tan X, Mule K, Pediaditakis P, Michalopoulos G K. Beta-catenin antisense studies in embryonic liver cultures: role in proliferation, apoptosis, and lineage specification. Gastroenterology 2003; 124: 202-216.
Muzyczka, *Curr. Topics Microbiol. Immunol.,* 158:97-129, 1992.
Nagano et al., *Brain Res.,* 1289:37-48, 2009.
Nah et al., *J. Pineal. Res.,* 47:70-4, 2009.
Nicolau and Sene, *Biochim. Biophys. Acta,* 721:185-190, 1982.
Nowak et al., *Hoppe. Seylers. Z. Physiol. Chem.,* 356: 1181-1183, 1975.
Oda et al., *Anticancer Res.,* 29:1201-9, 2009.
Onori P, Wise C, Gaudio E, Franchitto A, Francis H, Carpino G, Lee V, et al. Secretin inhibits cholangiocarcinoma growth via dysregulation of the cAMP-dependent signaling mechanisms of secretin receptor. Int J Cancer 2010; 127:43-54.
Park S Y, Jang W J, Yi E Y, Jang J Y, Jung Y, Jeong J W, Kim Y J. Melatonin suppresses tumor angiogenesis by inhibiting HIF-1alpha stabilization under hypoxia. J Pineal Res 2010; 48:178-184.
PCT Appln. PCT/US99/05781
Pelletier and Sonenberg, *Nature,* 334(6180):320-325, 1988.
Peschke et al., *J. Pineal Res.,* 45: 439-448, 2008.
Polat A, Emre M H. Effects of melatonin or acetylsalicylic acid on gastric oxidative stress after bile duct ligation in rats. J Gastroenterol 2006; 41:433-439.
Popielarski S R et al., *Bioconjugate Chem.* 2005, 16, 1071-1080.
Porkka-Heiskanen et al., *J. Reprod. Fertil.,* 96:331-336, 1992.
Potter et al., *Proc. Natl. Acad. Sci. USA,* 81:7161-7165, 1984.
Ramirez et al., *Anim. Reprod. Sci.,* 115:317-322, 2009.
Ramirez-Rodriguez et al., *Neuropsychopharmacology,* 34:2180-2191, 2009.
Reiter R J. Pineal melatonin: cell biology of its synthesis and of its physiological interactions. Endocr Rev 1991; 12:151-180.
Remington's Pharmaceutical Sciences, 18th Ed. Mack Printing Company, 1289-1329, 1990.
Renzi A, Glaser S, DeMorrow S, Mancinelli R, Meng F, Franchitto A, Venter J, et al. Melatonin inhibits cholangiocyte hyperplasia in cholestatic rats by interaction with MT1 but not MT2 melatonin receptors. Am J Physiol Gastrointest Liver Physiol 2011; 301:G634-643.
Reppert et al., *Neuron,* 13: 1177-1185, 1994.
Reppert et al., *Proc. Natl. Acad. Sci. USA,* 92: 8734-8738, 1995.
Rippe, et al., *Mol. Cell Biol.,* 10:689-695, 1990.
Rutenburg et al., *J. Histochem. Cytochem.,* 17:517-526, 1969.
Saijyo et al., *Tohoku J. Exp. Med.,* 177: 61-71, 1995.
Samulski et al., *J. Virol.,* 63:3822-3828, 1989.
Sanchez-Barcelo et al., *Curr. Med. Chem.,* 17(19):2070-95 2010.
Sewerynek et al., *J. Cell Biochem.,* 58: 436-444, 1995.
Shimizu et al., *Int. J. Cancer,* 52: 252-260, 1992.
Shiu et al., *J. Pineal. Res.,* 49:301-311, 2010.
Spirli C, Okolicsanyi S, Fiorotto R, Fabris L, Cadamuro M, Lecchi S, Tian X, et al. Mammalian target of rapamycin regulates vascular endothelial growth factor-dependent liver cyst growth in polycystin-2-defective mice. Hepatology 2010; 51:1778-1788.
Storto et al., *Genes Chromosomes Cancer,* 2: 300-310, 1990.
Strausberg et al., *Proc. Natl. Acad. Sci. USA,* 99:16899-16903, 2002.
Summerton J E. Morpholino, siRNA, and S-DNA compared: impact of structure and mechanism of action on off-target effects and sequence specificity. Curr Top Med Chem 2007; 7:651-660.
Szewczuk et al. *J. Med. Chem.,* 50 (22): 5330-8, 2007.
Tahan G, Akin H, Aydogan F, Ramadan S S, Yapicier O, Tarcin O, Uzun H, et al. Melatonin ameliorates liver fibrosis induced by bile-duct ligation in rats. Can J Surg 2010; 53:313-318.
Tamura et al., *PLoS One,* 5: e13958, 2010.
Tian et al., *Nanomedicine.* 2011 Nov. 16. [Epub ahead of print]

Tratschin et al., *Mol. Cell. Biol.*, 4:2072-2081, 1984.
Trompeter et al, *J. Immunol. Methods*, 274(1-2):245-56, 2003.
Tur-Kaspa et al., *Mol. Cell Biol.*, 6:716-718, 1986.
Ueno Y, Alpini G, Yahagi K, Kanno N, Moritoki Y, Fukushima K, Glaser S, et al. Evaluation of differential gene expression by microarray analysis in small and large cholangiocytes isolated from normal mice. Liver Int 2003; 23:449-459.
Vanecek, *Rev. Reprod.*, 4:67-72, 1999.
Velissaris et al. *World J. Gastroenterol.*, 14:4190-4195, 2008.
Vroman et al., *Lab. Invest.*, 74: 303-313, 1996.
Woo et al., *J. Physiol.*, 586: 2779-2798, 2008.
Wu and Wu, *Biochemistry*, 27: 887-892, 1988.
Wu and Wu, *J. Biol. Chem.*, 262:4429-4432, 1987.
Yang and Russell, *Proc. Natl. Acad. Sci. USA*, 87:4144-4148, 1990.
Yang et al., *Breast Cancer Res. Treat.*, 117:423-31, 2009b.
Yang et al., *Chronobiol. Int.*, 26:1323-39, 2009a.
Yutzey et al. *Mol. Cell. Biol.*, 9:1397, 1989.
Zawilska et al., *Pharmacol. Rep.*, 61:383-410, 2009.
Zeman et al., *J. Hypertens. Suppl.*, 27:S21-26, 2009.
Zheng and Cole, *Bioorg. Chem.*, 31 (5):398-411, 2003.

v) an exogenous CLOCK (Circadian Locomotor Output Cycles Kaput) expression cassette, and
vi) melatonin,
wherein the proliferation of cholangiocytes in the subject is inhibited.

2. The method of claim 1, wherein the condition is cholangiocarcinoma.

3. A method of treating a subject known to have or suspected of having biliary hyperplasia, cholestasis, cholangiopathy, cholangiocarcinoma, primary biliary cirrhosis (PBC) or primary sclerosing cholangitis (PSC), comprising administering to the subject a pharmaceutically effective amount of a composition comprising melatonin or a melatonin analog, wherein the composition is injected into a bile duct of the subject.

4. A method of treating a subject having a bile duct disease selected from the group consisting of liver transplant, drug-induced ductopenia, congenital ductopenia, obstruction, infection, or gall stones, comprising administering to the subject an agent that decreases activity or expression of AANAT in the subject.

5. The method of claim 4, wherein the agent that decreases activity or expression of AANAT in the cholangiocyte is selected from the group consisting of Coenzyme A-S-acetyltryptamine, siRNA, miRNA, and small molecules.

6. The method of claim 5, wherein the miRNA is selected from the group consisting of miRNA-17, miRNA-19, miRNA-34, miRNA 125b, miRNA-132, miR-4279, miR-875-3p, miR-1299, miR-626, miR-483-5p, miR-542-5p, hsa-miR-129*, hsa-miR-129-3p, hsa-miR-610, hsa-miR-1915, hsa-miR-541, hsa-miR-654-5p, hsa-miR-326, hsa-miR-330-5p, hsa-miR-885-3p, hsa-miR-1253, hsa-miR-136, hsa-miR-1972, hsa-miR-4261, hsa-miR-1207-3p, hsa-miR-518c*, hsa-miR-1225-3p, hsa-miR-93*, hsa-miR-877*, hsa-miR-96*, hsa-miR-575, and a mixture thereof.

What is claimed is:

1. A method for treating biliary hyperplasia, cholestasis, cholangiopathy, cholangiocarcinoma, primary biliary cirrhosis (PBC) or primary sclerosing cholangitis (PSC) in a subject, comprising administering to the subject in need thereof a pharmaceutically effective amount of one or more agents selected from the group consisting of:
   i) an exogenous AANAT (aralkylamine N-acetyltransferase) expression cassette,
   ii) an exogenous ASMT (acetylserotonin O-methyltransferase) expression cassette,
   iii) an exogenous Per1 (period circadian protein homolog 1) expression cassette,
   iv) an exogenous Bmal1 (brain and muscle aryl hydrocarbon receptor nuclear translocator (ARNT)-like) inhibitory nucleic acid or nucleic acid analog,

* * * * *